US008685381B2

(12) United States Patent
Schlessinger et al.

(10) Patent No.: US 8,685,381 B2
(45) Date of Patent: Apr. 1, 2014

(54) TOPICAL BASE AND ACTIVE AGENT-CONTAINING COMPOSITIONS, AND METHODS FOR IMPROVING AND TREATING SKIN

(76) Inventors: Joel Schlessinger, Omaha, NE (US); Daniel Isaac Schlessinger, Omaha, NE (US)

( * ) Notice: Subject to any disclaimer, the term of this patent is extended or adjusted under 35 U.S.C. 154(b) by 0 days.

(21) Appl. No.: 13/233,012

(22) Filed: Sep. 14, 2011

(65) Prior Publication Data
US 2012/0237556 A1    Sep. 20, 2012

Related U.S. Application Data

(63) Continuation-in-part of application No. 12/925,464, filed on Oct. 23, 2010, now abandoned.

(51) Int. Cl.
*A61K 8/49* (2006.01)
*A61K 31/74* (2006.01)
*C07J 5/00* (2006.01)
*C07J 7/00* (2006.01)

(52) U.S. Cl.
USPC .............. 424/78.02; 424/59; 424/63; 424/64; 424/70.16; 424/70.9; 424/78.03; 424/78.05; 424/78.06; 424/78.07; 552/502; 552/557; 552/559; 552/569; 552/570; 552/577

(58) Field of Classification Search
None
See application file for complete search history.

(56) References Cited

U.S. PATENT DOCUMENTS

| | | | |
|---|---|---|---|
| 3,644,613 A | 2/1972 | Moeller et al. .................. 424/49 |
| 3,914,131 A | 10/1975 | Hutchison ...................... 106/268 |
| 3,947,571 A | 3/1976 | Murphy et al. ................. 424/64 |
| 3,954,114 A | 5/1976 | Ostrowsky et al. .......... 132/88.7 |
| 3,957,969 A | 5/1976 | Fujiyama ........................ 424/64 |
| 3,960,757 A | 6/1976 | Morishita et al. ............. 427/213 |
| 3,976,789 A | 8/1976 | Tomita et al. ................. 424/365 |
| 3,981,996 A | 9/1976 | Leigh ............................ 514/169 |
| 4,048,309 A | 9/1977 | Chen et al. .................... 424/238 |
| 4,060,492 A | 11/1977 | Yasui et al. ..................... 252/59 |
| 4,066,789 A | 1/1978 | Mores et al. .................. 424/635 |
| 4,078,147 A | 3/1978 | Ukai et al. .................... 560/180 |
| 4,137,302 A | 1/1979 | Humbert et al. ............... 424/47 |
| 4,151,272 A | 4/1979 | Geary et al. .................... 424/68 |
| 4,177,267 A | 12/1979 | Herschler ..................... 424/238 |
| 4,199,576 A | 4/1980 | Reller et al. .................. 424/230 |
| 4,226,889 A | 10/1980 | Yuhas ............................ 424/59 |
| 4,229,432 A | 10/1980 | Geria ............................ 424/68 |
| 4,252,796 A | 2/1981 | Yu et al. ........................ 514/181 |
| 4,284,630 A | 8/1981 | Yu et al. ........................ 514/179 |
| 4,291,018 A | 9/1981 | Oeda .............................. 424/64 |
| 4,292,088 A | 9/1981 | Scheuffgen .................... 106/268 |
| 4,299,828 A | 11/1981 | Wang et al. ................... 424/238 |
| 4,305,961 A | 12/1981 | Tsutsumi ...................... 424/361 |
| 4,322,400 A | 3/1982 | Yuhas ............................ 424/59 |
| 4,346,086 A | 8/1982 | Sattler et al. .................. 514/179 |
| 4,367,220 A | 1/1983 | Boulogne et al. .............. 424/64 |
| 4,386,067 A | 5/1983 | Guillon .......................... 424/95 |
| 4,393,044 A | 7/1983 | Takada et al. .................. 424/64 |
| 4,478,853 A | 10/1984 | Chaussee ...................... 514/772 |
| 4,496,554 A | 1/1985 | Wong ............................ 514/179 |
| 4,504,465 A | 3/1985 | Sampson et al. ............... 424/65 |
| 4,610,978 A | 9/1986 | Dikstein et al. ................. 514/46 |
| 4,678,663 A | 7/1987 | Scott ............................. 424/62 |
| 4,695,452 A | 9/1987 | Gunnis et al. .................. 424/59 |
| 4,702,916 A | 10/1987 | Geria ............................ 424/400 |
| 4,847,069 A | 7/1989 | Bissett et al. .................. 424/47 |
| 4,847,071 A | 7/1989 | Bissett et al. .................. 424/59 |
| 4,847,072 A | 7/1989 | Bissett .......................... 424/59 |
| 4,879,274 A | 11/1989 | Kamiya et al. ................ 424/780 |
| 4,892,890 A | 1/1990 | Damani ........................ 514/784 |
| 4,900,541 A | 2/1990 | Govier .......................... 424/47 |
| 4,902,682 A | 2/1990 | Sattler .......................... 514/179 |
| 4,996,044 A * | 2/1991 | Mercado et al. ............... 424/64 |
| 5,061,700 A | 10/1991 | Dow et al. .................... 514/169 |
| 5,185,150 A | 2/1993 | DeLuca et al. ................ 424/401 |
| 5,254,109 A | 10/1993 | Smith et al. .................. 604/289 |
| 5,290,561 A | 3/1994 | Farhadieh .................... 424/449 |
| 5,292,512 A | 3/1994 | Schaefer et al. .............. 424/401 |
| 5,543,148 A | 8/1996 | Lapidus ....................... 424/401 |

(Continued)

OTHER PUBLICATIONS

Fancol VB search result in Google showing date that the web page was published. Available online Feb. 11, 2009; downloaded Feb. 9, 2012.*
Finsolv TN search result in Google showing date that the web page was published. Available online Jun. 7, 2010; downloaded Feb. 9, 2012.*
Natunola Castor 1023 search result in Google showing date that the web page was published. Available online as early as Jul. 19, 2007; downloaded Feb. 9, 2012.*
Fancol VB data sheet, published online Feb. 11, 2009; downloaded Nov. 7, 2012.*
Finsolv TN NPL product sheet; published online Jun. 7, 2010; downloaded Nov. 7, 2012.*

(Continued)

*Primary Examiner* — Robert A Wax
*Assistant Examiner* — Jeffrey T Palenik
(74) *Attorney, Agent, or Firm* — Roberta L. Hastreiter; Keith D. Parr; Locke Lord LLP

(57) ABSTRACT

The invention provides skin protecting and penetrating, easy-to-administer base and active agent-containing compositions, such as those including hydrocortisone, for treating the skin of mammals for different dermatologic disorders. This is effected by topically administering effective amounts of the compositions thereto in forms that address the skin and mucosa of the mouth and lips, and the rest of the body. Additionally, an optional flavoring addition to these products affords significantly better tasting, and less bitter, compositions, allowing a more pleasant experience and better compliance by patients. The compositions include a unique formulation of FANCOL VB, Natunola Castor 1023, Finsolv TN, bees wax and, optionally, one or a plurality of plant or plant seed oils, fatty alcohols, fats and flavorings, in desirable weight percents thereof, in various forms, and preferably in a form of a solid roll-on stick in a variety of sizes and of a jar or pot.

52 Claims, 19 Drawing Sheets
(19 of 19 Drawing Sheet(s) Filed in Color)

(56) References Cited

U.S. PATENT DOCUMENTS

| | | | | |
|---|---|---|---|---|
| 5,622,993 | A | 4/1997 | McGinity | 514/626 |
| 5,653,989 | A | 8/1997 | Sattler | 424/401 |
| 5,660,839 | A | 8/1997 | Allec et al. | 424/401 |
| 5,756,014 | A | 5/1998 | Mathur | 264/4.1 |
| 5,785,976 | A | 7/1998 | Westensen | 424/400 |
| 5,804,572 | A | 9/1998 | Blank | 514/159 |
| 5,951,991 | A | 9/1999 | Wagner | 424/401 |
| 5,961,997 | A | 10/1999 | Swinehart | 424/401 |
| 5,972,361 | A | 10/1999 | Fowler | 424/402 |
| 5,976,555 | A | 11/1999 | Liu | 424/401 |
| 5,990,100 | A | 11/1999 | Rosenberg et al. | 514/174 |
| 6,063,397 | A | 5/2000 | Fowler | 424/443 |
| 6,096,326 | A | 8/2000 | Wikholm | 424/401 |
| 6,126,920 | A | 10/2000 | Jones | 424/45 |
| 6,132,746 | A | 10/2000 | Hasenoehrl | 424/403 |
| 6,228,351 | B1 | 5/2001 | Viders | 424/64 |
| 6,231,872 | B1 | 5/2001 | Mooney et al. | 424/400 |
| 6,251,425 | B1 | 6/2001 | Mathur | 424/450 |
| 6,258,346 | B1 | 7/2001 | Scavone et al. | 424/65 |
| 6,342,208 | B1 | 1/2002 | Hyldgaard et al. | 424/59 |
| 6,375,942 | B1 | 4/2002 | Rico | 424/78.07 |
| 6,403,123 | B1 | 6/2002 | Van Scott et al. | 424/489 |
| 6,479,058 | B1 | 11/2002 | McCadden | 424/401 |
| 6,503,944 | B1 | 1/2003 | Chanchani | 514/506 |
| 6,528,071 | B2 | 3/2003 | Vatter et al. | 424/401 |
| 6,558,680 | B1 | 5/2003 | Riedel et al. | 424/401 |
| 6,613,338 | B1 | 9/2003 | Schreiber | 424/401 |
| 6,753,013 | B1 | 6/2004 | Didrekson et al. | 424/484 |
| 6,765,001 | B2 | 7/2004 | Gans | 514/172 |
| 6,780,439 | B2 | 8/2004 | Wilk | 424/642 |
| 6,787,529 | B2 | 9/2004 | Hoy | 514/167 |
| 6,790,460 | B2 | 9/2004 | Shefer et al. | 424/489 |
| 6,830,758 | B2 | 12/2004 | Nichols | 424/443 |
| 6,881,756 | B2 | 4/2005 | Gendimenico | 514/732 |
| 6,926,886 | B2 | 8/2005 | Lin et al. | 424/59 |
| 6,964,782 | B1 | 11/2005 | Smith et al. | 424/616 |
| 6,967,023 | B1 | 11/2005 | Eini et al. | 424/401 |
| 6,979,454 | B1 | 12/2005 | Lindahl | 424/409 |
| 7,109,246 | B1 | 9/2006 | Hawtin | 514/171 |
| 7,666,859 | B2 | 2/2010 | Turkowitz | 514/171 |
| 2003/0099604 | A1 | 5/2003 | Light | |
| 2003/0199838 | A1 | 10/2003 | Sheridan | |
| 2003/0232091 | A1 | 12/2003 | Shefer | |
| 2004/0091539 | A1 | 5/2004 | Lindahl et al. | |
| 2004/0151671 | A1 | 8/2004 | Abram et al. | |
| 2004/0202725 | A1 | 10/2004 | Dascalu | |
| 2004/0235803 | A1 | 11/2004 | Britten | |
| 2005/0025729 | A1 | 2/2005 | Groteluschen et al. | |
| 2005/0054991 | A1 | 3/2005 | Tobyn | |
| 2005/0226903 | A1 | 10/2005 | Rogasch et al. | |
| 2005/0249774 | A1 | 11/2005 | Pauletti | |
| 2006/0018933 | A1 | 1/2006 | Vaya | |
| 2006/0018937 | A1 | 1/2006 | Friedman et al. | |
| 2006/0052353 | A1 | 3/2006 | Johnson | |

OTHER PUBLICATIONS

Natunola Castor 1023 Product Sheet; published Mar. 2010; downloaded Feb. 9, 2012.*

Wayback showing of Dr. Dan's CortiBalm product description, dated Dec. 31, 2009 and downloaded Sep. 2, 2013.*

Dr. Dan's CortiBalm product reviews dating May 2010 to present as shown at MakeupAlley.com; downloaded Sep. 2, 2013.*

PediaDerm package insert dated Nov. 2, 2009; downloaded Sep. 2, 2013.*

"International Search Report" for International Patent Application No. PCT/US11/01742 of Joel Schlessinger, MD, filed internationally on Oct. 12, 2011 (3 pages).

"Written Opinion of the International Searching Authority" for International Patent Application No. PCT/US11/01742 of Joel Schlessinger, MD, filed internationally on Oct. 12, 2011 (29 pages).

Fancol (R) VB, Elementis Specialty, PDS-Fancol VB pdf Mar. 2011 http://www.elementis.com/esweb/webproducts.nsf/alibydecid/18F2112739A91D158525776F004DDACA/$FILE/PDS-FANCOL%C2%AE%20VB.pdf (2 pages).

Natunola (R) Castor 1023, www.natunola.com, Mar. 2010 (Identified on the above International Search Report) (1 page).

Finsolv-TN, Innospec, www.innospec.com, Apr. 2010 (Identified on the above International Search Report) (3 pages).

U.S. Appl. No. 12/925,464, filed Oct. 23, 2010, Joel Schlessinger et al.

* cited by examiner

FIG. 13A
FIG. 13B
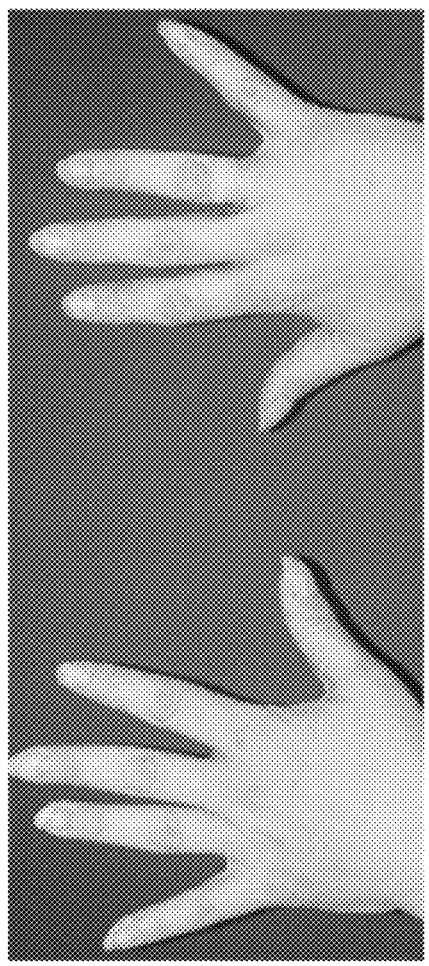
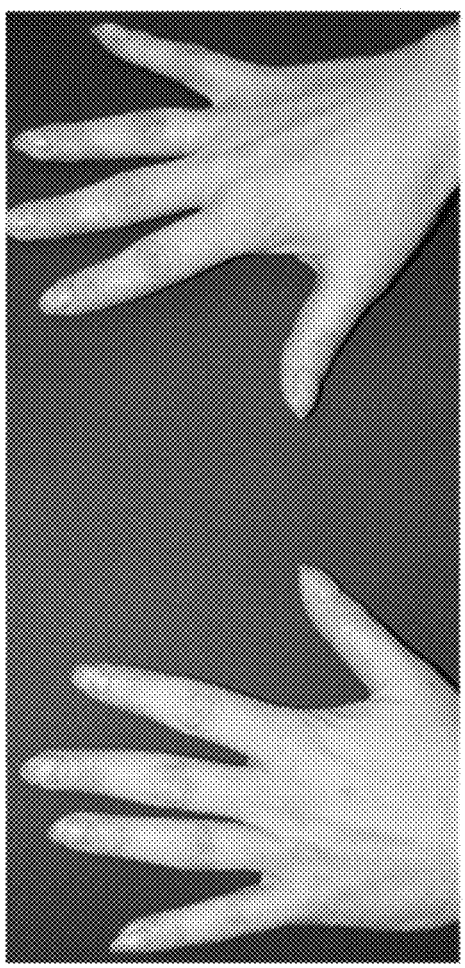

TOPICAL BASE AND ACTIVE AGENT-CONTAINING COMPOSITIONS, AND METHODS FOR IMPROVING AND TREATING SKIN

CROSS REFERENCE TO RELATED APPLICATIONS

This patent application is a continuation-in-part application of pending non-provisional patent application U.S. Ser. No. 12/925,464, filed on Oct. 23, 2010. This continuation-in-part patent application claims the benefit of priority to non-provisional patent application U.S. Ser. No. 12/925,464, filed on Oct. 23, 2010, which patent application is hereby incorporated into this continuation-in-part patent application in its entirety by reference herein, including all parts thereof.

BACKGROUND OF THE INVENTION

1. Field of the Invention

The present invention relates to novel topical base compositions having a unique combination of ingredients, and weight percents thereof, for use as effective carrier vehicles for one or a plurality of active agents that are to be applied topically to the skin of a human being or animal, such as hydrocortisone, in active-agent containing compositions.

The present invention also relates to novel active agent-containing compositions, such as those that include hydrocortisone (alone or in a combination with one or more other active ingredients), or one or more other active agents, for a topical application to the skin of a human being or animal having a unique combination of ingredients, and weight percents thereof, which have been determined to have many advantages in comparison with other topical active-agent containing compositions. For example, they penetrate one or more layers of, and tissues in, the skin, and have been determined to be extremely efficacious in promoting a repair, an improvement or a complete healing of a wide variety of different skin disorders, diseases and/or conditions, including inflammation (acting as an anti-inflammatory agent), deep within the layers and tissues of the skin, including the epidermis and epidermis.

The present invention further relates to methods for producing the above formulations, and methods for improving, repairing, healing or otherwise treating the skin of a mammal with respect to a wide variety of different disorders, diseases and/or conditions, such as those that are described herein, and/or causing the mammal's skin to feel soothed, softened and/or conditioned, by topically administering, or otherwise applying, effective amounts of the composition thereto.

2. Background

The skin of mammals, such as human beings and animals of all ages, and animals of all types, often becomes diseased, traumatized, inflamed, reddened, injured, irritated, damaged, deteriorated, cracked, itchy, severely dried, covered with a plurality of bumps and/or blisters, acne and/or insect bites, or otherwise wounded as a result of a wide variety of causes. These causes include, but are not limited to, physical injury, trauma, perforation, cutting, burning (by sun exposure, flame, hot objects and/or the like), blistering (from sun exposure, other burning, shoes and/or the like), chapping, bites (by insects, animals, human beings and/or the like), disease or disorder (poison ivy, poison oak, genital disease and/or the like), illness, microbes, exposure to chemicals, exposure to harsh environmental conditions (extreme hot or cold conditions, high winds, or the like), age, abuse, extreme dryness, and/or other factors.

In order to improve or promote a healing of the above (and other) types of skin problems in both human beings and animals, it is often necessary, or at least desirable, to employ one or more topical compositions for a topical application to the skin that include one or more active agents in a base having an ability to act as a carrier vehicle for the active agents when topically applied to the skin, such as a hydrocortisone-containing ointment or cream for topical application to the skin. However, very disadvantageously, many of the known topical skin compositions that contain hydrocortisone and/or other active agents do not penetrate the skin, or various layers thereof, or tissues present therein, but in contrast, are only designed to lay on top of the skin stratum corneum (the outermost layer of the epidermis, or external skin surface). As a result, these topical compositions often are not very efficacious, or at all efficacious, in repairing, improving or healing one or more skin disorders, diseases or adverse conditions, such as an inflammation or redness that extends deep within the various layers of, and tissues present in, the skin.

Moreover, very disadvantageously, many of the base formulations that are presently employed as carrier vehicles for topically applied active agents are very greasy and messy, often soiling the clothing of the user, are not convenient for use by consumers and/or are subject to deterioration under one or more adverse environmental conditions (i.e., they deteriorate), such as high temperatures. For example, the base formulations that are employed in some of the known and commercially-available rigid stick formulations for a topical application to the skin and/or lips crack in relatively cold temperatures and/or melt in relatively high temperatures, causing the product to become less useful or completely useless, and often extremely messy and a waste of money. Because many of these products include high quantities of "oily" and/or "fatty" types of substances, if such substances melt under conditions of relatively high heat, such as when they are left in a glove box of a vehicle during hot summer months, the oils and/or fats, which generally are not soluble in water or in aqueous-based cleaning agents, can be extremely difficult to remove from papers, clothing and similar types of items, upon which they may melt and/or spill when melted.

Moreover, most existing topical skin compositions have either a very thick feel, lacking cosmetic elegance and therefore decreasing compliance, or a thin feel, which may increase compliance, but decreases efficacy greatly because an ability to decrease transepidermal water loss (TEWL) is very important for any of these medications, and is often lacking therefrom.

There are very few, if any, topical skin medications including hydrocortisone (and/or other active ingredients) on the market that are present in a solid form, such as a stick, allowing a user to treat an area of skin disease that is very small, such as a size of a pinpoint, or very large, such as a plurality of square inches in diameter, and effectively seal the skin off from further damage, all the while decreasing transepidermal water loss (TEWL) and repairing or fully healing the skin. Additionally, those topical skin medications that include hydrocortisone usually have an undesirable "'tacky" feel to them, and have a very bitter taste and odor if applied to the mucosal areas of the lips, which is also very undesirable, and renders their efficacy less likely due to poor patient compliance. To date, none of the existing hydrocortisone balm lip formulations appear to have solved this problem of having a bitter taste. Additionally, none of these formulations have a relatively solid consistency, leaving them unlikely to repair, improve or heal the skin of a patient for long periods of time, as they come off of the skin easily.

Furthermore, none of the topical skin preparations including hydrocortisone in a stick formulation that are on the market have the directive of having one or two types of methods and/or sizes to apply to either large or small surfaces of the skin. For this reason, they are severely limited when it comes to the uses and applicability over various body surface areas. For example, if one likens this to another process, if one only had one size of a paint brush that was no larger than a toothbrush in size, the paint brush would limit the uses of this product. Interestingly, while hydrocortisone has been available for many years, and other formulations have attempted to apply it as a cream to the body, or even as an ointment, there have been no commercially-available products that combine a palatable and elegant form of it in a lip-based product as well as in a product that is suitable for larger body surfaces. None of the existing formulations appear to have a large body application methodology, as they only have a 'lip balm' size. They are not indicated for the body, and there is no inducement on any packaging or promotional material for the finger or hand cracks that occur in the drier times of the year or with various skin diseases.

Additionally, the topical skin products including hydrocortisone that have been marketed for over-the-counter treatments have typically been very limited as to treatment of significant skin disease, as they have been creams or ointments. These preparations typically have less penetration and less efficacy on adverse skin conditions, such as psoriasis and eczema, and therefore, generally have little or no healing or other effect on the skin of the majority of patients. As a result, none of these existing hydrocortisone products have any indication of usage for skin diseases other than chapped lips generally or chapped lips in patients with psoriasis or who are taking Accutane or Soriatane (i.e., drugs that cause chapped lips), or related efficacy.

In view of the above, it would be extremely beneficial to provide, and treat the skin of mammals having one or a plurality of skin conditions, disorders, diseases and/or the like, with a topical composition for application to the skin including one or more active agents, such as hydrocortisone, that: (i) penetrates one or a plurality of layers of the mammal's skin, including the epidermis and dermis, and the tissues therein, thereby exhibiting efficacious repair, complete healing and/or other beneficial actions in connection with a variety of different skin problems, such as eczema, psoriasis, dermatitis, seborrheic dermatitis or severe dryness, deep within the layers and/or tissues of the skin (rather than only resting on top of the outside of the outermost layer of the mammal's skin); (ii) has an ability to decrease or prevent transepidermal water loss (TEWL) from the skin and effectively partially or fully seal the skin off from further environmental and/or other damage; (iii) does not have an undesirable feel to the touch or skin of a mammal, such as a very thick, very thin or tacky (sticky) feel, but rather has a relatively smooth, non-tacky, non-sticky and desirable feel; (iv) has a pleasant or desirable taste and odor to a user when applied to mucosal areas of the lips (or elsewhere); (v) may be formed into a wide variety of sizes and/or shapes, or in multiple sizes and/or shapes, (vi) may be applied as a product over various different body surface areas of different sizes and/or types, such as a lip-based product for application to the lips and also as separate products that are suitable for topical application to larger body surfaces and, thus, permit a user to treat very small and/or very large areas of the skin (such as a pinpoint area and/or an area spanning one or a plurality of square inches or other shapes); (vii) is convenient and easy to administer for users; (viii) is safe and reliable for use by mammals; (ix) maintains its consistency, form and shape under relatively extreme environmental conditions, such as at relatively low temperatures, for example, on a ski slope, and at relatively high temperatures, for example, in a hot vehicle during the summer months; (x) is cosmetically elegant and physically appealing and desirable; (xi) promotes or otherwise enhances patient compliance; and (xii) is relatively inexpensive.

It would also be extremely beneficial to provide base compositions that have the above characteristics, and can properly function as carrier vehicles for one or more active agents to be applied topically to the skin of a human being or animal.

Description of Related Art

According to a Burt's Bees lip balm Internet web site, Burt's Bees lip balm, which is present in a tube, contains beeswax, *cocos nucifera* (coconut) oil, *helianthus annuus* (sunflower) seed oil, *mentha piperita* (peppermint) oil, lanolin, tocopherol, *rosmarinus officinalis* (rosemary) leaf extract, *glycine soja* (soybean) oil, canola oil, Tin: *cera alba* (beeswax, cire d'abeille), *prunus amygdalus dulcis* (sweet almond) oil, *mentha piperita* (peppermint) oil, lanolin, tocopherol, *rosmarinus officinalis* (rosemary) leaf extract, *glycine soja* (soybean) oil and canola oil (huile de colza).

According to a ChapStick® web site, ChapStick® contains seven natural ingredients that function as skin-conditioning agents or moisturizers, which remain on the surface of the skin. Some of these ingredients are also stated to prevent evaporation of water and protect lips from drying and chapping when exposed to wind or cold weather. The process of manufacturing ChapStick® is stated to be similar to following a recipe. A big blender is stated to mix the heated ingredients of ChapStick®. The color and flavor are added, and then the warm mixture is poured into containers.

Carmex is a brand of topical lip balm that is meant to improve or eliminate cold sores and soothe dry or chapped lips. It may be sold in jars, sticks and squeezable tubes. According to a Carmex Internet web site, traditional Carmex contains camphor, menthol, phenol, beeswax, cetyl esters, flavor, fragrance, lanolin, paraffin, petrolatum, salicylic acid and *theobroma cacao*(cocoa) seed butter.

According to a Blistex Internet web site, Blistex medicated lip balm (in the form of a hard stick), contains the active ingredients dimethicone (2.0%) (skin protectant), oxybenzone (2.5%) (sunscreen) and padimate O (6.6%) (sunscreen), as well as the other ingredients bees wax, camphor, cetyl alcohol, cetyl Palmitate, *euphorbia cerifera* (candelilla) wax, flavors, isopropyl Myristate, isopropyl Palmitate, isopropyl stearate, lanolin, lanolin oil, menthol, methylparaben, mineral oil, ozokerite, paraffin, petrolatum, polybutene, propylparaben, red 6 lake, *theobroma cacao* (cocoa) seed butter and titanium dioxide.

U.S. Pat. No. 5,662,993 describes stick formulations for topical delivery of water soluble and/or water insoluble agents, which may contain steroids, antibiotics, antifungals, antihistamines anti inflammatories or local anesthetics. The vehicles comprise a combination of waxes and oils and a surfactant in embodiments involving water soluble agents.

U.S. Pat. No. 6,228,351 describes a lip balm for treating cheilitis (painful dry inflamed lips) containing from 0.2% to 2.5% hydrocortisone in a base of beeswax mineral oil and petroleum jelly, wherein the amount of petroleum jelly is not more than that of the beeswax and mineral oil combined, and the amount of mineral oil is roughly equal to the amount of beeswax. In contrast with the compositions and base formulations of the present invention, the lip balms described by the '351 patent, which contain many different ingredients, and weight percents thereof, such as large quantities of petroleum jelly (from 40% to 50% by weight of the base), are used only upon the lips, and disadvantageously have an undesirable taste, which is typical of hydrocortisone-containing products (and tends to discourage, reduce or eliminate patient compliance). Further, as a result of its different ingredients, particularly the large amount of petroleum jelly, these lip balms have a very different consistency in comparison with the hydrocortisone-containing (and other) compositions of the present invention. They have a liquid or semi-liquid type of a feel to the touch (i.e., not a solid feel), and may be messy and/or sloppy for use by individuals, and to their clothing, jewelry and surrounding objects (papers, books, maps, sunglasses, seat or car and/or the like), particularly when present at high temperatures. Further, these lip balms are not indicated by the '351 patent for any skin malady or condition other than psoriasis, and have not been shown by the '351 patent to be efficacious for any such malady or condition.

Published U.S. Patent Application No. US 2004/0091539 A1 describes a solid stick topical composition containing a corticosteroid, petrolatum, wax, propyleneglycol and an emulsifier.

Published U.S. Patent Application No. US 2003/0232091 A1 describes a controlled release system for stabilizing retinol, retinol derivatives, and extracts containing retinol in cosmetic, dermatological, and pharmaceutical compositions.

Published U.S. Patent Application No. US 2004/0202725 A1 describes compositions for the treatment of pilosebaceous gland inflammations, especially of the hair follicle and its appendages, in particular of Acne Vulgaris and Folliculitis, comprising as active ingredient aluminum fluoride, or chemical compounds that finally release aluminum fluoride.

None of the patent documents or web sites that are identified above describe or suggest the unique base and active agent-containing formulations of the present invention, or the related production or application methods, or compositions having the advantages that are described herein.

SUMMARY OF THE INVENTION

It has been surprisingly and unexpectedly determined after a significant amount of experimentation and testing on human beings that base and active-agent containing compositions having the unique formulations that are described herein (i.e., a particular combination of ingredients, and particular weight percents thereof), when topically applied to the skin of a mammal, very advantageously: (i) penetrate one or a plurality of layers of the mammal's skin, including the epidermis and dermis, and the tissues therein, thereby exhibiting efficacious repair, complete healing and/or other beneficial actions in connection with a variety of different skin problems, such as eczema, psoriasis, dermatitis, seborrheic dermatitis, cracks, cuts, wounds, punctures, bumps, rashes, inflammation, severe dryness and the like, deep within the layers and/or tissues of the skin (rather than only resting on top of the outside of the outermost layer of the mammal's skin); (ii) have an ability to decrease or prevent transepidermal water loss (TEWL) from the skin and effectively partially or fully seal the skin off from further environmental and/or other damage; (iii) do not have an undesirable feel to the touch or skin of a mammal, such as a very thick, very thin or tacky (sticky) feel, but rather have a relatively smooth, non-tacky, non-sticky and desirable feel; (iv) have a pleasant or desirable taste and odor to a user when applied to mucosal areas of the lips (or elsewhere), or have no, or a minimal, bitter or other undesirable taste and/or odor (whether including one or more flavoring ingredients or not); (v) may be formed into a wide variety of sizes and/or shapes, or in multiple sizes and/or shapes, in a wide variety of different containers, such as non-squeezable or squeezable tubes, spray or non-spray cans, jars, pots, and the like; (vi) may be applied as a product over various different body surface areas of different sizes and/or types, such as a lip-based product for application to the lips, and also as separate products that are suitable for topical application to larger body surfaces and, thus, permit a user to treat very small and/or very large areas of the skin (such as a pinpoint area and/or an area spanning one or a plurality of square inches or other shapes); (vii) are convenient and easy to administer for users; (viii) are safe and reliable for users; (ix) maintain their consistency, form and shape under relatively extreme environmental conditions, such as at relatively low temperatures, for example, on a ski slope, and at relatively high temperatures, for example, in a hot vehicle during the summer months; (x) are cosmetically elegant and physically appealing and desirable; (xi) promote or otherwise enhances or encourages patient or user compliance; and/or (xii) are relatively inexpensive. Topical base and active agent-containing compositions within the present invention typically include each of the above benefits, and are improvements over known topical base and active agent-containing compositions, including those containing hydrocortisone.

When employed in the manner, and under the conditions, that are described herein, the base and active agent-containing compositions of the invention, which have specific formulations including a unique combination of ingredients, and weight percents thereof, have surprisingly and unexpectedly been determined via a significant amount of experimentation and testing on human beings to function extremely well together, providing topical skin compositions that are extremely efficacious for: (i) repairing, improving, partially or fully healing, or otherwise treating *a wide variety of different skin disorders, diseases, conditions, maladies, dryness and/or the like, of the skin of mammals, such as inflammation, redness, itching, bumps, blisters, cuts, punctures, other wounds, cracking, severe dryness, allergic reactions, insect bites, trauma, irritant dermatitis, contact dermatitis, seborrheic dermatitis, stasis dermatitis, perleche, psoriasis, eczema, eczema craquele, acne excoriee (a form or irritated and/or picked acne), allergies, other skin irritations, a variety of different skin complications resulting from acne, xerosis, disease related skin conditions and dryness from medications, such as isotretinoin, acitretin, lipid-lowering agents and/or the like; and/or (ii) causing the skin of a mammal to feel less painful, less irritated, less itchy, softened, soothed and/or conditioned, often with a 100% improvement, as is described in the experiments that are described herein. The hydrocortisone-containing skin balms of the present invention have been significantly tested experimentally with human beings and determined to be very effective, for example, on hand dermatitis, eczema, seborrheic dermatitis, cracks, cuts, punctures and severe dryness from lip conditions due to accutane usage, as is illustrated in the drawings included herein (FIGS. 2-17).

The base and active agent-containing compositions of the present invention exhibit benefits that are described above, and otherwise herein, generally to a significantly or far greater extent (for example, on a sale of from about 0% to about 100%) in comparison with other base or active agent-containing compositions, and typically do not exhibit any of the disadvantages that are discussed hereinabove in the Background of Invention section. Many other such compositions do not exhibit one or more of the above advantages at all, or to any significant extent. Thus, the base and active agent-containing compositions of the present invention are superior to, and a significant improvement of such compositions and base formulations as a result of their numerous benefits and advantages, and a significant advance in this art. They have advantages that overcome many or all of the shortcomings that are described herein of other topical skin base and active agent containing compositions, and are able to repair, improve and/or heal patients (or other users) having one or more of the various adverse skin conditions, disorders or diseases that are described herein, as well as many others.

The base and active agent-containing compositions of the invention are very different from any existing topical lip or skin balm (or other composition) because they include a unique combination of the ingredients Finsolv TN, Natunola Castor 1023, FANCOL VB and bees wax, as well as one or more optional ingredients, which together produce a preferably solid, firm, yet pliable, balm that has an ability to maintain its consistency, form and shape over time, and reduces, masks or eliminates the taste(s) and odor(s) of otherwise undesirably tasting ingredients, for example, the undesirable bitter taste of hydrocortisone.

Base

In one aspect, the present invention provides a topical base composition in a solid or semi-solid form for use as a carrier vehicle for one or a plurality of active agents, such as hydrocortisone, comprising FANCOL VB, Natunola Castor 1023, Finsolv TN and bees wax, each in amounts that are effective for collectively forming together a base composition in a sold or semi-solid form having an ability to function effectively as a topically-applied carrier vehicle for the active agents.

In another aspect, the present invention provides a topical base composition in a solid or semi-solid form for use as a carrier vehicle for one or a plurality of active agents, such as hydrocortisone, consisting of (or consisting essentially of) FANCOL VB, Natunola Castor 1023, Finsolv TN and bees wax, each in amounts that are effective for collectively forming together a base composition in a sold or semi-solid form having an ability to function effectively as a topically-applied carrier vehicle for the active agents.

In another aspect, the present invention provides a topical base composition in a solid or semi-solid form for use as a carrier vehicle for one or a plurality of active agents, such as hydrocortisone, comprising FANCOL VB, Natunola Castor 1023, Finsolv TN, bees wax, one or a plurality of plant or plant seed oils, one or a plurality of fatty alcohols, and one or a plurality of fats, each in combined amounts that are effective for collectively forming together a base composition in a sold or semi-solid form having an ability to function effectively as a topically-applied carrier vehicle for the active agents.

In still another aspect, the present invention provides a topical base composition in a solid or semi-solid form for use as a carrier vehicle for one or a plurality of active agents, such as hydrocortisone, consisting of (or consisting essentially of) FANCOL VB, Natunola Castor 1023, Finsolv TN, bees wax, one or a plurality of plant or plant seed oils, one or a plurality of fatty alcohols, and one or a plurality of fats, each in combined amounts that are effective for collectively forming together a base composition in a solid or semi-solid form having an ability to function effectively as a topically-applied carrier vehicle for the active agents.

In another aspect, the present invention provides a topical base composition in a solid or semi-solid form for use as a carrier vehicle for one or a plurality of active agents, such as hydrocortisone, comprising FANCOL VB, Natunola Castor 1023, Finsolv TN, bees wax, one or a plurality of plant or plant seed oils, one or a plurality of fatty alcohols, one or a plurality of fats, and one or a plurality of flavorings, each in combined amounts that are effective for collectively forming together a base composition in a sold or semi-solid form having an ability to function effectively as a topically-applied carrier vehicle for the active agents, and wherein the base composition does not have a bitter taste or odor, has no distinctive taste or odor or has a pleasant taste or odor, or both (even in the absence of any flavoring).

In yet another aspect, the present invention provides a topical base composition in a solid or semi-solid form for use as a carrier vehicle for one or a plurality of active agents, such as hydrocortisone, consisting of (or consisting essentially of) FANCOL VB, Natunola Castor 1023, Finsolv TN, bees wax, one or a plurality of plant or plant seed oils, one or a plurality of fatty alcohols, one or a plurality of fats, and one or a plurality of flavorings, each in combined amounts that are effective for collectively forming together a base composition in a sold or semi-solid form having an ability to function effectively as a topically-applied carrier vehicle for the active agents, and wherein the base composition does not have a bitter taste or odor, has no distinctive taste or odor or has a pleasant taste or odor, or both (even in the absence of any flavoring).

Original (Specific) Formulations

In another aspect, the present invention provides a topical base composition in a solid or semi-solid form for use as a carrier vehicle for one or a plurality of active agents, such as hydrocortisone, comprising:
 (a) FANCOL VB, wherein the FANCOL VB is present in the base composition in an amount ranging from about 9 to about 25 weight percent;
 (b) Natunola Castor 1023, wherein the Natunola Castor 1023 is present in the base composition in an amount ranging from about 16 to about 39 weight percent;
 (c) Finsolv TN, wherein the Finsolv TN is present in the base composition in an amount ranging from about 9 to about 25 weight percent;
 (d) bees wax, wherein the bees wax is present in the base composition in an amount ranging from about 18 to about 43 weight percent;
 (e) optionally, one or a plurality of plant oils or plant seed oils, wherein the plant or plant seed oils are present in the base composition in a combined amount ranging from about 0 to about 24 weight percent;
 (f) optionally, one or a plurality of fatty alcohols, wherein the fatty alcohols are present in the base composition in a combined amount ranging from about 0 to about 22 weight percent;
 (g) optionally, one or a plurality of fats, wherein the fats are present in the base composition in a combined amount ranging from about 0 to about 9 weight percent; and
 (h) optionally, one or a plurality of flavorings, wherein the flavorings are present in the base composition in a combined amount ranging from about 0 to about 3.5 weight percent;
wherein the base composition is in a sold or semi-solid form having an ability to function effectively as a topically-applied carrier vehicle for the active agents.

In still another aspect, the present invention provides a topical base composition in a solid or semi-solid form for use as a carrier vehicle for one or a plurality of active agents, such as hydrocortisone, consisting of (or consisting essentially of):
 (a) FANCOL VB, wherein the FANCOL VB is present in the base composition in an amount ranging from about 9 to about 25 weight percent;

(b) Natunola Castor 1023, wherein the Natunola Castor 1023 is present in the base composition in an amount ranging from about 16 to about 39 weight percent;
(c) Finsolv TN, wherein the Finsolv TN is present in the base composition in an amount ranging from about 9 to about 25 weight percent;
(d) bees wax, wherein the bees wax is present in the base composition in an amount ranging from about 18 to about 43 weight percent;
(e) optionally, one or a plurality of plant oils or plant seed oils, wherein the plant or plant seed oils are present in the base composition in a combined amount ranging from about 0 to about 24 weight percent;
(f) optionally, one or a plurality of fatty alcohols, wherein the fatty alcohols are present in the base composition in a combined amount ranging from about 0 to about 22 weight percent;
(g) optionally, one or a plurality of fats, wherein the fats are present in the base composition in a combined amount ranging from about 0 to about 9 weight percent; and
(h) optionally, one or a plurality of flavorings, wherein the flavorings are present in the base composition in a combined amount ranging from about 0 to about 3.5 weight percent;

wherein the base composition is in a sold or semi-solid form having an ability to function effectively as a topically-applied carrier vehicle for the active agents.

In another aspect, the present invention provides a topical base composition in a solid or semi-solid form for use as a carrier vehicle for one or a plurality of active agents, such as hydrocortisone, comprising:
(a) FANCOL VB, wherein the FANCOL VB is present in the base composition in an amount ranging from about 9 to about 13 weight percent;
(b) Natunola Castor 1023, wherein the Natunola Castor 1023 is present in the base composition in an amount ranging from about 16 to about 20 weight percent;
(c) Finsolv TN, wherein the Finsolv TN is present in the base composition in an amount ranging from about 9 to about 13 weight percent;
(d) bees wax, wherein the bees wax is present in the base composition in an amount ranging from about 18 to about 22 weight percent;
(e) one or more plant or plant seed oils, wherein the plant or plant seed oils are present in the base composition in a combined amount ranging from about 0.1 to about 24 weight percent;
(f) one or more fatty alcohols, wherein the fatty alcohols are present in the base composition in a combined amount ranging from about 0.1 to about 22 weight percent;
(g) one or more fats, wherein the fats are present in the base composition in a combined amount ranging from about 0.1 to about 9 weight percent; and
(h) optionally, one or a plurality of flavorings, wherein the flavorings are present in the base composition in an amount ranging from about 0 to about 3.5 weight percent;

wherein the base composition is in a sold or semi-solid form having an ability to function effectively as a topically-applied carrier vehicle for the active agents.

In still another aspect, the present invention provides a topical base composition in a solid or semi-solid form for use as a carrier vehicle for one or a plurality of active agents, such as hydrocortisone, consisting of (or consisting essentially of):

(a) FANCOL VB, wherein the FANCOL VB is present in the base composition in an amount ranging from about 9 to about 13 weight percent;
(b) Natunola Castor 1023, wherein the Natunola Castor 1023 is present in the base composition in an amount ranging from about 16 to about 20 weight percent;
(c) Finsolv TN, wherein the Finsolv TN is present in the base composition in an amount ranging from about 9 to about 13 weight percent;
(d) bees wax, wherein the bees wax is present in the base composition in an amount ranging from about 18 to about 22 weight percent;
(e) one or more plant or plant seed oils, wherein the plant or plant seed oils are present in the base composition in a combined amount ranging from about 0.1 to about 24 weight percent;
(f) one or more fatty alcohols, wherein the fatty alcohols are present in the base composition in a combined amount ranging from about 0.1 to about 22 weight percent;
(g) one or more fats, wherein the fats are present in the base composition in a combined amount ranging from about 0.1 to about 9 weight percent; and
(h) optionally, one or a plurality of flavorings, wherein the flavorings are present in the base composition in an amount ranging from about 0 to about 3.5 weight percent;

wherein the base composition is in a sold or semi-solid form having an ability to function effectively as a topically-applied carrier vehicle for the active agents.

Subsequent (Improved) Formulations

In another aspect, the present invention provides a topical base composition in a solid or semi-solid form for use as a carrier vehicle for one or a plurality of active agents, such as hydrocortisone, comprising:
(a) FANCOL VB, wherein the FANCOL VB is present in the base composition in an amount ranging from about 6 to about 25 weight percent;
(b) Natunola Castor 1023, wherein the Natunola Castor 1023 is present in the base composition in an amount ranging from about 5 to about 39 weight percent;
(c) Finsolv TN, wherein the Finsolv TN is present in the base composition in an amount ranging from about 9 to about 25 weight percent;
(d) bees wax, wherein the bees wax is present in the base composition in an amount ranging from about 6 to about 43 weight percent;
(e) optionally, one or a plurality of plant oils or plant seed oils, wherein the plant or plant seed oils are present in the base composition in a combined amount ranging from about 0 to about 38.5 (38.0 if one or more flavoring ingredients are present) weight percent;
(f) optionally, one or a plurality of fatty alcohols, wherein the fatty alcohols are present in the base composition in a combined amount ranging from about 0 to about 25 weight percent;
(g) optionally, one or a plurality of fats, wherein the fats are present in the base composition in a combined amount ranging from about 0 to about 12 weight percent; and
(h) optionally, one or a plurality of flavorings, wherein the flavorings are present in the base composition in a combined amount ranging from about 0 to about 3.5 weight percent;

wherein the base composition is in a sold or semi-solid form having an ability to function effectively as a topically-applied carrier vehicle for the active agents.

In still another aspect, the present invention provides a topical base composition in a solid or semi-solid form for use as a carrier vehicle for one or a plurality of active agents, such as hydrocortisone, consisting of (or consisting essentially of):
  (a) FANCOL VB, wherein the FANCOL VB is present in the base composition in an amount ranging from about 6 to about 25 weight percent;
  (b) Natunola Castor 1023, wherein the Natunola Castor 1023 is present in the base composition in an amount ranging from about 5 to about 39 weight percent;
  (c) Finsolv TN, wherein the Finsolv TN is present in the base composition in an amount ranging from about 9 to about 25 weight percent;
  (d) bees wax, wherein the bees wax is present in the base composition in an amount ranging from about 6 to about 43 weight percent;
  (e) optionally, one or a plurality of plant oils or plant seed oils, wherein the plant or plant seed oils are present in the base composition in a combined amount ranging from about 0 to about 38.5 (38.0 if one or more flavoring ingredients are present) weight percent;
  (f) optionally, one or a plurality of fatty alcohols, wherein the fatty alcohols are present in the base composition in a combined amount ranging from about 0 to about 25 weight percent;
  (g) optionally, one or a plurality of fats, wherein the fats are present in the base composition in a combined amount ranging from about 0 to about 12 weight percent; and
  (h) optionally, one or a plurality of flavorings, wherein the flavorings are present in the base composition in a combined amount ranging from about 0 to about 3.5 weight percent;
wherein the base composition is in a sold or semi-solid form having an ability to function effectively as a topically-applied carrier vehicle for the active agents.

Preferred subsequent (improved) base compositions of the invention include those that are described below.

Non-Flavored Base Compositions (Non-OTC and No Flavoring Ingredients)

In another aspect, the present invention provides a topical base composition in a solid or semi-solid form for use as a carrier vehicle for one or a plurality of active agents, such as hydrocortisone, comprising:
  (a) FANCOL VB, wherein the FANCOL VB is present in the base composition in an amount ranging from about 6 to about 16 weight percent;
  (b) Natunola Castor 1023, wherein the Natunola Castor 1023 is present in the base composition in an amount ranging from about 5 to about 15 weight percent;
  (c) Finsolv TN, wherein the Finsolv TN is present in the base composition in an amount ranging from about 10 to about 20 weight percent;
  (d) bees wax, wherein the bees wax is present in the base composition in an amount ranging from about 6 to about 16 weight percent;
  (e) one or a plurality of plant oils or plant seed oils, wherein the plant or plant seed oils are present in the base composition in a combined amount ranging from about 13.5 to about 38.5 weight percent;
  (f) one or a plurality of fatty alcohols, wherein the fatty alcohols are present in the base composition in a combined amount ranging from about 15 to about 25 weight percent; and
  (g) one or a plurality of fats, wherein the fats are present in the base composition in a combined amount ranging from about 2 to about 12 weight percent;
wherein the base composition is in a sold or semi-solid form having an ability to function effectively as a topically-applied carrier vehicle for the active agents.

In still another aspect, the present invention provides a topical base composition in a solid or semi-solid form for use as a carrier vehicle for one or a plurality of active agents, such as hydrocortisone, consisting of (or consisting essentially of):
  (a) FANCOL VB, wherein the FANCOL VB is present in the base composition in an amount ranging from about 6 to about 16 weight percent;
  (b) Natunola Castor 1023, wherein the Natunola Castor 1023 is present in the base composition in an amount ranging from about 5 to about 15 weight percent;
  (c) Finsolv TN, wherein the Finsolv TN is present in the base composition in an amount ranging from about 10 to about 20 weight percent;
  (d) bees wax, wherein the bees wax is present in the base composition in an amount ranging from about 6 to about 16 weight percent;
  (e) one or a plurality of plant oils or plant seed oils, wherein the plant or plant seed oils are present in the base composition in a combined amount ranging from about 13.5 to about 38.5 weight percent;
  (f) one or a plurality of fatty alcohols, wherein the fatty alcohols are present in the base composition in a combined amount ranging from about 15 to about 25 weight percent; and
  (g) one or a plurality of fats, wherein the fats are present in the base composition in a combined amount ranging from about 2 to about 12 weight percent;
wherein the base composition is in a sold or semi-solid form having an ability to function effectively as a topically-applied carrier vehicle for the active agents.

Flavored Base Compositions (Non-OTC, but Including Flavoring Ingredient(s))

In another aspect, the present invention provides a topical base composition in a solid or semi-solid form for use as a carrier vehicle for one or a plurality of active agents, such as hydrocortisone, comprising:
  (a) FANCOL VB, wherein the FANCOL VB is present in the base composition in an amount ranging from about 6 to about 16 weight percent;
  (b) Natunola Castor 1023, wherein the Natunola Castor 1023 is present in the base composition in an amount ranging from about 5 to about 15 weight percent;
  (c) Finsolv TN, wherein the Finsolv TN is present in the base composition in an amount ranging from about 10 to about 20 weight percent;
  (d) bees wax, wherein the bees wax is present in the base composition in an amount ranging from about 6 to about 16 weight percent;
  (e) one or a plurality of plant oils or plant seed oils, wherein the plant or plant seed oils are present in the base composition in a combined amount ranging from about 13.0 to about 38.0 weight percent;
  (f) one or a plurality of fatty alcohols, wherein the fatty alcohols are present in the base composition in a combined amount ranging from about 15 to about 25 weight percent;
  (g) one or a plurality of fats, wherein the fats are present in the base composition in a combined amount ranging from about 2 to about 12 weight percent; and (h) one or a plurality of flavorings, wherein the flavorings are present in the base composition in a combined amount ranging from about 0.1 to about 2.5 weight percent;

wherein the base composition is in a sold or semi-solid form having an ability to function effectively as a topically-applied carrier vehicle for the active agents.

In another aspect, the present invention provides a topical base composition in a solid or semi-solid form for use as a carrier vehicle for one or a plurality of active agents, such as hydrocortisone, consisting of (or consisting essentially of):

(a) FANCOL VB, wherein the FANCOL VB is present in the base composition in an amount ranging from about 6 to about 16 weight percent;

(b) Natunola Castor 1023, wherein the Natunola Castor 1023 is present in the base composition in an amount ranging from about 5 to about 15 weight percent;

(c) Finsolv TN, wherein the Finsolv TN is present in the base composition in an amount ranging from about 10 to about 20 weight percent;

(d) bees wax, wherein the bees wax is present in the base composition in an amount ranging from about 6 to about 16 weight percent;

(e) one or a plurality of plant oils or plant seed oils, wherein the plant or plant seed oils are present in the base composition in a combined amount ranging from about 13.0 to about 38.0 weight percent;

(f) one or a plurality of fatty alcohols, wherein the fatty alcohols are present in the base composition in a combined amount ranging from about 15 to about 25 weight percent;

(g) one or a plurality of fats, wherein the fats are present in the base composition in a combined amount ranging from about 2 to about 12 weight percent; and (h) one or a plurality of flavorings, wherein the flavorings are present in the base composition in a combined amount ranging from about 0.1 to about 2.5 weight percent;

wherein the base composition is in a sold or semi-solid form having an ability to function effectively as a topically-applied carrier vehicle for the active agents.

Active Agent Containing Composition

In another aspect, the present invention provides a composition for topical application to the skin of a mammal for repairing, improving or fully healing a skin disorder, disease or condition, or for causing the mammal's skin to experience a reduction in pain, soreness or itchiness, or an increase in soothing, softening or conditioning, or a combination thereof, comprising:

(a) one or a plurality of active agents, such as hydrocortisone, wherein the active agents are present in the composition in a combined amount that is effective for repairing, improving or healing the mammal's skin, or causing the mammal's skin to experience a reduction in pain, soreness or itchiness, or an increase in soothing, softening or conditioning, or a combination thereof, after a topical application of the composition to the mammal's skin; and (b) a base composition, wherein the base composition is present in the composition in an amount that is effective for permitting the base composition to function effectively as a carrier vehicle for the active agents when topically applied to the mammal's skin, and wherein the base composition includes FANCOL VB, Natunola Castor 1023, Finsolv TN and bees wax, each in amounts that are effective for collectively forming together the base composition in a sold or semi-solid form.

In yet another aspect, the present invention provides a composition for topical application to the skin of a mammal for repairing, improving or fully healing a skin disorder, disease or condition, or for causing the mammal's skin to experience a reduction in pain, soreness or itchiness, or an increase in soothing, softening or conditioning, or a combination thereof, consisting of (or consisting essentially of):

(a) one or a plurality of active agents, such as hydrocortisone, wherein the active agents are present in the composition in a combined amount that is effective for repairing, improving or healing the mammal's skin, or causing the mammal's skin to experience a reduction in pain, soreness or itchiness, or an increase in soothing, softening or conditioning, or a combination thereof, after a topical application of the composition to the mammal's skin; and (b) a base composition, wherein the base composition is present in the composition in an amount that is effective for permitting the base composition to function effectively as a carrier vehicle for the active agents when topically applied to the mammal's skin, and wherein the base composition includes FANCOL VB, Natunola Castor 1023, Finsolv TN and bees wax, each in amounts that are effective for collectively forming together the base composition in a sold or semi-solid form.

In another aspect, the present invention provides a composition for topical application to the skin of a mammal for repairing, improving or fully healing a skin disorder, disease or condition, or for causing the mammal's skin to experience a reduction in pain, soreness or itchiness, or an increase in soothing, softening or conditioning, or a combination thereof, comprising:

(a) one or a plurality of active agents, such as hydrocortisone, wherein the active agents are present in the composition in a combined amount that is effective for repairing, improving or healing the mammal's skin, or causing the mammal's skin to experience a reduction in pain, soreness or itchiness, or an increase in soothing, softening or conditioning, or a combination thereof, after a topical application of the composition to the mammal's skin; and (b) a base composition, wherein the base composition is present in the composition in an amount that is effective for permitting the base composition to function effectively as a carrier vehicle for the active agents when topically applied to the mammal's skin, and wherein the base composition includes FANCOL VB, Natunola Castor 1023, Finsolv TN, bees wax, one or a plurality of plant or plant seed oils, one or a plurality of fatty alcohols, and one or a plurality of fats, each in combined amounts that are effective for collectively forming together a base composition in a sold or semi-solid form.

In still another aspect, the present invention provides a composition for topical application to the skin of a mammal for repairing, improving or fully healing a skin disorder, disease or condition, or for causing the mammal's skin to experience a reduction in pain, soreness or itchiness, or an increase in soothing, softening or conditioning, or a combination thereof, consisting of (or consisting essentially of):

(a) one or a plurality of active agents, such as hydrocortisone, wherein the active agents are present in the composition in a combined amount that is effective for repairing, improving or healing the mammal's skin, or causing the mammal's skin to experience a reduction in pain, soreness or itchiness, or an increase in soothing, softening or conditioning, or a combination thereof, after a topical application of the composition to the mammal's skin; and (b) a base composition, wherein the base composition is present in the composition in an amount that is effective for permitting the base composition to function effectively as a carrier vehicle for the active agents when topically applied to the mammal's skin, and wherein the base composition includes FANCOL VB, Natunola Castor 1023, Finsolv TN, bees wax, one or a plurality of plant or plant seed oils, one or a plurality of fatty alcohols, and one or a plurality of fats, each in combined amounts that are effective for collectively forming together a base composition in a sold or semi-solid form.

In another aspect, the present invention provides a composition for topical application to the skin of a mammal for repairing, improving or fully healing a skin disorder, disease or condition, or for causing the mammal's skin to experience a reduction in pain, soreness or itchiness, or an increase in soothing, softening or conditioning, or a combination thereof, comprising:

(a) one or a plurality of active agents, such as hydrocortisone, wherein the active agents are present in the composition in a combined amount that is effective for repairing, improving or healing the mammal's skin, or causing the mammal's skin to experience a reduction in pain, soreness or itchiness, or an increase in soothing, softening or conditioning, or a combination thereof, after a topical application of the composition to the mammal's skin; and (b) a base composition, wherein the base composition is present in the composition in an amount that is effective for permitting the base composition to function effectively as a carrier vehicle for the active agents when topically applied to the mammal's skin, and wherein the base composition includes FANCOL VB, Natunola Castor 1023, Finsolv TN, bees wax, one or a plurality of plant or plant seed oils, one or a plurality of fatty alcohols, one or a plurality of fats, and one or a plurality of flavorings, each in combined amounts that are effective for collectively forming together a base composition in a sold or semi-solid form, and wherein the base composition does not have a bitter taste or odor, has no distinctive taste or odor or has a pleasant taste or odor, or both.

In yet aspect, the present invention provides a composition for topical application to the skin of a mammal for repairing, improving or fully healing a skin disorder, disease or condition, or for causing the mammal's skin to experience a reduction in pain, soreness or itchiness, or an increase in soothing, softening or conditioning, or a combination thereof, consisting of (or consisting essentially of):

(a) one or a plurality of active agents, such as hydrocortisone, wherein the active agents are present in the composition in a combined amount that is effective for repairing, improving or healing the mammal's skin, or causing the mammal's skin to experience a reduction in pain, soreness or itchiness, or an increase in soothing, softening or conditioning, or a combination thereof, after a topical application of the composition to the mammal's skin; and (b) a base composition, wherein the base composition is present in the composition in an amount that is effective for permitting the base composition to function effectively as a carrier vehicle for the active agents when topically applied to the mammal's skin, and wherein the base composition includes FANCOL VB, Natunola Castor 1023, Finsolv TN, bees wax, one or a plurality of plant or plant seed oils, one or a plurality of fatty alcohols, one or a plurality of fats, and one or a plurality of flavorings, each in combined amounts that are effective for collectively forming together a base composition in a sold or semi-solid form, and wherein the base composition does not have a bitter taste or odor, has no distinctive taste or odor or has a pleasant taste or odor, or both.

Original (Specific) Formulations

In another aspect, the present invention provides a composition for topical application to the skin of a mammal for repairing, improving or fully healing a skin disorder, disease or condition, or for causing the mammal's skin to experience a reduction in pain, soreness or itchiness, or an increase in soothing, softening or conditioning, or a combination thereof, comprising:

(a) one or a plurality of active agents, such as hydrocortisone, wherein the active agents are present in the composition in a combined amount ranging from about 0.1 to about 5 weight percent; and (b) a base composition, wherein the base composition is present in the composition in an amount ranging from about 95 to about 99.9 weight percent, and wherein the base composition includes:
  (1) FANCOL VB, wherein the FANCOL VB is present in the base composition in an amount ranging from about 9 to about 25 weight percent;
  (2) Natunola Castor 1023, wherein the Natunola Castor 1023 is present in the base composition in an amount ranging from about 16 to about 39 weight percent;
  (3) Finsolv TN, wherein the Finsolv TN is present in the base composition in an amount ranging from about 9 to about 25 weight percent;
  (4) bees wax, wherein the bees wax is present in the base composition in an amount ranging from about 18 to about 43 weight percent;
  (5) optionally, one or a plurality of plant oils or plant seed oils, wherein the plant or plant seed oils are present in the base composition in a combined amount ranging from about 0 to about 24 weight percent;
  (6) optionally, one or a plurality of fatty alcohols, wherein the fatty alcohols are present in the base composition in a combined amount ranging from about 0 to about 22 weight percent;
  (7) optionally, one or a plurality of fats, wherein the fats are present in the base composition in a combined amount ranging from about 0 to about 9 weight percent; and
  (8) optionally, one or a plurality of flavorings, wherein the flavorings are present in the base composition in a combined amount ranging from about 0 to about 3.5 weight percent;
wherein the composition is in a sold or semi-solid form.

In still another aspect, the present invention provides a composition for topical application to the skin of a mammal for repairing, improving or fully healing a skin disorder, disease or condition, or for causing the mammal's skin to experience a reduction in pain, soreness or itchiness, or an increase in soothing, softening or conditioning, or a combination thereof, consisting of (or consisting essentially of):

(a) one or a plurality of active agents, such as hydrocortisone, wherein the active agents are present in the composition in a combined amount ranging from about 0.1 to about 5 weight percent; and (b) a base composition, wherein the base composition is present in the composition in an amount ranging from about 95 to about 99.9 weight percent, and wherein the base composition includes:
  (1) FANCOL VB, wherein the FANCOL VB is present in the base composition in an amount ranging from about 9 to about 25 weight percent;
  (2) Natunola Castor 1023, wherein the Natunola Castor 1023 is present in the base composition in an amount ranging from about 16 to about 39 weight percent;
  (3) Finsolv TN, wherein the Finsolv TN is present in the base composition in an amount ranging from about 9 to about 25 weight percent;
  (4) bees wax, wherein the bees wax is present in the base composition in an amount ranging from about 18 to about 43 weight percent;
  (5) optionally, one or a plurality of plant oils or plant seed oils, wherein the plant or plant seed oils are present in the base composition in a combined amount ranging from about 0 to about 24 weight percent;
  (6) optionally, one or a plurality of fatty alcohols, wherein the fatty alcohols are present in the base composition in a combined amount ranging from about 0 to about 22 weight percent;
  (7) optionally, one or a plurality of fats, wherein the fats are present in the base composition in a combined amount ranging from about 0 to about 9 weight percent; and
  (8) optionally, one or a plurality of flavorings, wherein the flavorings are present in the base composition in a combined amount ranging from about 0 to about 3.5 weight percent;
wherein the composition is in a sold or semi-solid form.

In another aspect, the present invention provides a composition for topical application to the skin of a mammal for repairing, improving or fully healing a skin disorder, disease or condition, or for causing the mammal's skin to experience a reduction in pain, soreness or itchiness, or an increase in soothing, softening or conditioning, or a combination thereof, comprising:
  (a) one or a plurality of active agents, such as hydrocortisone, wherein the active agents are present in the composition in a combined amount ranging from about 0.1 to about 5 weight percent; and
  (b) a base composition, wherein the base composition is present in the composition in an amount ranging from about 95 to about 99.9 weight percent, and wherein the base composition includes:
    (1) FANCOL VB, wherein the FANCOL VB is present in the base composition in an amount ranging from about 9 to about 13 weight percent;
    (2) Natunola Castor 1023, wherein the Natunola Castor 1023 is present in the base composition in an amount ranging from about 16 to about 20 weight percent;
    (3) Finsolv TN, wherein the Finsolv TN is present in the base composition in an amount ranging from about 9 to about 13 weight percent;
    (4) bees wax, wherein the bees wax is present in the base composition in an amount ranging from about 18 to about 22 weight percent;
    (5) one or more plant or plant seed oils, wherein the plant or plant seed oils are present in the base composition in a combined amount ranging from about 0.1 to about 24 weight percent;
    (6) one or more fatty alcohols, wherein the fatty alcohols are present in the base composition in a combined amount ranging from about 0.1 to about 22 weight percent;
    (7) one or more fats, wherein the fats are present in the base composition in a combined amount ranging from about 0.1 to about 9 weight percent; and
    (8) optionally, one or a plurality of flavorings, wherein the flavorings are present in the base composition in an amount ranging from about 0 to about 3.5 weight percent;
wherein the composition is in a sold or semi-solid form.

In another aspect, the present invention provides a composition for topical application to the skin of a mammal for repairing, improving or fully healing a skin disorder, disease or condition, or for causing the mammal's skin to experience a reduction in pain, soreness or itchiness, or an increase in soothing, softening or conditioning, or a combination thereof, consisting of (or consisting essentially of):
  (a) one or a plurality of active agents, such as hydrocortisone, wherein the active agents are present in the composition in a combined amount ranging from about 0.1 to about 5 weight percent; and
  (b) a base composition, wherein the base composition is present in the composition in an amount ranging from about 95 to about 99.9 weight percent, and wherein the base composition includes:
    (1) FANCOL VB, wherein the FANCOL VB is present in the base composition in an amount ranging from about 9 to about 13 weight percent;
    (2) Natunola Castor 1023, wherein the Natunola Castor 1023 is present in the base composition in an amount ranging from about 16 to about 20 weight percent;
    (3) Finsolv TN, wherein the Finsolv TN is present in the base composition in an amount ranging from about 9 to about 13 weight percent;
    (4) bees wax, wherein the bees wax is present in the base composition in an amount ranging from about 18 to about 22 weight percent;
    (5) one or more plant or plant seed oils, wherein the plant or plant seed oils are present in the base composition in a combined amount ranging from about 0.1 to about 24 weight percent;
    (6) one or more fatty alcohols, wherein the fatty alcohols are present in the base composition in a combined amount ranging from about 0.1 to about 22 weight percent;
    (7) one or more fats, wherein the fats are present in the base composition in a combined amount ranging from about 0.1 to about 9 weight percent; and
    (8) optionally, one or a plurality of flavorings, wherein the flavorings are present in the base composition in an amount ranging from about 0 to about 3.5 weight percent;
wherein the composition is in a sold or semi-solid form.

Subsequent (Improved) Formulations

In another aspect, the present invention provides a composition for topical application to the skin of a mammal for repairing, improving or fully healing a skin disorder, disease or condition, or for causing the mammal's skin to experience a reduction in pain, soreness or itchiness, or an increase in soothing, softening or conditioning, or a combination thereof, comprising:

(a) one or a plurality of active agents, such as hydrocortisone, wherein the active agents are present in the composition in a combined amount ranging from about 0.1 to about 5 weight percent;
(b) FANCOL VB, wherein the FANCOL VB is present in the composition in an amount ranging from about 6 to about 25 weight percent;
(c) Natunola Castor 1023, wherein the Natunola Castor 1023 is present in the composition in an amount ranging from about 5 to about 39 weight percent;
(d) Finsolv TN, wherein the Finsolv TN is present in the composition in an amount ranging from about 9 to about 25 weight percent;
(e) bees wax, wherein the bees wax is present in the composition in an amount ranging from about 6 to about 43 weight percent;
(f) optionally, one or a plurality of plant oils or plant seed oils, wherein the plant or plant seed oils are present in the composition in a combined amount ranging from about 0 to about 37.0 (37.5 if no flavoring ingredient is present) weight percent;
(g) optionally, one or a plurality of fatty alcohols, wherein the fatty alcohols are present in the composition in a combined amount ranging from about 0 to about 25 weight percent;
(h) optionally, one or a plurality of fats, wherein the fats are present in the composition in a combined amount ranging from about 0 to about 12 weight percent; and
(i) optionally, one or a plurality of flavorings, wherein the flavorings are present in the base composition in a combined amount ranging from about 0 to about 3.5 weight percent;
wherein the composition is in a sold or semi-solid form.

Preferred subsequent (improved) active agent-containing compositions of the invention include those that are described below.

Non-Flavored Compositions Including Active Agent(s) (OTC and No Flavor)

In another aspect, the present invention provides a composition for topical application to the skin of a mammal for repairing, improving or fully healing a skin disorder, disease or condition, or for causing the mammal's skin to experience a reduction in pain, soreness or itchiness, or an increase in soothing, softening or conditioning, or a combination thereof, comprising:
(a) one or a plurality of active agents, such as hydrocortisone, wherein the active agents are present in the composition in a combined amount ranging from about 0.1 to about 3 weight percent;
(b) FANCOL VB, wherein the FANCOL VB is present in the composition in an amount ranging from about 6 to about 16 weight percent;
(c) Natunola Castor 1023, wherein the Natunola Castor 1023 is present in the composition in an amount ranging from about 5 to about 15 weight percent;
(d) Finsolv TN, wherein the Finsolv TN is present in the composition in an amount ranging from about 10 to about 20 weight percent;
(e) bees wax, wherein the bees wax is present in the composition in an amount ranging from about 6 to about 16 weight percent;
(f) one or a plurality of plant oils or plant seed oils, wherein the plant or plant seed oils are present in the composition in a combined amount ranging from about 12.5 to about 37.5 weight percent;
(g) one or a plurality of fatty alcohols, wherein the fatty alcohols are present in the composition in a combined amount ranging from about 15 to about 25 weight percent; and
(h) one or a plurality of fats, wherein the fats are present in the composition in a combined amount ranging from about 2 to about 12 weight percent;
wherein the composition is in a sold or semi-solid form.

In still another aspect, the present invention provides a composition for topical application to the skin of a mammal for repairing, improving or fully healing a skin disorder, disease or condition, or for causing the mammal's skin to experience a reduction in pain, soreness or itchiness, or an increase in soothing, softening or conditioning, or a combination thereof, consisting of (or consisting essentially of):
(a) one or a plurality of active agents, such as hydrocortisone, wherein the active agents are present in the composition in a combined amount ranging from about 0.1 to about 3 weight percent;
(b) FANCOL VB, wherein the FANCOL VB is present in the composition in an amount ranging from about 6 to about 16 weight percent;
(c) Natunola Castor 1023, wherein the Natunola Castor 1023 is present in the composition in an amount ranging from about 5 to about 15 weight percent;
(d) Finsolv TN, wherein the Finsolv TN is present in the composition in an amount ranging from about 10 to about 20 weight percent;
(e) bees wax, wherein the bees wax is present in the composition in an amount ranging from about 6 to about 16 weight percent;
(f) one or a plurality of plant oils or plant seed oils, wherein the plant or plant seed oils are present in the composition in a combined amount ranging from about 12.5 to about 37.5 weight percent;
(g) one or a plurality of fatty alcohols, wherein the fatty alcohols are present in the composition in a combined amount ranging from about 15 to about 25 weight percent; and
(h) one or a plurality of fats, wherein the fats are present in the composition in a combined amount ranging from about 2 to about 12 weight percent;
wherein the composition is in a sold or semi-solid form.

Flavored Compositions Including Active Agent(s) (OTC and Including Flavoring)

In another aspect, the present invention provides a composition for topical application to the skin of a mammal for repairing, improving or fully healing a skin disorder, disease or condition, or for causing the mammal's skin to experience a reduction in pain, soreness or itchiness, or an increase in soothing, softening or conditioning, or a combination thereof, comprising:
(a) one or a plurality of active agents, such as hydrocortisone, wherein the active agents are present in the composition in a combined amount ranging from about 0.1 to about 3 weight percent;
(b) FANCOL VB, wherein the FANCOL VB is present in the composition in an amount ranging from about 6 to about 16 weight percent;
(c) Natunola Castor 1023, wherein the Natunola Castor 1023 is present in the composition in an amount ranging from about 5 to about 15 weight percent;
(d) Finsolv TN, wherein the Finsolv TN is present in the composition in an amount ranging from about 10 to about 20 weight percent;

(e) bees wax, wherein the bees wax is present in the composition in an amount ranging from about 6 to about 16 weight percent;
(f) one or a plurality of plant oils or plant seed oils, wherein the plant or plant seed oils are present in the composition in a combined amount ranging from about 12.0 to about 37.0 weight percent;
(g) one or a plurality of fatty alcohols, wherein the fatty alcohols are present in the composition in a combined amount ranging from about 15 to about 25 weight percent;
(h) one or a plurality of fats, wherein the fats are present in the composition in a combined amount ranging from about 2 to about 12 weight percent; and
(i) one or a plurality of flavorings, where the flavorings are present in the composition in a combined amount ranging from about 0.1 to about 2.5 weight percent;
wherein the composition is in a sold or semi-solid form.

In another aspect, the present invention provides a composition for topical application to the skin of a mammal for repairing, improving or fully healing a skin disorder, disease or condition, or for causing the mammal's skin to experience a reduction in pain, soreness or itchiness, or an increase in soothing, softening or conditioning, or a combination thereof, consisting of (or consisting essentially of):
(a) one or a plurality of active agents, such as hydrocortisone, wherein the active agents are present in the composition in a combined amount ranging from about 0.1 to about 3 weight percent;
(b) FANCOL VB, wherein the FANCOL VB is present in the composition in an amount ranging from about 6 to about 16 weight percent;
(c) Natunola Castor 1023, wherein the Natunola Castor 1023 is present in the composition in an amount ranging from about 5 to about 15 weight percent;
(d) Finsolv TN, wherein the Finsolv TN is present in the composition in an amount ranging from about 10 to about 20 weight percent;
(e) bees wax, wherein the bees wax is present in the composition in an amount ranging from about 6 to about 16 weight percent;
(f) one or a plurality of plant oils or plant seed oils, wherein the plant or plant seed oils are present in the composition in a combined amount ranging from about 12.0 to about 37.0 weight percent;
(g) one or a plurality of fatty alcohols, wherein the fatty alcohols are present in the composition in a combined amount ranging from about 15 to about 25 weight percent;
(h) one or a plurality of fats, wherein the fats are present in the composition in a combined amount ranging from about 2 to about 12 weight percent; and
(i) one or a plurality of flavorings, where the flavorings are present in the composition in a combined amount ranging from about 0.1 to about 2.5 weight percent;
wherein the composition is in a sold or semi-solid form.

Method of Treatment

In still another aspect, the present invention provides a method for repairing, improving or fully healing a skin disorder, disease or condition of a mammal, or for causing the mammal's skin to experience a reduction in pain, soreness or itchiness, or an increase in soothing, softening or conditioning, or a combination thereof, comprising topically applying to the mammal's skin on a regular basis at least one or two applications of one of the above compositions, wherein the amount of the composition that is applied to the skin of the mammal is an amount that is effective for repairing, improving or fully healing a skin disorder, disease or condition of the mammal, or for causing the mammal's skin to experience a reduction in pain, soreness or itchiness, or an increase in soothing, softening or conditioning, or a combination thereof, and wherein the temperature of the composition is optionally elevated to a temperature above ambient temperature prior to topically applying the composition to the mammal's skin.

In still another aspect, the present invention provides a method for repairing, improving or fully healing a skin disorder, disease or condition of a mammal, or for causing the mammal's skin to experience a reduction in pain, soreness or itchiness, or an increase in soothing, softening or conditioning, or a combination thereof, consisting of (or consisting essentially of) topically applying to the mammal's skin on a regular basis at least one or two applications of one of the above compositions, wherein the amount of the composition that is applied to the skin of the mammal is an amount that is effective for repairing, improving or fully healing a skin disorder, disease or condition of the mammal, or for causing the mammal's skin to experience a reduction in pain, soreness or itchiness, or an increase in soothing, softening or conditioning, or a combination thereof.

Methods of Production

Original (Specific) Formulations

In still another aspect, the present invention provides a method for producing one of the above compositions in a solid or semi-solid form comprising the following steps in any suitable order:
(a) optionally, heating a combined amount of one or a plurality of plant oils that are sufficient, in combination with one or more other ingredients, for producing a composition in a solid or semi-solid form to a temperature, and for a period of time, that are effective for evenly heating the plant oil(s);
(b) adding an amount of FANCOL VB that is sufficient, in a combination with one or more other method ingredients, for producing a composition in a solid or semi-solid form to any plant oils heated in step (a), and heating the FANCOL VB at a temperature, and for a period of time, that are effective for evenly heating the FANCOL VB, and for dissolving the FANCOL VB in any such plant oils;
(c) adding an amount of Natunola Castor 1023 that is sufficient, in a combination with one or more other method ingredients, for producing a composition in a solid or semi-solid form to the product of step (b), and heating the Natunola Castor 1023 at a temperature, and for a period of time, that are effective for dissolving the Natunola Castor 1023 in such product;
(d) adding an amount of bees wax that is sufficient, in a combination with one or more other method ingredients, for producing a composition in a solid or semi-solid form to the product of step (c), and heating the bees wax at a temperature, and for a period of time, that are effective for dissolving the bees wax in such product;
(e) optionally, adding a combined amount of one or a plurality of fatty alcohols that are sufficient, in a combination with one or more other method ingredients, for producing a composition in a solid or semi-solid form to the product of step (d), and heating the fatty alcohols at a temperature, and for a period of time, that are effective for dissolving the fatty alcohols in such product;
(f) optionally, adding a combined amount of one or a plurality of fats that are sufficient for producing, in a combination with one or more other method ingredients, a composition in a solid or semi-solid form to the product of step (d) or step (e), and heating the fats at a temperature, and for a period of time, that are effective for dissolving the fats in such product;

(g) adding an amount of Finsolv TN that is sufficient, in a combination with one or more other method ingredients, for producing a composition in a solid or semi-solid form to the product of step (d), (e) or (f), and heating the Finsolv TN at a temperature, and for a period of time, that are effective for dissolving the Finsolv TN in such product;

(h) cooling the mixture of step (g) to a temperature that permits one or a plurality of active ingredients to be mixed therewith out significantly reducing the activities of the active ingredients, or rending them inactive;

(i) mixing a combined amount of one or a plurality of active ingredients that is sufficient, when present in a base composition in solid or semi-solid form, for repairing, improving or healing a skin disorder, disease or condition of a mammal, or for causing the mammal's skin to experience a reduction in pain, soreness or itchiness, or an increase in soothing, softening or conditioning, or a combination thereof, with the product of step (h) at a temperature, and for a period of time, that is sufficient for dissolving the active ingredients in such product;

(j) optionally, cooling the mixture of step (i) to a temperature that permits one or a plurality of flavorings to be mixed therewith out significantly reducing the flavor of the flavorings, or rending them flavorless;

(k) optionally, mixing a combined amount of one or a plurality of flavorings that is sufficient, when present in the composition, for providing the composition with a desirable or distinct flavor, or for partially or fully masking one or more bitter or undesirable flavors present therein, or a combination thereof, with the product of step (i) or (j) at a temperature, and for a period of time, that is sufficient for uniformly distributing the flavorings throughout such product;

(l) optionally, determining the concentration of the active ingredients in the mixture of step (i), (j) or (k); and (m) optionally, pouring or transferring the product of step (i), (j), (k) or (l) into one or a plurality of molds and allowing the product to harden, set or solidify therein;

wherein the composition is in a solid or semi-solid form.

Subsequent (Improved) Formulations

Preferred subsequent (improved) methods for producing preferred base and active agent-containing compositions of the invention include those that are described below.

Non-Flavored Base Compositions (Non-OTC and No Flavor)

In another aspect, the present invention provides a method for producing a topical base composition that does not include a flavoring ingredient or an active agent in a solid or semi-solid form comprising the following steps in any suitable order:

(a) heating one or a plurality of plant oils in a combined amount that is sufficient, in combination with one or more other ingredients, for producing a composition in a solid or semi-solid form to a temperature, and for a period of time, that are effective for evenly heating the plant oil(s), with an amount of mixing as may be required, for example, from about 75° C. to about 85° C.;

(b) adding an amount of FANCOL VB that is sufficient, in a combination with one or more other method ingredients, for producing a composition in a solid or semi-solid form to any plant oils heated in step (a), and heating the FANCOL VB at a temperature, and for a period of time, that are effective for evenly heating the FANCOL VB, and for dissolving the FANCOL VB in any such plant oils, with an amount of mixing as is required, for example, from about 75° C. to about 85° C.;

(c) adding an amount of bees wax that is sufficient, in a combination with one or more other method ingredients, for producing a composition in a solid or semi-solid form to the product of step (b), and heating the bees wax at a temperature, and for a period of time, that are effective for dissolving the bees wax in such product, with an amount of mixing as is required, for example, from about 75° C. to about 85° C.;

(d) adding one or a plurality of fatty alcohols in a combined amount that is sufficient, in a combination with one or more other method ingredients, for producing a composition in a solid or semi-solid form to the product of step (c), and heating the fatty alcohols at a temperature, and for a period of time, that are effective for dissolving the fatty alcohols in such product, with an amount of mixing as is required, for example, from about 75° C. to about 85° C.;

(e) adding one or a plurality of fats in a combined amount that is sufficient for producing, in a combination with one or more other method ingredients, a composition in a solid or semi-solid form to the product of step (d), and heating the fats at a temperature, and for a period of time, that are effective for dissolving the fats in such product, with an amount of mixing as is required, for example, from about 75° C. to about 85° C.;

(f) adding an amount of Finsolv TN that is sufficient, in a combination with one or more other method ingredients, for producing a composition in a solid or semi-solid form to the product of step (e), and heating the Finsolv TN at a temperature, and for a period of time, that are effective for dissolving the Finsolv TN in such product, with an amount of mixing as is required, for example, from about 75° C. to about 85° C.;

(g) adding an amount of Natunola Castor 1023 that is sufficient, in a combination with one or more other method ingredients, for producing a composition in a solid or semi-solid form to the product of step (f), and heating the Natunola Castor 1023 at a temperature, and for a period of time, that are effective for dissolving the Natunola Castor 1023 in such product, with an amount of mixing as is required, for example, from about 75° C. to about 85° C. for a period of time ranging from about 1 hour to about 1.5 hours; and (h) optionally, pouring or transferring the product of step (g) into one or a plurality of molds and allowing the product to partially or fully harden, set or solidify therein;

wherein the composition is in a solid or semi-solid form.

Flavored Base Compositions (Non-OTC, but Including Flavoring)

In another aspect, the present invention provides a method for producing a topical base composition that includes a flavoring ingredient, but that does not include an active agent, in a solid or semi-solid form comprising the following steps in any suitable order:

(a) heating one or a plurality of plant oils in a combined amount that is sufficient, in combination with one or more other ingredients, for producing a composition in a solid or semi-solid form to a temperature, and for a period of time, that are effective for evenly heating the plant oil(s), with an amount of mixing as is required, for example, from about 75° C. to about 85° C.;

(b) adding an amount of FANCOL VB that is sufficient, in a combination with one or more other method ingredients, for producing a composition in a solid or semi-solid form to any plant oils heated in step (a), and heating the FANCOL VB at a temperature, and for a period of time, that are effective for evenly heating the FANCOL VB, and for dissolving the FANCOL VB in any such plant oils, with an amount of mixing as is required, for example, from about 75° C. to about 85° C.;

(c) adding an amount of bees wax that is sufficient, in a combination with one or more other method ingredients, for producing a composition in a solid or semi-solid form to the product of step (b), and heating the bees wax at a temperature, and for a period of time, that are effective for dissolving the bees wax in such product, with an amount of mixing as is required, for example, from about 75° C. to about 85° C.;

(d) adding one or a plurality of fatty alcohols in a combined amount that is sufficient, in a combination with one or more other method ingredients, for producing a composition in a solid or semi-solid form to the product of step (c), and heating the fatty alcohols at a temperature, and for a period of time, that are effective for dissolving the fatty alcohols in such product, with an amount of mixing as is required, for example, from about 75° C. to about 85° C.;

(e) adding one or a plurality of fats in a combined amount that is sufficient for producing, in a combination with one or more other method ingredients, a composition in a solid or semi-solid form to the product of step (d), and heating the fats at a temperature, and for a period of time, that are effective for dissolving the fats in such product, with an amount of mixing as is required, for example, from about 75° C. to about 85° C.;

(f) adding an amount of Finsolv TN that is sufficient, in a combination with one or more other method ingredients, for producing a composition in a solid or semi-solid form to the product of step (e), and heating the Finsolv TN at a temperature, and for a period of time, that are effective for dissolving the Finsolv TN in such product, with an amount of mixing as is required, for example, from about 75° C. to about 85° C.;

(g) adding an amount of Natunola Castor 1023 that is sufficient, in a combination with one or more other method ingredients, for producing a composition in a solid or semi-solid form to the product of step (f), and heating the Natunola Castor 1023 at a temperature, and for a period of time, that are effective for dissolving the Natunola Castor 1023 in such product, with an amount of mixing as is required, for example, from about 75° C. to about 85° C. for a period of time ranging from about 1 hour to about 1.5 hours;

(h) cooling the product of step (g) to a temperature that permits one or a plurality of flavoring ingredients to be mixed therewith out significantly reducing the flavor of the flavoring ingredients, or rending them flavorless, for example, from about 70° C. to about 80° C.;

(i) adding one or a plurality of flavoring ingredients in a combined amount that is sufficient, when present in the composition, for providing the composition with a desirable or distinct flavor, or for partially or fully masking one or more bitter or undesirable flavors present therein, or a combination thereof, with the product of step (h) at a temperature, and for a period of time, that is sufficient for distributing the flavorings throughout such product, for example, from about 70° C. to about 80° C. for a period of time ranging from about 15 to about 20 minutes; and (j) optionally, pouring or transferring the product of step (i) into one or a plurality of molds and allowing the product to partially or fully harden, set or solidify therein;

wherein the composition is in a solid or semi-solid form.

Non-Flavored Compositions Including Active Agent(s) (OTC and No Flavor)

In another aspect, the present invention provides a method for producing a topical active-agent containing composition that does not include a flavoring ingredient in a solid or semi-solid form comprising the following steps in any suitable order:

(a) heating one or a plurality of plant oils in a combined amount that is sufficient, in combination with one or more other ingredients, for producing a composition in a solid or semi-solid form to a temperature, and for a period of time, that are effective for evenly heating the plant oil(s), for example, with an amount of mixing as is required, from about 75° C. to about 85° C.;

(b) adding an amount of FANCOL VB that is sufficient, in a combination with one or more other method ingredients, for producing a composition in a solid or semi-solid form to any plant oils heated in step (a), and heating the FANCOL VB at a temperature, and for a period of time, that are effective for evenly heating the FANCOL VB, and for dissolving the FANCOL VB in any such plant oils, with an amount of mixing as is required, for example, from about 75° C. to about 85° C.;

(c) adding an amount of bees wax that is sufficient, in a combination with one or more other method ingredients, for producing a composition in a solid or semi-solid form to the product of step (b), and heating the bees wax at a temperature, and for a period of time, that are effective for dissolving the bees wax in such product, with an amount of mixing as is required, for example, from about 75° C. to about 85° C.;

(d) adding one or a plurality of fatty alcohols in a combined amount that is sufficient, in a combination with one or more other method ingredients, for producing a composition in a solid or semi-solid form to the product of step (c), and heating the fatty alcohols at a temperature, and for a period of time, that are effective for dissolving the fatty alcohols in such product, with an amount of mixing as is required, for example, from about 75° C. to about 85° C.;

(e) adding one or a plurality of fats in a combined amount that is sufficient for producing, in a combination with one or more other method ingredients, a composition in a solid or semi-solid form to the product of step (d), and heating the fats at a temperature, and for a period of time, that are effective for dissolving the fats in such product, with an amount of mixing as is required, for example, from about 75° C. to about 85° C.;

(f) adding an amount of Finsolv TN that is sufficient, in a combination with one or more other method ingredients, for producing a composition in a solid or semi-solid form to the product of step (e), and heating the Finsolv TN at a temperature, and for a period of time, that are effective for dissolving the Finsolv TN in such product, with an amount of mixing as is required, for example, from about 75° C. to about 85° C.;

(g) adding an amount of Natunola Castor 1023 that is sufficient, in a combination with one or more other method ingredients, for producing a composition in a solid or semi-solid form to the product of step (f), and heating the Natunola Castor 1023 at a temperature, and for a period of time, that are effective for dissolving the Natunola Castor 1023 in such product, with an amount of mixing as is required, for example, from about 75° C. to about 85° C. for a period of time ranging from about 1 hour to about 1.5 hours;

(h) adding one or a plurality of active ingredients in a combined amount that is sufficient, when present in a product of step (g) in a solid or semi-solid form, for repairing, improving or fully healing a skin disorder, disease, adverse condition or other malady of a mammal, or for causing the mammal's skin to experience a reduction in pain, soreness or itchiness, or an increase in soothing, softening or conditioning, or a combination thereof, with the product of step (g) at a temperature, and for a period of time, that is sufficient for dissolving the active ingredients in such product, for example, from about 75° C. to about 85° C.; and (i) optionally, pouring or transferring the product of step (h) into one or a plurality of molds and allowing the product to partially or fully harden, set or solidify therein;

wherein the composition is in a solid or semi-solid form.

Flavored Compositions Including Active Agent(s) (OTC and Including Flavoring)

In another aspect, the present invention provides a method for producing a topical active-agent containing composition that includes at least one flavoring ingredient in a solid or semi-solid form comprising the following steps in any suitable order:

(a) heating one or a plurality of plant oils in a combined amount that is sufficient, in combination with one or more other ingredients, for producing a composition in a solid or semi-solid form to a temperature, and for a period of time, that are effective for evenly heating the plant oil(s), with an amount of mixing as is required, for example, from about 75° C. to about 85° C.;

(b) adding an amount of FANCOL VB that is sufficient, in a combination with one or more other method ingredients, for producing a composition in a solid or semi-solid form to any plant oils heated in step (a), and heating the FANCOL VB at a temperature, and for a period of time, that are effective for evenly heating the FANCOL VB, and for dissolving the FANCOL VB in any such plant oils, with an amount of mixing as is required, for example, from about 75° C. to about 85° C.;

(c) adding an amount of bees wax that is sufficient, in a combination with one or more other method ingredients, for producing a composition in a solid or semi-solid form to the product of step (b), and heating the bees wax at a temperature, and for a period of time, that are effective for dissolving the bees wax in such product, with an amount of mixing as is required, for example, from about 75° C. to about 85° C.;

(d) adding one or a plurality of fatty alcohols in a combined amount that is sufficient, in a combination with one or more other method ingredients, for producing a composition in a solid or semi-solid form to the product of step (c), and heating the fatty alcohols at a temperature, and for a period of time, that are effective for dissolving the fatty alcohols in such product, with an amount of mixing as is required, for example, from about 75° C. to about 85° C.;

(e) adding one or a plurality of fats in a combined amount that is sufficient for producing, in a combination with one or more other method ingredients, a composition in a solid or semi-solid form to the product of step (d), and heating the fats at a temperature, and for a period of time, that are effective for dissolving the fats in such product, with an amount of mixing as is required, for example, from about 75° C. to about 85° C.;

(f) adding an amount of Finsolv TN that is sufficient, in a combination with one or more other method ingredients, for producing a composition in a solid or semi-solid form to the product of step (e), and heating the Finsolv TN at a temperature, and for a period of time, that are effective for dissolving the Finsolv TN in such product, with an amount of mixing as is required, for example, from about 75° C. to about 85° C.;

(g) adding an amount of Natunola Castor 1023 that is sufficient, in a combination with one or more other method ingredients, for producing a composition in a solid or semi-solid form to the product of step (f), and heating the Natunola Castor 1023 at a temperature, and for a period of time, that are effective for dissolving the Natunola Castor 1023 in such product, with an amount of mixing as is required, for example, from about 75° C. to about 85° C. for a period of time ranging from about 1 hour to about 1.5 hours;

(h) adding one or a plurality of active ingredients in a combined amount that is sufficient, when present in a product of step (g) in a solid or semi-solid form, for repairing, improving or fully healing a skin disorder, disease, adverse condition or other malady of a mammal, or for causing the mammal's skin to experience a reduction in pain, soreness or itchiness, or an increase in soothing, softening or conditioning, or a combination thereof, with the product of step (g) at a temperature, and for a period of time, that is sufficient for dissolving the active ingredients in such product, for example, from about 75° C. to about 85° C.;

(i) cooling the product of step (h) to a temperature that permits one or a plurality of flavoring ingredients to be mixed therewith out significantly reducing the flavor of the flavoring ingredients, or rending them flavorless, for example, from about 70° C. to about 80° C.;

(j) adding one or a plurality of flavoring ingredients in a combined amount that is sufficient, when present in the composition, for providing the composition with a desirable or distinct flavor, or for partially or fully masking one or more bitter or undesirable flavors present therein, or a combination thereof, with the product of step (i) at a temperature, and for a period of time, that is sufficient for distributing the flavorings throughout such product, for example, from about 70° C. to about 80° C. for a period of time ranging from about 15 to about 20 minutes; and (k) optionally, pouring or transferring the product of step (j) into one or a plurality of molds and allowing the product to partially or fully harden, set or solidify therein;

wherein the composition is in a solid or semi-solid form.

In yet other aspects, the present invention provides compositions that are produced by the above methods.

BRIEF DESCRIPTION OF THE DRAWINGS

The patent or application file contains at least one drawing and/or photograph executed in color. Copies of this patent or patent application publication with color drawing(s) and/or photograph(s) will be provided by the Office upon request and payment of the necessary fee.

FIG. 5 shows that the two plaques that are present on the forearm shown in FIG. 2 completely disappeared (i.e., had a 100% improvement). FIG. 5 also shows the same wrist that is shown in FIG. 4, but as the wrist existed after being treated only with a hydrocortisone-containing solid composition of the invention, prepared in the manner described in Example 1, and having the larger size shown in FIG. 1, with thirty applications of the composition being applied to the wrist spaced equally apart over a period of seven days. FIG. 5 shows that the eczema that is present on the wrist in FIG. 4 completely disappeared (i.e., had a 100% improvement).

FIG. 8 shows that the dry skin (on the lips) that is present on the face and the eczema that is present on the chin in FIGS. 6 and 7, respectively, completely disappeared (i.e., had a 100% improvement).

FIG. 9 is a set of two photographs showing the dorsal aspect of the left hand of a fifty-year-old female patient having psoriasis, whose initials are PT.

FIG. 10 is a set of two photographs showing the palmar aspect of the same left hand of the same female patient that is pictured in FIG. 9.

FIG. 11 is a set of two photographs showing the dorsal aspect of the right hand of the same female patient whose left hand is pictured in FIG. 9 and FIG. 10.

FIG. 12 is a set of two photographs showing the palmar aspect of the right hand of the same female patient whose left hand is pictured in FIG. 9-11.

FIG. 13 is a set of two photographs showing the dorsal aspects of the left and right hands of the same female patient whose hands are pictured in FIGS. 9-12. FIG. 13A shows the left and right hands as they were present prior to receiving any type of treatment with any compositions of the invention for the dryness, cracks, and cuts appearing thereon, with an emphasis on the thumbs, index fingers, and knuckles of both hands. FIG. 13B shows the same left and right hands that are shown in FIG. 13A, but as the left and right hands existed after being treated only with a hydrocortisone-containing solid composition of the invention in a form of a large solid stick, prepared in the manner described in Example 6, and having the larger size shown in FIG. 1, with about 100 applications of about 0.5 ml/application of the composition being applied to the palm spaced equally apart over a period of thirty days (i.e., about 3-4 applications per day). A comparison of the left and right hands that are shown in FIG. 13A with the left and right hands that are shown in FIG. 13B show that the dryness and cracks that are shown in FIG. 13A are significantly moisturized and reduced, and that the cuts that are shown in FIG. 13A have completely disappeared (i.e., have a 100% improvement).

FIG. 14 is a set of two photographs showing the palmar aspects of the left and right hands of the same female patient whose hands are pictured in FIGS. 9-13.

FIG. 15 is a set of two photographs showing the face of a thirty-five-year-old female patient having seborrheic dermatitis, whose initials are SN.

FIG. 16 is a set of two photographs showing the face of a forty-one-year-old male patient having seborrheic dermatitis, whose initials are JT.

FIG. 17 is a set of two photographs showing the face of a seventeen-year-old female patient having eczema, whose initials are SR.

FIG. 18 is a set of two photographs showing the left hand of a fifty-three-year-old female patient having eczema, whose initials are PR.

FIG. 19 is a set of two photographs showing the right hand of the same fifty-three-year-old female patient having eczema, whose initials are PR.

DETAILED DESCRIPTION OF THE PREFERRED EMBODIMENTS

Figure 1:
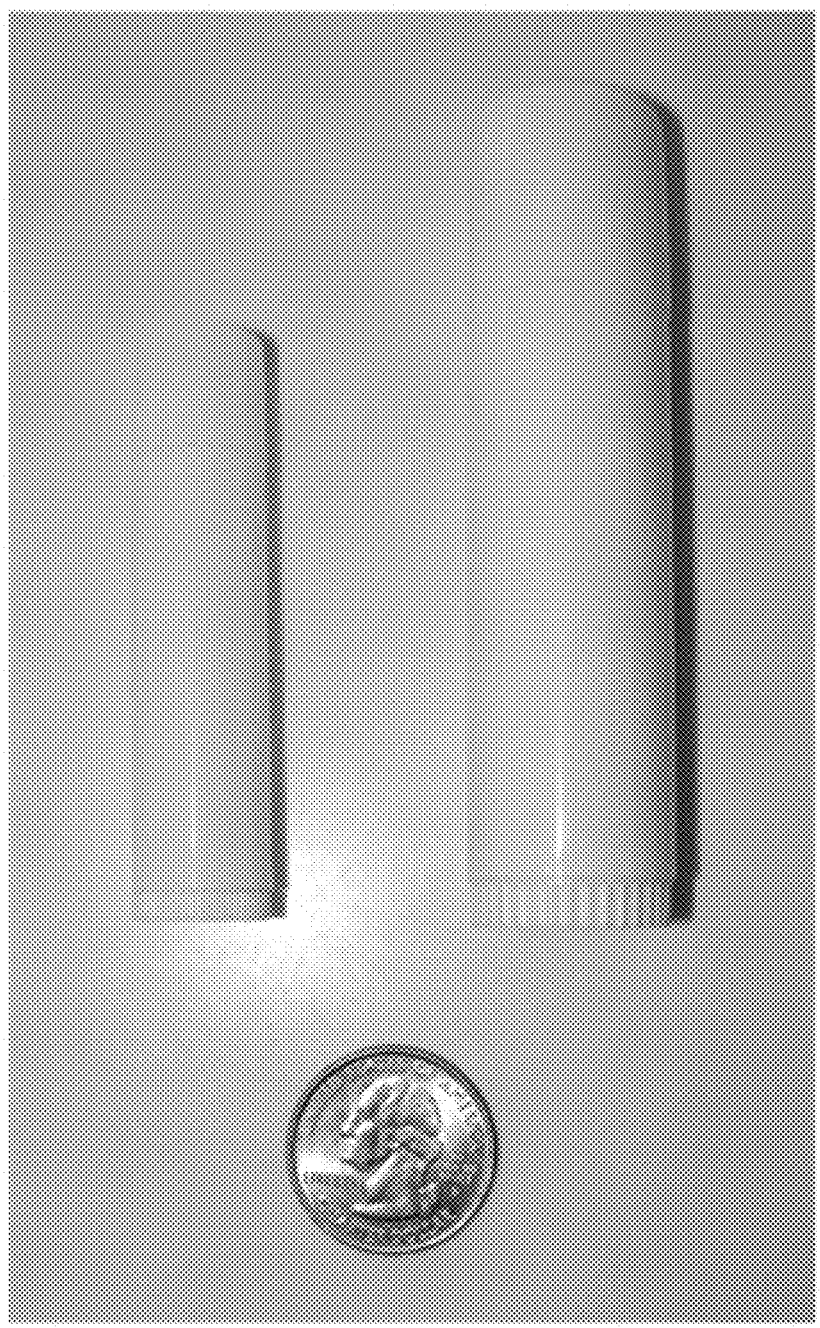
FIG. 1 is a photograph showing two roll-up, stick-shaped, hydrocortisone-containing compositions of the invention, prepared in a solid form in a manner described in Example 1, and packaged into two very different sized plastic containers (having corresponding plastic lids). The smaller sized container includes about 0.15 ounce of the composition, and measures about
6.0 cm in length and about 1.5 cm in diameter, and would likely be used with lips, and the larger sized container includes about 0.50 ounce of the composition, and measures about 7.6 cm in length and about 2.0 cm in diameter, and would likely be used with larger areas of the skin or body. As is shown in FIG. 1, the lower portion of each of the containers (farthest away from the lids) may be rotated or twisted in a counter clockwise (or clockwise or other) manner to forcibly cause the solid compositions to protrude outwards from the containers, thereby permitting a user to topically apply the protruding solid compositions to one or more areas of the user's skin. The quarter shown in FIG. 1 is illustrated for the purposes of having a size comparison of the two different sized containers shown in FIG. 1.

The present invention may be understood more readily by reference to the following detailed description of the preferred embodiments of the invention, and to the examples included therein.

Definitions

For purposes of clarity, various terms and phrases used throughout this specification and the appended claims are defined in the manner set forth below. If a term or phrase used in this specification, or in the appended claims, is not defined below, or otherwise in this specification, the term or phrase should be given its ordinary meaning.

The terms "about" and "approximate" as are used herein mean approximately, as is known, and may be determined, by those having ordinary skill in the art, and typically includes a variation of a numeric value described herein by ±0.2.

The phrase "ambient temperature" as is used herein means the temperature of the surroundings, such as the temperature of a particular room.

The phrase "antioxidant agent" as is used herein means an agent that has an ability to prevent, reduce or aid in the prevention or reduction of, an oxidation, degradation and/or other decomposition of one or more ingredients or components, such as a fat or an oil, and/or to prevent, or aid in the prevention of, oxygen-based damage to hair, skin or other cells. Antioxidant agents include, for example, various tocopherol mixtures, edible acids (citric acid, ascorbic acid and the like), vitamin A, vitamin C, vitamin E, beta-carotene, selenium, magnesium, herbal extracts, such as a Rosemary, Sage, Oregano, Ginger, Marjoram or Rosemary Oleoresins extract, plant phenols, such as Vanillin, ellagic acid and Resveratrol, and synthetic antioxidants, such as tertiary butylhydroquinone (TBHQ), butylated hydroxyamisole (BHA) or butylated hydroxytoluene (BHT), or mixtures thereof.

The term "balm" as is used herein means a substance that typically is oily in nature, a solid or semi-solid, and soothing to the skin of a human being and/or animal when topically applied thereto (either immediately or at a subsequent time after one or a series of multiple applications), particularly when it includes one or more active agents, such as hydrocortisone, and which may or may not have a pleasant (or other smell). Examples of balms include aloe, ChapStick® and compositions within the present invention.

The phrase "carrier vehicle" as is used herein means a medium for, or capable of, providing a controlled delivery of one or a plurality of active agents to a mammal, or part thereof, such as the skin.

The term "component" as is used herein means a part, portion, element, constituent or ingredient, and is used interchangeably with "ingredient" and "agent." For example, in connection with a composition of the invention, this term may mean an ingredient, or combination of ingredients, used in the composition, or a part, portion, element or constituent thereof, depending upon the context in which this term is used, which may readily be determined by those having ordinary skill in the art.

The phrase "base" as is used herein refers to a carrier vehicle for one or a plurality of active agents, such as hydrocortisone, that may be applied to the skin of a normal and healthy mammal (other than possibly having one more adverse skin conditions, disorders or diseases, as are discussed herein) in a reasonable quantity over a reasonable period of time, preferably without an unreasonable risk of harm, injury, inflammation, irritation or allergic response to, or by, the skin, or illness or harm to the mammal. Persons of ordinary skill in the art may readily determine whether or not a particular base includes these characteristics.

The phrase "diluent" as is used herein means a substance or agent that dilutes, facilitates a physical separation of one or more ingredients and/or makes thinner or weaker. Diluent materials that are suitable for use with mammals could generally include complex polysaccharides, carbohydrates, smaller sugars (dextrose, sucrose and the like), dicalcium phosphate, tricalcium phosphate, maltodextrin and water.

The term "distinctive" as is used herein means characteristic of, identifying or serving to distinguish. For example, a distinctive taste may be a bitter taste, a sour taste, a sweet taste, a salty taste, a fruity taste, a vanilla taste and/or the like.

The term "eczema" as is used herein means a particular type of inflammatory reaction of the skin in which there are typically tiny blister-like raised areas (vesicles) in the first stage followed by reddening (erythema), swelling (edema), bumps (papules), and crusting of the skin, and finally thickening and scaling of the skin.

The term "effective" as is used herein in connection with a composition ingredient or composition, in many instances, and depending upon the context, as may be determined by those having ordinary skill in the art, means that the ingredient, alone or in combination with one or more other ingredients, provides a composition with one or more of the qualities, characteristics and/or benefits that are described herein, or that the composition has one or more of such qualities, characteristics and/or benefits, such as an activity resulting from an active ingredient present therein.

The term "emollient" as is used herein means an ingredient, or combination of ingredients, that increases the softness of the skin, restores the skin and/or helps maintain water and/or oils in the skin.

The term "emulsifier" as is used herein means any substance or agent that aids in the formation of an emulsion, such as egg yolk, egg lecithin, soy lecithin and mono- and diglycerides.

The term "emulsion" as is used herein means a generally stable and homogeneous mixture of two liquids that do not normally mix (i.e., they are immiscible between themselves), such as vegetable oil and water, for example, milk and mayonnaise. Emulsions can be true colloids or less stable mixtures, which tend to separate in a short time. An emulsion can often be broken down (i.e. the liquids separated) by factors such as mechanical manipulation, chemical effects and/or time.

The term "FANCOL VB" as is used herein means *Butyrospermum Parkii* Butter *Limnanthes Alba* Seed Oil, which contains, or consists of, vegetable derived lipids and sterol-enriched shea butter extract. Its INCI name is *Limnanthes Alba* (Meadowfoam) Seed Oil, *Butyrospermum Parkii* (Shea Butter) Extract. It is commercially available from sources that are known by those having ordinary skill in the art, for example, from The Fanning Corporation (Chicago, Ill.) and Elementis Specialties, Inc. (Hightstown, N.J.).

The term "fat" as is used herein means any of the various saturated and/or unsaturated (including monounsaturated and polyunsaturated), hydrogenated or unhydrogenated soft solid, semisolid and/or solid organic compounds that generally comprise the glyceride esters of fatty acids and associated phosphatides, sterols, alcohols, hydrocarbons, ketones and/or related compounds, components thereof and/or mixtures or other combinations thereof. Such components include, but are not limited to, fatty acids, glycerides (mono-, di- and tri-), ethyl and other esters of fatty acids, as well as components thereof, and combinations thereof. Fats occur widely in organic tissue, particularly in the subcutaneous connective tissue of animals (beef, poultry, pork, lamb, liver and the like), and in the seeds, nuts and fruits of plants. There is generally no chemical difference between fats and oils, with the only distinction being that fats are generally solid at room temperature and oils are generally liquid at room temperature.

The phrase "fatty acids" as is used herein means carboxylic acids that generally are derived from, or contained in, an animal, vegetable or other fat or oil, whether saturated, unsaturated, monounsaturated, polyunsaturated, aromatic, essential, nonessential, in a cis- or trans-form, in the ethyl esters, mono-, di- or tri-glycerides, free fatty acids or other forms, and components and combinations of the foregoing. Fatty acids include, but are not limited to, the specific fatty acids identified below:

| Common Name | Number of Carbon Atoms | Number of Double Bonds |
|---|---|---|
| Butyric Acid | 4 | 0 |
| Caproic Acid | 6 | 0 |
| Caprylic Acid | 8 | 0 |
| Capric Acid | 10 | 0 |
| Lauric Acid | 12 | 0 |
| Myristic Acid | 14 | 0 |
| Palmitic Acid | 16 | 0 |
| Palmitoleic Acid | 16 | 1 |
| Stearic Acid | 18 | 0 |
| Oleic Acid | 18 | 1 |
| Linoleic Acid | 18 | 2 |
| Alpha-Linolenic Acid (ALA) | 18 | 3 |
| Gamma-Linolenic Acid (GLA) | 18 | 3 |
| Arachidic Acid | 20 | 0 |
| Gadoleic Acid | 20 | 1 |
| Arachidonic Acid (AA) | 20 | 4 |
| Eicosapentaenoic Acid (EPA) | 20 | 5 |
| Behenic Acid | 22 | 0 |
| Erucic Acid | 22 | 1 |
| Docosahexaenoic Acid | 22 | 6 |
| Lignoceric Acid | 24 | 0 |

Other fatty acids are known by those of skill in the art. A wide variety of fatty acids are commercially available from sources known by those of skill in the art. Also, oils can be separated into their component fatty acids on a capillary column in a gas chromatograph, and the relative fatty acid contents measured. Additional information concerning fatty acids is readily available from the Fatty Acid Producer's Council (New York, N.Y.).

The phrase "fatty alcohol" as is used herein means an alcohol that is derived from a fat or oil, which may originate in a plant or plant part, but may also be synthesized in an animal or in algae or the like. Fatty alcohols are often closely related to fatty acids, including omega-3 fatty acids. They often have an even number of carbon atoms, and production from fatty acids generally yields normal-chain alcohols, in which the alcohol group (—OH) attaches to the terminal carbon atom. Other processing can yield iso-alcohols, in which the alcohol attaches to a carbon atom located in the interior of the carbon chain. Fatty alcohols include normal chain alcohols, saturated alcohols, unsaturated alcohols, acetylenic alcohols, sulfated alcohols, branched chain alcohols and/or the like. Examples of some specific fatty alcohols include, but are not limited to, stearyl alcohol (1-octadecanol), isostearyl alcohol (16-methylheptadecan-1-ol), oleyl alcohol, linoleyl alcohol, behenyl alcohol, lignoceryl alcohol, ceryl alcohol, capryl alcohol (1-octanol), capric alcohol (1-decanol, decyl alcohol), lauryl alcohol (dodecanol, 1-dodecanol), myristyl alcohol (1-tetradecanol), cetyl alcohol (1-hexadecanol), palmitoleyl alcohol (cis-9-hexadecen-1-ol) and heptadecyl alcohol. Other fatty alcohols are known by those having ordinary skill in the art.

The term "firm" as is used herein means having a solid and/or compact structure that is partially or fully resistant to stress or externally applied pressure.

The phrase "function effectively" as is used herein means that a base composition or active agent-containing composition of the invention has an ability to provide, produce or have one or more of the benefits and advantages that are described herein for such compositions, such as having an activity provided by an active ingredient present therein.

The term "humans" as is used herein, unless otherwise stated, includes human beings that are babies, infants, children or adults.

The term "ingredient" as is used herein interchangeably with "component" and "agent" in connection with compositions described herein.

The abbreviation "INCI" as is used herein means International Nomenclature Cosmetic Ingredient.

The term "lipid" as is used herein means any of a group of organic compounds, including fats, oils, waxes, sterols, and triglycerides, that generally are insoluble in water but soluble in nonpolar organic solvents, are oily to the touch, and together with carbohydrates and proteins constitute the principal structural material of living cells.

The phrase "liquid" as is used herein means a state of matter, neither solid nor gas, in which a substance exhibits a characteristic readiness to flow, and the shape of which is generally determined by the container that it fills.

The term "mammals" as is used herein includes humans and non-human mammals, such as animals (dogs, cats, horses, cows, bulls, pigs, goats, sheep, birds, fowl, or the like)).

The phrase "marine oil" as is used herein includes, but is not limited to, "fish oil" and one or more individual components of marine oil, such as an omega-3 fatty acid, or a combination thereof. Marine oils include, for example, herring oil, cod oil, anchovy oil, tuna oil, sardine oil, menhaden oil and algae oil.

The phrase "mucosal membrane" as is used herein means a membrane that lines a body passage that communicate with the air, such as the respiratory and alimentary tracts, and which may have cells and/or associated glands that secrete mucus.

The phrase "Natunola Castor 1023" as is used herein means a substance that consists of, or contains, castor oil, glycerine soybean germ extract, corn starch and silica. Its INCI name is *Ricinus Communis* (Castor) Seed Oil (and) *Glycine Soja* (Soybean) Germ Extract (and) *Zea Mays* (Corn) Starch (and) Silica,). It is commercially available from sources that are known by those having ordinary skill in the art, for example, from Natunola Health Biosciences, Inc. (Winchester, Ontario, Canada) or Natunola Health, Inc. (Winchester, Ontario, Canada).

The term "non-OTC" as is used herein in connection with a topical skin composition means that the composition typically would not be regulated in the U.S. by the U.S. Federal Drug Administration (FDA), or by its statutes, regulations and rules. Compositions of the invention that do not include any active ingredients, such as hydrocortisone, would generally be classified as "non-OTC" compositions.

The term "oil" as is used herein means a fat that generally is viscous, liquid or liquefiable at room temperature, and includes mixtures and other combinations of one or more oils and/or components of oils, such as fatty acids, glycerides and/or ethyl esters of fatty acids (or components thereof).

The phrase "on a regular basis" as is used herein means that a composition employed in the methods of the invention is applied to the skin of a mammal on a reasonably continuous basis (i.e. without delaying one or more applications for an unreasonably lengthy period of time), for example, a regular application of the composition to the mammal's skin one, two, three, four, five, six, seven, eight, nine, ten and so forth times within a period of one, two, three, four, five, six, seven, eight, nine, ten and so forth days for a duration of one, two, three, four, five, six, seven, eight, nine, ten and so forth days or weeks.

The abbreviation "OTC" as is used herein in connection with a topical skin composition means that the composition typically would be regulated in the U.S. by the U.S. Federal Drug Administration (FDA), and its statutes, regulations and/or rules, such as the Federal Food, Drug and Cosmetics Act, which is hereby incorporated herein in its entirety by reference along with its associated regulations and rules. For example, compositions of the invention that include an active ingredient, such as hydrocortisone, would generally be classified as "OTC" compositions. The phrase "plant seed oil" as is used herein means an oil that is extracted, or otherwise obtained from, either directly or indirectly, a seed of a plant, particularly oily seeds, including one or more individual components thereof and mixtures thereof. Plant seed oils include, but are not limited to, Black Currant seed oil, Borage seed oil, safflower seed oil, sunflower seed oil, sesame seed oil, avocado seed oil, pumpkin seed oil, olive seed oil, coconut seed oil, rapeseed oil, flaxseed (linseed) oil, cottonseed oil, tung oil, meadowfoam seed oil, parsley seed oil, carrot seed oil, fennel fruit oil, parsnip seed oil, coriander seed oil, chervil seed oil, caraway plant oil, celery seed oil and others that are described herein. Other plant seed oils are known by those having ordinary skill in the art.

The phrase "plant oil" as is used herein means an oil that is extracted, or otherwise obtained from, either directly or indirectly, a plant, particularly an oily plant, including one or more individual components thereof, and mixtures thereof. Plant oils include, but are not limited to, Evening Primrose oil, Borage oil, safflower oil, sunflower oil, peanut oil, walnut oil, almond oil, avocado oil, olive oil, corn oil, soy oil, soybean oil, coconut oil, palm oil, palm kernel oil, castor oil, mineral oil and others that are described herein. Other plant oils are known by those having ordinary skill in the art.

The term "pliable" as is used herein means supple enough to partially (greater than about 0% but less than about 100%) or fully (about 100%) bend without breaking.

The term "plurality" as is used herein means more than one, such as two, three, four, five, six, seven, eight, nine, ten, eleven, twelve, thirteen, fourteen, fifteen, twenty, twenty-five, thirty, thirty-five and so forth.

The term "prescription" as is used herein means a written, telephonic or other order, typically made by a medical doctor (physician), for a preparation, distribution and/or administration of a medicine or other treatment to a patient, or other individual, for example, by a pharmacist or pharmacy.

The abbreviation "q.s." as is used herein means a sufficient quantity, for example, to cause the weight percent of a composition to be 100%, or to obtain a desired effect or benefit. The plant or plant seed oil ingredient of the base and active-agent compositions of the invention, when present, such as castor oil, may be varied in a manner desired or required to cause the weight percent of the composition to be 100%.

The phrase "room temperature" as is used herein means the temperature in a room, which generally ranges from about 15° C. to about 30° C. (from about 59° F. to about 86° F.), and more usually ranges from about 21° C. to about 23° C. (from about 70° F. to about 74° F.). The "ambient temperature" of a room is "room temperature."

The phrase "safe for use" as is used herein in connection with compositions described herein, and methods of the invention, means that the compositions, and the components contained therein, and the methods, using reasonable quantities of active and other components, and administered for reasonable periods of time (such as those quantities and periods of time described herein, or as otherwise recommended for a particular mammal by a physician, veterinarian or other skilled clinician), which may vary for different types of mammals, do not cause, or present an unreasonable risk of harm, damage, defect, disorder, deformity or injury to, or by, an average mammal, or the skin of an average mammal, whether or not the mammal has one or more skin disorders, diseases, conditions or maladies.

The phrase "semi-solid" as is used herein means a state of matter that is intermediate in properties, especially in rigidity, firmness and compactness, between a solid and a liquid, such as a gel, a cream, an ointment and/or the like. A semi-solid composition is typically not rigid, compact or firm. Unlike a solid composition, a user may insert a finger into a pot containing a semi-solid composition, such as petroleum jelly, and scoop a portion of it out with the finger.

The term "shape" as is used herein in connection with base compositions and active agent-containing compositions includes, but is not limited to, any of a wide variety of known or unknown shapes of any desired or required size, such as circular or oval spheres, square or rectangular cubes or prisms, triangular prisms, square-based pyramids, triangle-based pyramids, cuboid hexagonal prisms, cones, cylinders and/or the like. The shaped of a "stick" as is referred to herein means a cylinder. The sizes of such shapes (length, width, depth and/or the like) may be any size that is desired, convenient for use or required including, but not limited to, from one or a plurality of mm (or smaller) to one or a plurality of inches or feet. Two cylinder-shaped active-agent containing compositions, having two very different sizes, are shown in FIG. 1.

The term "skin" as is used herein in connection with human beings means the outer integument or covering of the body, containing multiple layers, including the epidermis (outer most layer, which typically ranges from about 0.5 to about 1.5 mm in thickness), which itself includes the five layers (from bottom to top) of the stratum basale, stratum spinosum, stratum granulosurn, stratum licidum and stratum corneum, the dermis (or cornium) (mid layer, which typically ranges from about 0.3 to about 3.0 mm in thickness), which includes collagen tissue, elastic tissue and reticular fibers, and an upper papillar layer and a lower reticular layer, and subcutaneous tissue (below the dermis). As it is used herein, skin includes, but is not limited to, the outer covering of the face (including the lips, eye lids and outer portions of the ears), scalp, neck, arms, legs, hands, feet, fingers, toes, chest, breasts, back, abdomen, genitals and/or the like, and portions or parts thereof, of a human being or non-human mammal, such as an animal. In connection with non-human mammals, the term "skin" includes the outer covering of the body that is not fur, hair, feathers and/or the like. As it is used herein, the term "skin" also includes inner areas or coverings of the body including, but not limited to, the inside of the nostrils of the nose, the inside of the mouth, the inner ears, inside folds and areas of female and male genitals, and all mucosal membranes.

The phrase "solid" as is used herein means a state of matter, neither liquid nor gas, generally having a definite shape and volume, and typically being rigid, firm and/or compact in substance, but possibly having an ability to be pliable, and to be softened into a less firm and/or rigid state, or melt, upon heating it to a temperature that is above the melting point of the solid (or to some other temperature that causes it to soften, which may be determined by those having ordinary skill in the art). A "solid" composition is different from a "semi-solid" composition, such as petroleum jelly, as a result of its rigidness, firmness and/or compactness. For example, a user would typically have an ability to insert a finger into a "semi-solid" composition present in a pot and scoop a portion of the composition out of the pot with the finger. The same user typically would not have an ability to do the same with a "solid" composition present in the same pot as a result of the rigidity, firmness and/or compactness of the "solid" composition. However, a "solid" composition, as is described herein, may be transformed into a "semi-solid" or "liquid" state by applying heat to the "solid," causing the "solid" to partially or fully melt, as is discussed herein (i.e., after the "solid" product has been produced).

The phrases "surfactant" and "wetting agents" as are used herein mean substances or agents that lower the surface tension (tendency of a liquid to reduce its exposed surface to the smallest possible area) of a liquid, generally allowing easier spreading, and/or the interfacial tension between two liquids. Surfactants are usually organic compounds that are amphipathic in that they contain both hydrophobic groups (their "tails") and hydrophilic groups (their "heads"). Therefore, they are typically sparingly soluble in both organic solvents and water. Surfactants generally reduce the surface tension of water by adsorbing at the air-water interface, and reduce the interfacial tension between oil and water by adsorbing at the liquid-liquid interface. Many surfactants can also assemble in the bulk solution into aggregates that are known as micelles.

The phrases "topical administration," "topically administering" and "topically applying" as are used herein mean an application onto the skin (generally onto one or more exposed or outer surfaces thereof, such as the outermost layer of the epidermis, which is exposed and visually observable), for example, using hands, fingers or a wide variety of applicators (roll-up, roll-on or other stick container, tube container, cotton ball, powder puff, Q-tip, pump, brush, mat, cloth and/or the like). The application may be made, for example, by laying, placing, rubbing, sweeping, pouring, spreading and/or massaging into, or onto, the skin, or by any other convenient or suitable method. Compositions that may be applied by topical administration include, but are not limited to, sticks, lipsticks, waxes, creams, lotions, ointments, balms, gels, glosses, sunscreen preparations, cosmetics, masks, leave-on washes or cleansers, depilatory preparations and/or the like.

The term "viscosity" as is used herein means resistance to flow (of a fluid or semi-fluid). Viscosity can be measured using, for example, a commercially available viscometer.

The term "wax" as is used herein means a fatty substance that is often solid at room temperature and softens and melts when warmed. Generally, waxes are similar in composition to fats and oils, with the exception that they do not contain glycerides. Some waxes are hydrocarbons, and others are esters of fatty acids and alcohols. Examples of waxes include, but are not limited to, bees wax, lanolin, carnauba, candelilla, ozokerite, bayberry, sugar cane, paraffin, microcrystalline and sorbitol.

The phrase "weight percent" as is used herein refers to the percent weight, for example, of an ingredient that forms a part of a mixture, base composition, active-agent containing composition, other composition or the like, with the total weight of the mixture, base composition, active-agent containing composition or other composition or the like being 100 weight percent, and is a measure of the relative proportions of two or more quantities in a mixture Thus, weight percent may include any whole, partial, decimal or fractional number above 0, such as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100 (or any amount in between the foregoing, such as 1.1, 1.2, 1.3, 1.4, 1.5, 1.6, 1.7, 1.8, 1.9 and so forth).

The phrase "without significantly reducing the activities of the active ingredients" as is used herein means that the active agent(s) do not have a reduction in activity that is greater than about 50 percent, and preferably that is not greater than about 40%, and more preferably that is not greater than about 30%, and still more preferably that is not greater than about 20%, and even more preferably that is not greater than about 10%, and still more preferably that is not greater than about 5% (out of 100%). Thus, they have an activity ranging from about 50% to about 100%, which is preferably about 60% or higher, more preferably about 70% or higher, still more preferably about 80% or higher, even more preferably about 90% or higher, and still more preferably about 95% or higher, and most preferably 100%.

The phrase "without significantly reducing the flavor of the flavorings" as is used herein means that the flavorings do not have a reduction in flavor that is greater than about 50 percent, and preferably that is not greater than about 40%, and more preferably that is not greater than about 30%, and still more preferably that is not greater than about 20%, and even more preferably that is not greater than about 10%, and still more preferably that is not greater than about 5% (out of 100%). Thus, they have a flavor capacity ranging from about 50% to about 100%, which is preferably about 60% or higher, more preferably about 70% or higher, still more preferably about 80% or higher, even more preferably about 90% or higher, and still more preferably about 95% or higher, and most preferably 100%.

General Description and Advantages

The present invention provides novel base compositions and related topical active agent-containing compositions including hydrocortisone and/or one or a plurality of other active agents, which may be employed, for example, in an over-the-counter, prescription or other pharmaceutical product for human beings or animals having one or a plurality of skin disorders, diseases or adverse conditions, or otherwise, and related methods of production and use. These compositions may be present in any suitable, convenient and/or desired form, including liquids, semi-solids and solids in, for example, a cream, an ointment, a balm, a paste, a gel, a soft or hard solid stick (roll-on, roll-up or otherwise), a form that sprays out of a can, and/or the like, but are preferably present in, and administered using, a roll-up, solid, cylindrical-shaped stick, such as the two such sticks that are illustrated in FIG. 1, or a pot.

The base and active agent-containing compositions of the invention have specific formulations including a unique combination of ingredients, and weight percents thereof which have surprisingly and unexpectedly been determined via a significant amount of experimentation and testing on human beings over a lengthy period of time to function extremely well together, providing topical active agent-containing skin compositions that are extremely efficacious for: (i) repairing, improving, partially (less than 100%) or fully (100%) healing, or otherwise treating a wide variety of different skin disorders, diseases, conditions, maladies, severe (or other) dryness and/or the like, of the skin of mammals, when employed in the manner, and under the conditions, that are described herein, including, but not limited to, inflammation, redness, itching, bumps, blisters, cuts, punctures, other wounds, cracking, severe dryness, allergic reactions, insect bites, microbes (various types of bacteria, viruses and/or the like), trauma, irritant dermatitis, contact dermatitis, seborrheic dermatitis, stasis dermatitis, perleche, psoriasis, eczema, eczema craquele, acne excoriee (a form or irritated and/or picked acne), cheilitis, a variety of different skin complications resulting from acne, xerosis, disease related skin conditions and dryness from a variety of different medications, including, but not limited to, isotretinoin, acitretin, lipid-lowering agents and/or the like; and/or (ii) causing the skin to feel less painful, less irritated, less sore, less itchy, more soothed, more softened and/or more conditioned (in comparison with how the skin felt prior to a use of the composition(s)).

The base and active agent-containing compositions of the invention have numerous very important benefits and advantages in the topical skin treatment field in comparison with other topical compositions for application to the skin, which often do not have such benefits and advantages, including hydrocortisone-containing topical compositions. Extremely advantageously, compositions within the invention typically:

(i) penetrate one or a plurality of layers of a mammal's skin including, for example, the epidermis and dermis, and the tissues present therein, thereby exhibiting efficacious repair, improvement, healing, treatment and/or other beneficial actions in connection with a wide variety of different skin disorders, diseases, adverse conditions and/or the like deep within the layers and/or tissues of the skin, rather than only resting, laying or sitting on top of the outside of the outermost layer of the mammal's skin, as many other topical skin compositions do;

(ii) provide a barrier on the surface of the skin that functions to seal the surface of the skin off from the outside environment, and reduce or prevent transepidermal water loss (TEWL) from the skin, thereby allowing the skin to retain moisture, and protecting the skin, which may already be damaged, injured or diseased, from one or a plurality of adverse environmental and/or other conditions (sun, wind, very high or very low temperatures, precipitation, dirt, debris, and/or the like), thereby permitting the skin to be repaired, improve or fully heal while, at the same time, also preventing further or additional damage or injury (or other adverse effects) to the skin;

(iii) do not have an undesirable feel to the touch or skin of a mammal, such as a very thick, very thin, tacky, sticky, greasy or gritty feel, but rather have a relatively smooth, non-tacky, non-sticky, non-greasy, non-gritty and desirable feel to the touch or skin of a mammal;

(iv) have no significant taste or odor, or have a pleasant or desirable taste, with minimal (typically about 20% or less, and preferably about 10% or less, and more preferably about 5% or less) or none (0%) of the bitterness, bitter taste or other unpleasant or undesirable taste that is typically caused by hydrocortisone and/or other composition ingredients (particularly active agent(s)), and odor to a user when applied to mucosal areas of the user's lips and/or elsewhere (i.e., it typically does not taste or smell bitter or otherwise unpleasant, and often tastes and smells good as a result of the base formulation and/or flavorings masking, hiding, reducing or eliminating the otherwise bitterness, bitter taste and/or smell and/or other unpleasant taste and/or smell of the hydrocortisone (and/or other unpleasant tasting and/or smelling active or inactive ingredient(s)), which is very unusual for hydrocortisone-containing, and many other active ingredient-containing, topical skin compositions and products);

(v) may be formed into a wide variety of different sizes and/or shapes, or in multiple sizes and/or shapes (see, for example, FIG. 1), thereby permitting it to be topically applied to extremely small and extremely large areas of the skin;

(vi) may be applied over various different body surface areas of widely varying sizes and/or types, for example, in a lip-based product for application to the lips, and also in a separate product that is suitable for topical application to larger body surfaces, and, thus, permit a patient to treat very small and/or very large areas of the skin, with no limit in size of skin area to be treated (such as an area that is a size of a pinpoint or smaller and/or an area spanning one or a plurality of square inches or larger);

(vii) are very convenient and easy to administer and deliver by users;

(viii) are safe for use by human beings, animals and other mammals;

(ix) are reliable for patients and other users with respect to their healing effects (i.e., patients can expect to observe or detect an improvement of, or repair in, their skin or a complete healing thereof, as is discussed herein);

(x) preferably, have a relatively solid consistency, being firm, rigid and/or compact, but preferably pliable, thereby allowing them to have longevity on the lips and other areas of the body to which they are topically applied (i.e., they remain on those portions of the body for relatively long periods of time, and typically longer periods of time in comparison with other such products) and a good spreadability (i.e., they easily and readily spread or slide on, over or across the skin);

(xi) do not easily or readily become removed from the skin of a user (by wiping, patting, rubbing, washing and/or the like) after being applied topically thereto, rendering them more likely than products that easily or readily become removed from the skin to repair, improve or heal the skin for a relatively long period of time, and to protect the skin from adverse environmental and/or other conditions, as is discussed above;

(xii) maintain their consistency, form and/or shape (and typically all three) over relatively long periods of time, such as one or a plurality of months or years, and under relatively extreme environmental conditions, such as extremely hot and extremely cold temperatures (i.e., they typically do not melt at very high temperatures and do not crack at very low temperatures), thereby rendering them to be extremely versatile and capable of use at virtually all temperatures, and in virtually all environmental conditions, in which a user may be present or encounter;

(xiii) remain physically and chemically stable over long periods of time, such as a plurality of months or years, and, thus, typically do not deteriorate, disintegrate or otherwise break down, or the like, over time and produce a "gritty" consistency (i.e., including a plurality of rough granules) or other undesirable consistency, as do many other topical skin compositions and products;

(xiv) are cosmetically elegant and physically appealing and desirable in appearance to consumers;

(xv) promote, encourage or otherwise enhance patient compliance (as a result of the benefits described herein); and/or (xvi) are relatively inexpensive.

Most base and active agent-containing compositions of the invention possess each of the above benefits and advantages, rendering them to be significantly more beneficial and advantageous, and great improvements, in comparison with other known (or other) topical skin compositions and products, which typically do not have some or all of such benefits and advantages, including those that contain hydrocortisone. The base and active agent-containing compositions of the invention, and related methods, have been determined via a significant amount of experimentation and testing on human beings, as is discussed herein, and as is illustrated in FIGS. 2-17, to typically be superior (and often far superior) in one or more of the above characteristics (and often in all of these characteristics) in comparison with similar and/or other known base and other compositions, including those that contain hydrocortisone, in: (i) repairing, improving, healing or otherwise treating a wide variety of skin disorders, diseases, conditions, maladies, dryness and/or the like; and/or (ii) causing the skin of a user to experience a reduction in pain, soreness, itching or other discomfort or undesirable effect(s) and/or an increase in soothing, softness, conditioning and/or the like. Extremely advantageously, more desirable, more pronounced and/or more rapid positive results are typically achieved with the inventive compositions in comparison with other topical skin compositions and products.

Also extremely advantageously, the base and active agent-containing compositions of the invention generally have an ability to maintaining their final form, shape and/or consistency (typically all three of them), such as a relatively rigid, firm and compact, but preferably pliable, solid form, preferably in a cylinder (stick) shape under: (i) very high temperatures (i.e., temperatures up to about 50° C. (about 122° F.) and, in some cases, even up to about 60° C. (about 140° F.), for example, in the glove box of a 100° F. vehicle during the summer months in a southern U.S. state; and (ii) very low temperatures, such as on a ski slope in a northern U.S. state during the coldest months of a very cold winter, for example, at temperatures below about 32° F. (0° C.), and even below about 0° F. (−17.7° C.). Thus, in contrast with many other topical skin compositions, which often melt, decompose, disintegrate, deteriorate, or otherwise break down or fall apart, or have some other adverse consistency, form and/or shape change, often causing them to be or become very messy, sloppy, sticky, greasy, tacky, gritty and/or the like, particularly at relatively high temperatures, the base and active agent-containing compositions of the invention, when present in a solid form, such as a stick, generally will not melt, decompose, disintegrate, deteriorate, or otherwise break down or fall apart, or become messy, sloppy, sticky, greasy, tacky or gritty at these relatively high temperatures. This renders such base and active agent-containing compositions of the invention extremely versatile, dependable and reliable. They typically have a melting point ranging from about 50° C. to about 60° C. (from about 122° F. to about 140° F.), a congealing point ranging from about 25° C. to about 30° C. (from about 77° F. to about 86° F.), and no freezing point and, thus, very advantageously, typically have an ability to maintain their form, shape and consistency under very extreme heat and very extreme cold conditions, rendering them useful at virtually all temperatures and conditions that can be endured by human beings, animals and other mammals, and in a wide variety of climates, seasons and areas of the world.

Base compositions and active agent-containing compositions within the present invention, as well as their methods for production, have continuously been experimented with, and improved, over a lengthy period of time. To date, numerous different formulations have been produced and experimentally tested. Those formulations that are referred to herein as "original" were some of the initial formulations that were prepared and experimentally tested, and those formulations that are referred to herein as "subsequent" and/or "improved" are later improved formulations that are more preferred than the original formulations. The methods for production of these improved formulations, which are described herein in detail, are also more preferred.

The improved formulations of the invention have been determined, via a tremendous amount of experimentation over a lengthy period of time, to have an improved (enhanced, easier and better) slip (spreadability) on the skin of human beings, in comparison with the original formulations, permitting them to slide and spread on the skin more easily and rapidly, and coat the skin more fully and with more formulation, regardless of their size or containment device (jar, pot, can, squeezable tube, rigid tube, or the like), reducing, and typically completely eliminating, any "skip" areas of the skin (areas of the skin to be treated or coated with the compositions that mistakenly or inappropriately do not become coated with the compositions, or do not have any of the compositions applied thereto), thereby providing a greater quantity of the compositions to be applied to the skin, and a deeper absorption by, and penetration into, the various layers of the skin by the compositions, and improved patient compliance with respect to their use of the compositions. These are all are very beneficial characteristic for topically applied skin compositions, and significant advantages and improvements in comparison with known topical skin compositions (both over-the-counter and prescription).

Additionally, the improved formulations of the invention have an improved (enhanced or better) taste, smell and/or texture (typically all three) in comparison with the original formulations, even when they do not include one or more flavoring ingredients (as well as when they do), and when they include hydrocortisone. All of these compositions typically have a better taste and smell in comparison with known formulations including hydrocortisone, such as CortiBalm lip balm (Milan, Ind.), and other known formulations, which improves, promotes and encourages patient compliance. (Some active (or other) agents employed in topical skin compositions, for example, hydrocortisone, are known to produce or have an unpleasant taste and/or smell, rendering them undesirable for patients or other users to apply to their mouth or face (or to other areas of their bodies).)

Further, when present, or contained, in a pot or jar, users of the original formulations of the invention typically need to use their fingernails to scrape the formulations out of the pot or jar. Users do not need to do this with the improved formulations of the invention, which is a benefit of these improved formulations in comparison with the original formations.

Moreover, the improved formulations of the invention may be used, and applied, more easily in "cold temperature" situations and environments in comparison with the original formulations.

All base compositions and active agent-containing compositions of the invention can be produced in a manner that include, or do not include, one or more flavoring ingredients, and that may be contained in a wide variety of different containers, such as a squeezable or non-squeezable tube, a pot, a jar, a can and/or the like, and in a solid, semi-solid or other form, such as a small or large solid stick.

The various ingredients present in the base compositions and active agent-containing compositions of the present invention, including hydrocortisone-containing compositions, and related methods of production and use, are described in detail hereinbelow. They preferably do not include any petroleum jelly (petrolatum), and if they do, the amount of the petroleum jelly is generally in small quantities, generally less than about 5% by weight, and more preferably less than about 4% by weight, and still more preferably less than about 3% by weight, and still more preferably less than about 2% by weight, and even more preferably less than about 1% by weight, and most preferably 0% by weight. They also preferably do not include any water, surfactants, emulsifiers, lidocaine hydrochloride, propylene glycol, aluminum fluoride (or combinations of aluminum and fluoride) or retinol (or retinol derivatives or extracts). If they do include any of the foregoing ingredients, each such ingredient is only generally present in very small quantities, generally less than about 2.5% by weight, and more preferably less than about 2% by weight, and still more preferably less than about 1.5% by weight, and still more preferably less than about 1% by weight, and even more preferably less than about 0.5% by weight, and most preferably 0% by weight.

Hydrocortisone (and/or one or more other active agents) functions as an active agent in the active agent-containing compositions of the invention, and the other ingredients present therein typically collectively form a base, which functions as a topical skin carrier vehicle for the hydrocortisone (and/or other active agents) to be topically applied to the skin of a human being, animal or other mammal. Most or all of the components of the inventive base formulation function together as a blend to bind the various components in the hydrocortisone (and/or other active agent-containing) formulation together in a manner that enables it to be easily, readily, smoothly and properly topically applied to the skin of a mammal, and to penetrate one or a plurality of layers of the skin (usually several or all of them), and/or one or more of the tissues present therein. This permits the hydrocortisone (and/or other active agent) to exhibit its healing and/or other beneficial effects internally and deeply within the structure of the skin, and in significantly deeper areas, tissues and/or layers of the skin than only the top layer (rather than only sitting, resting or laying on the outermost area of the outermost layer of the skin, with no or little penetrating action, as is the case with many other topical skin compositions, including those containing hydrocortisone). As a result, extremely advantageously, the hydrocortisone (and/or other active agent) becomes absorbed and/or adsorbed deep into the various layers and tissues present in the skin of a mammal to a significantly greater and/or deeper extent, and repairs, improves, heals and/or exhibits other beneficial effects in connection with, one or a plurality of internal layers of, and/or tissues present in, the skin (as well as various areas of the uppermost, external, layer of the skin) in a significantly greater extent, in comparison with other hydrocortisone- or active agent-containing topical skin compositions, thereby promoting, and generally providing, excellent skin repair, improvement, treatment and/or healing results.

Via a significant amount of experimentation and testing with the various ingredients of the base compositions of the invention, and with the hydrocortisone-containing and other compositions of the invention, it was determined to be extremely difficult to cause, or have, the ingredients thereof mix together properly, become evenly distributed within the compositions, and form compositions having the beneficial characteristics that are described herein. As one example, it was found to be extremely difficult to include the ingredient Natunola Castor 1023 in the compositions along with the other ingredients present therein in a form of a solid, such as a soft or hard stick, and still have the solid possess one or all of the characteristics that are discussed herein, including an ability of the hydrocortisone (and/or other active agents) present therein to penetrate one or a plurality of the layers of, and/or tissues in, a mammal's skin, and generally be efficacious, and maintain its final form and shape, even when present in extreme environmental conditions, such as freezing, or elevated temperatures, and conditions in which users may carry them on their person, or close to their bodies, and exposed to body heat.

As a result of the above, it was eventually determined that the base compositions and hydrocortisone- (and/or other active agent-) containing compositions typically should include the ingredients that are described herein at the weight percents indicated. When these compositions were produced without one or more of the required ingredients and/or using different weight percents thereof, often a very undesirable product resulted, which did not have component ingredients evenly distributed therein, which could not properly be applied to the skin of a human being, animal or other mammal, which would not penetrate one or a plurality of layers and/or tissues of the skin, which did not have an ability to maintain its shape and/or form under adverse environmental conditions, and/or which did not have one or more of the other beneficial characteristics that are described herein.

Base Composition

The novel base compositions that are described herein, which may be employed with hydrocortisone as an active agent, or with one or a plurality of additional and/or different active ingredients, have surprisingly and unexpectedly been determined via a significant amount of testing and experimentation over a lengthy period of time to be particularly effective as a carrier vehicle for topically applied active agents, such as hydrocortisone (and many other active agents). Its unique formulation of ingredients, and particular weight percents thereof in the formulation, has been found to be particularly effective in promoting or causing a penetration of the active agents(s), along with the base composition, deep within one or more of the various layers and tissues of the skin, including the dermis and epidermis, and maintaining their consistency, form and/or shape (usually all three), such as a solid stick, during extreme environmental conditions, such as extreme heat or cold. Many other base formulations very disadvantageously tend to melt and become liquid-like, messy and/or sloppy during relatively high temperature conditions, such as when left in a hot car during summer months, potentially staining clothing and causing jewelry and other objects to become greasy and/or dirty. These novel base compositions have been determined to be significantly more effective for a topical delivery to the skin of humans beings, animals and/or other mammals of one or a plurality of active agents in comparison with other topically applied skin bases.

The amounts of the various ingredients present in the base compositions of the invention may vary widely, depending upon a variety of factors, such as the particular form and shape that the final topical formulation (including one or more active agents) will have, for example, a solid form, such as a soft or hard stick, a gel, a cream, an ointment and/or the like, the number and types of base ingredients that are employed, the number and types of active agents that are to be employed, and/or the like, and may be determined by those having ordinary skill in the art using the information that is provided herein.

The base formulations of the invention (both original and improved) include FANCOL VB, Natunola Castor 1023, Finsolv TN and bees wax, and optionally one or a plurality of plant oils, fatty alcohols, fats and flavorings, each in amounts that are effective for forming a base having an ability to act effectively as a topical carrier vehicle upon the skin or human beings, animals and/or other mammals for one or more active agents, such as hydrocortisone, preferably in a form of a solid, such as a stick, or semi-solid, and possessing one or more (or all) of the beneficial characteristics that are described herein. In the improved base formulations (and active-agent formulations), it is preferred that the base formulations include one or more plant oils, one or more fatty alcohols and one or more fats, as is discussed herein. Although each of the base ingredients is discussed in greater detail hereinbelow with respect to the compositions of the invention that include one or more active agents, their weight percents in the base compositions of the invention are described directly below.

FANCOL VB

The amount of FANCOL VB that is present in the base compositions is an amount that is effective to cause the base compositions to have one or more of the beneficial characteristics that are described herein, such as causing, or aiding in causing (generally in combination with one or more other ingredients), such base compositions to properly form, or be present in a form of, a solid or semi-solid structure, for example, in the shape of a stick, or any another shape desired or required, or present in a pot or jar.

Original Base Compositions

When none of the above-described optional base ingredients is present in the original base compositions, the amount of FANCOL VB that is present in the base compositions preferably ranges from about 13 to about 25 weight percent, and more preferably ranges from about 16 to about 22 weight percent (with the total base compositions having 100 percent weight). When, however, one or more of such optional base ingredients is present in the original base compositions, the amount of FANCOL VB that is present therein may be much less, such as about 9 weight percent (or possibly even lower, depending upon the number of optional base ingredients included in the base compositions, and the weight percents thereof), and preferably ranges from about 9 to about 13 weight percent, and more preferably ranges from about 10 to about 12 weight percent.

Improved Base Compositions

The amount of FANCOL VB that is present in the improved base compositions of the invention preferably ranges from about 6 to about 25 weight percent, and more preferably ranges from about 6 to about 16 weight percent, and still more preferably ranges from about 10 to about 12 weight percent, and is most preferably about 11 weight percent (whether or not any favoring ingredients are present in the base compositions).

Natunola Castor 1023

The amount of Natunola Castor 1023 that is present in the base compositions is an amount that is effective to cause the base compositions to have one or more of the beneficial characteristics that are described herein, such as causing, or aiding in causing (generally in combination with one or more other ingredients), such base compositions to properly form, or be present in a form of, a solid structure, or semi-solid structure, for example, in the shape of a stick, or any another shape desired or required, or present in a pot or jar.

Original Base Compositions

When none of the above-described optional base ingredients is present in the original base compositions, the amount of Natunola Castor 1023 that is present in the original base compositions preferably ranges from about 23 to about 39 weight percent, and more preferably ranges from about 26 to about 35 weight percent (with the total base compositions having 100 percent weight). When, however, one or more of such optional base ingredients is present in the base compositions, the amount of Natunola Castor 1023 that is present therein may be much less, such as about 16 weight percent (or possibly even lower, depending upon the number of optional base ingredients included in the base compositions, and the weight percents thereof), and preferably ranges from about 16 to about 20 weight percent, and more preferably ranges from about 17 to about 19 weight percent.

Improved Base Compositions

The amount of Natunola Castor 1023 that is present in the improved base compositions of the invention preferably ranges from about 5 to about 39 weight percent, and more preferably ranges from about 5 to about 15 weight percent, and still more preferably ranges from about 9 to about 11 weight percent, and is most preferably about 10 weight percent (whether or not any favoring ingredients are present in the base compositions).

Finsolv TN

The amount of Finsolv TN that is present in the base compositions is an amount that is effective to cause the base compositions to have one or more of the beneficial characteristics that are described herein, such as causing, or aiding in causing (possibly in combination with one or more other ingredients), such base compositions to function as an emollient upon the skin (i.e., to render or make the skin softer than it would have been prior to applying the base compositions thereto).

Original Base Compositions

When none of the above-described optional base ingredients is present in the original base compositions, the amount of Finsolv TN that is present in the original base compositions preferably ranges from about 13 to about 25 weight percent, and more preferably ranges from about 16 to about 22 weight percent (with the total base compositions having 100 percent weight). When, however, one or more of such optional base ingredients is present in the base compositions, the amount of Finsolv TN that is present therein may be much less, such as about 9 weight percent (or possibly even lower, depending upon the number of optional base ingredients included in the base compositions, and the weight percents thereof), and preferably ranges from about 9 to about 13 weight percent, and more preferably ranges from about 10 to about 12 weight percent.

Improved Base Compositions

The amount of Finsolv TN that is present in the improved base compositions of the invention preferably ranges from about 9 to about 25 weight percent, and more preferably ranges from about 10 to about 20 weight percent, and still more preferably ranges from about 14 to about 16 weight percent, and is most preferably about 15 weight percent (whether or not any favoring ingredients are present in the base compositions).

Bees Wax

The amount of bees wax that is present in the base compositions is an amount that is effective to cause the base compositions to have one or more of the beneficial characteristics that are described herein, such as causing, or aiding in causing (generally in combination with one or more other ingredients), such base compositions to properly form, or be present in a form of, a solid structure, or semi-solid structure, for example, in the shape of a stick, or any another shape desired or required, or present in a pot or jar.

Original Base Compositions

When none of the above-described optional base ingredients is present in the original base compositions, the amount of bees wax that is present in the original base compositions preferably ranges from about 26 to about 43 weight percent, and more preferably ranges from about 29 to about 39 weight percent (with the total base compositions having 100 percent weight). When, however, one or more of such optional base ingredients is present in the base compositions, the amount of bees wax that is present therein may be much less, such as about 18 weight percent (or possibly even lower, depending upon the number of optional base ingredients included in the base compositions, and the weight percents thereof), and preferably ranges from about 18 to about 22 weight percent, and more preferably ranges from about 19 to about 21 weight percent.

Improved Base Compositions

The amount of bees wax that is present in the improved base compositions of the invention preferably ranges from about 6 to about 43 weight percent, and more preferably ranges from about 6 to about 16 weight percent, and still more preferably ranges from about 10 to about 12 weight percent, and is most preferably about 11 weight percent (whether or not any favoring ingredients are present in the base compositions).

When only FANCOL VB, Natunola Castor 1023, Finsolv TN and bees wax are present in the base composition, and it is desired to form a solid stick form of the base composition as a topical carrier vehicle for one or more active ingredients, preferred base compositions of the invention includes the weight percents identified below (out of 100 weight percent for the total base) for these four ingredients.

| Ingredient | Weight Percent |
| --- | --- |
| FANCOL VB | 18.333 |
| Natunola Castor 1023 | 30.000 |
| Finsolv TN | 18.333 |
| Bees Wax | 33.334 |
| TOTAL | 100 |

The original and improved base formulations of the present invention optionally (i.e., the weight percent may be 0%), but preferably, also include one or a plurality of plant and/or plant seed oils, such as castor oil, one or a plurality of fatty alcohols, such as stearyl alcohol, one or a plurality of fats, such as cocoa butter, and/or one or a plurality of flavorings, such as vanilla flavoring (and preferably all of them). They, and the compositions of the invention that include one or more active ingredients, may also optionally include a variety of other ingredients, as is discussed hereinbelow.

Plant and Plant Seed Oils

The amount (combined) of one or more plant oils or plant seed oils that are present in the base compositions is an amount that is effective to cause the base compositions to have one or more of the beneficial characteristics that are described herein, such as causing, or aiding in causing (possibly in combination with one or more other ingredients), such base compositions to function as an emollient upon the skin (i.e., to render the skin softer than it would have been prior to applying the base compositions thereto).

Original Base Compositions

When present in the original base compositions, the plant oil(s) and/or plant seed oil(s), such as castor oil, preferably is present in the base compositions in an amount (combined) preferably ranging from about 0.1 to about 24 weight percent, and more preferably ranging from about 8 to about 17 weight percent, and most preferably ranging from about 10 to about 15 weight percent.

Improved Base Compositions

When present in the improved base compositions, the plant oil(s) and/or plant seed oil(s), such as castor oil, preferably is present in the base compositions in an amount (combined) preferably ranging from about 0.1 to about 38.5 (from about 0.1 to about 38.0 if one or more flavoring ingredients are present) weight percent, and more preferably ranging from about 13.5 to about 38.5 (from about 13 to about 38 if one or more flavoring ingredients are present) weight percent, and still more preferably ranging from about 25 to about 27 (from about 24.50 to about 26.50 if one or more flavoring ingredients are present), and is most preferably about 26 (about 25.5 if one or more flavoring ingredients are present) weight percent.

Fatty Alcohols

The amount (combined) of one or more fatty alcohols that is present in the base compositions is an amount that is effective to cause the base compositions to have one or more of the beneficial characteristics that are described herein, such as causing, or aiding in causing (generally in combination with one or more other ingredients), such base compositions to properly form, or be present in a form of, a solid structure, or semi-solid structure, for example, in the shape of a stick, or any another shape desired or required, or present in a pot or jar.

Original Base Compositions

When present in the original base compositions, the fatty alcohol(s), such as stearyl alcohol, preferably is present in the base compositions in an amount (combined) preferably ranging from about 0.1 to about 22 weight percent, and more preferably ranging from about 10 to about 22 weight percent, and most preferably ranging from about 18 to about 22 weight percent.

Improved Base Compositions

When present in the improved base compositions, the fatty alcohol(s), such as stearyl alcohol, preferably is present in the base compositions in an amount (combined) preferably ranging from about 0.1 to about 25 weight percent, and more preferably ranging from about 15 to about 25 weight percent, and still more preferably ranging from about 19 to about 21 weight percent, and is most preferably about 20 weight percent (whether or not any favoring ingredients are present in the base compositions).

Fats

The amount (combined) of one or more fats that is present in the base compositions is an amount that is effective to cause the base compositions to have one or more of the beneficial characteristics that are described herein, such as causing, or aiding in causing (generally in combination with one or more other ingredients), such base compositions to properly form, or be present in a form of, a solid structure, or semi-solid structure, for example, in the shape of a stick, or any another shape desired or required, or present in a pot or jar.

Original Base Compositions

When present in the original base compositions, the fat(s), such as cocoa butter, is preferably present in the base compositions in an amount (combined) preferably ranging from about 0.1 to about 9 weight percent, and more preferably ranging from about 4 to about 9 weight percent, and most preferably ranging from about 6 to about 8 weight percent.

Improved Base Compositions

When present in the improved base compositions, the fat(s), such as cocoa butter, preferably is present in the base compositions in an amount (combined) preferably ranging from about 0.1 to about 12 weight percent, and more preferably ranging from about 2 to about 12 weight percent, and still more preferably ranging from about 6 to about 8 weight percent, and is most preferably about 7 weight percent (whether or not any favoring ingredients are present in the base compositions).

Flavorings

The amount (combined) of one or more flavorings that is present in the base compositions is an amount that is effective to cause the base compositions to: (i) have a pleasant or desirable, or a specific, taste and/or odor, such as a good vanilla taste and odor; (ii) have no, a reduced, or a minimal, unpleasant taste and/or odor (in comparison with how the taste and/or odor would have been if no flavoring(s) had been added); or (iii) have no taste and/or no odor.

Original Base Compositions

When present in the original base compositions, the flavoring(s), such as vanilla flavorings, are present in an amount (combined) preferably ranging from about 0.1 to about 3.5 weight percent, and more preferably ranging from about 0.2 to about 3 weight percent, and most preferably ranging from about 0.4 to about 1 weight percent.

Improved Base Compositions

When present in the improved base compositions, the flavoring(s), such as vanilla flavorings, preferably is present in the base compositions in an amount (combined) preferably ranging from about 0.1 to about 3.5 weight percent, and more preferably ranging from about 0.1 to about 2.5 weight percent, and still more preferably ranging from about 0.3 to about 1.5 weight percent, and is most preferably about 0.5 weight percent.

The inventive base compositions are described herein as a carrier vehicle for hydrocortisone, but may be used with a wide variety of other, or additional, topically applied active agents, such as are described herein.

Typically, one or a plurality of active agents will be combined with the base to form a composition for a topical application to the skin of a mammal in a combined weight percent (of the total weight of the compositions) that is effective for treating, healing (partially or fully) and/or repairing the skin of mammals with respect to a wide variety of different disorders, diseases and/or conditions, such as those that are described herein, or others, and/or causing the skin to feel more soothed, softened and/or conditioned that in did prior to a use of the active agent-containing compositions. The base composition (combination of base ingredients) will typically form the remaining weight percent of the composition.

The amount of a base composition of the invention that is included in a topical active-agent containing skin formulation of the invention may vary widely, depending upon a variety of factors, such as the age, gender, weight and condition of the patient being treated, the medical problem presented by the patient being treated, the particular active agent(s) to be included in the formulation, whether the patient has any additional medical problems or concerns, and/or the like. The amount of the base composition employed is preferably an amount that is effective for acting as a topically applied skin carrier vehicle for the one or more active agents. Such amount will generally be 100 weight percent (total weight of the composition) minus the total weight percent of the combined active agent(s), and typically ranges from about 80 to about 99.9 weight percent, based upon the total weight of the compositions. Such an amount preferably ranges from about 95 to about 99.9 weight percent, more preferably ranges from about 97 to about 99 weight percent and most preferably ranges from about 98 to about 99 weight percent. The amounts of the various ingredients that may be present in the base composition may vary widely depending upon a variety of factors, such as the number of ingredients that are employed, the type of ingredients that are employed and the like, and may readily be determined by those having ordinary skill in the art.

Three preferred base composition of the invention that may be employed with one or a plurality of active agents, such as hydrocortisone, for forming a solid form thereof, such as a stick, and in the methods of the invention, contains the components that are set forth below, and the exact or approximate concentrations thereof (out of 100 weight percent for the total base). The first two base compositions include a flavoring (vanilla) and the third one does not.

Original Base Compositions

| Ingredient | Weight Percent |
| --- | --- |
| FANCOL VB | 11.111 |
| Natunola Castor 1023 | 18.181 |
| FINSOLV TN | 11.111 |
| Bees Wax | 20.202 |
| Castor Oil | 11.616 |
| Stearyl Alcohol | 20.202 |
| Cocoa Butter | 7.070 |
| Flavor | 0.513 |
| TOTAL | 100 |

| Ingredient | Weight Percent |
| --- | --- |
| FANCOL VB | 11 |
| Natunola Castor 1023 | 18 |
| FINSOLV TN | 11 |
| Bees Wax | 20 |
| Castor Oil | 12.5 |
| Stearyl Alcohol | 20 |
| Cocoa Butter | 7 |
| Flavoring | 0.5 |
| TOTAL | 100 |

| Ingredient | Weight Percent |
| --- | --- |
| FANCOL VB | 11 |
| Natunola Castor 1023 | 18 |

-continued

| Ingredient | Weight Percent |
| --- | --- |
| FINSOLV TN | 11 |
| Bees Wax | 20 |
| Castor Oil | 13 |
| Stearyl Alcohol | 20 |
| Cocoa Butter | 7 |
| TOTAL | 100 |

Improved Base Compositions

| Ingredient | Weight Percent |
| --- | --- |
| FANCOL VB | 11.00 |
| Natunola Castor 1023 | 10.00 |
| FINSOLV TN | 15.00 |
| Bees Wax | 11.00 |
| Castor Oil | 25.50 |
| Stearyl Alcohol | 20.00 |
| Cocoa Butter | 7.00 |
| Flavoring (Vanilla) | 0.50 |
| TOTAL | 100 |

| Ingredient | Weight Percent |
| --- | --- |
| FANCOL VB | 11.00 |
| Natunola Castor 1023 | 10.00 |
| FINSOLV TN | 15.00 |
| Bees Wax | 11.00 |
| Castor Oil | 26.00 |
| Stearyl Alcohol | 20.00 |
| Cocoa Butter | 7.00 |
| Flavoring (Vanilla) | 0.00 |
| TOTAL | 100 |

Compositions Including Active Agent(s)

The various ingredients of compositions within the invention that include one or a plurality of active agents, such as hydrocortisone, alone or in combination with one or more other active agents, the weight percents thereof, and preferred compositions of the invention, are discussed below.

Hydrocortisone and/or other Active Ingredients)

Hydrocortisone (also known as Cortisol) is employed in topical compositions within the invention as an active agent to repair (partially—from more than 0% to less than 100%, and preferably fully—about 100%), improve, heal (partially—from more than 0% to less than 100%, and preferably fully—about 100%) and/or treat the various skin disorders, diseases and adverse conditions that are described herein, as well as others, and/or to cause the skin to feel more soothed, softened and/or conditioned than prior to a use of the active agent, either as a sole active agent or alone, or in combination, with one or a plurality of other active ingredients, and either in a pure form or in one or more various known (or other) synthetic, derivative or combination forms, which are known by those having ordinary skill in the art. These forms of hydrocortisone are known under the umbrella of "topical corticosteroids," and have different strengths and formulations, as are known by those having ordinary skill in the art. Many of them are pharmaceutical grade products. Hydrocortisone is, at present, typically only available as a lotion, cream, ointment and in one semi-solid balm product that is specifically designed, and marketed for, the lips.

Hydrocortisone ((11β)-11,17,21-trihydroxypregn-4-ene-3,20-dione) has the chemical formula $C_{21}H_{30}O_5$, and the chemical structure that is shown below, and is the primary steroid hormone or glucocorticoid that is produced by the adrenal cortex of the adrenal gland.

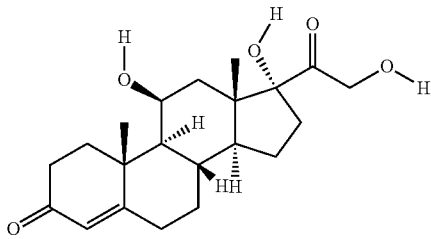

Hydrocortisone is generally released by the body in response to stress and to a low level of blood glucocorticoids, and its primary functions are to suppress the immune system, increase blood sugar through gluconeogenesis and aid in fat, protein and carbohydrate metabolism.

Various synthetic and other forms of hydrocortisone may be used to treat a variety of different disorders, diseases, adverse conditions and/or illnesses, either as an injection or topically, for example, in a treatment of inflammation, redness, allergy, itching, collagen diseases, asthma, adrenocortical deficiency, shock, and some neoplastic conditions.

When applied topically to the skin, hydrocortisone often reduces or terminates the actions of various chemicals in the bodies of human and non-human mammals that cause inflammation, redness, swelling, blisters, itching and/or the like. It is useful for treating and healing one or a plurality of disorders of the skin, which may be caused by a number of different conditions or factors, including, but not limited to, a wide variety of skin inflammatory conditions, redness, swelling, blisters, burns, cuts, punctures (and other skin perforations), bug bites, razor bumps, chronic (or other) dermatitis, irritant dermatitis, contact dermatitis, seborrheic dermatitis, stasis dermatitis, acne excoriee, many skin complications resulting from acne, allergic reactions, insect bites, trauma, perleche, eczema, eczema craquele, psoriasis, xerosis, genital skin disorders, poison ivy, poison oak, general itching, a presence of microbes (bacteria, viruses, and/or the like), disease related skin conditions and dryness from medications such as isotretinoin, acitretin and lipid lowering agents, and/or the like.

Hydrocortisone USP (United States Pharmacopeia), and other forms of hydrocortisone, are commercially available from sources that are known by those having ordinary skill in the art, for example, from Spectrum Chemical Mfg. Corp. (Gardena, Calif.) and Pfizer CentreSource (Kalamazoo, Mich.).

The amount (combined) of the one or more active agents, such as hydrocortisone (alone or in combination with one or more other active agents), that may be employed in the active agent-compositions of the present invention is an amount that is effective, when present in a base composition described herein, to promote, encourage or cause a partial or total repair, improvement, healing, treatment or other beneficial effect in connection with a skin disorder, disease, adverse condition, malady and/or the like, as they are discussed herein in detail (or otherwise). The amount (combined) of the one or more active agents that is preferably incorporated into, or otherwise formulated with, the base compositions of the invention will generally be 100 weight percent (total weight of the composition) minus the total weight percent of the base composition (including all ingredients, and combined amounts thereof, employed in the base composition). For the original active-agent containing compositions of the invention, such an amount preferably ranges from about 0.1 to about 5 weight percent, based upon the total weight of the compositions, and more preferably ranges from about 0.5 to about 3 weight percent, and even more preferably ranges from about 0.8 to about 2 weight percent, and most preferably is about 1 weight percent. For the improved active-agent containing compositions of the invention, such an amount preferably ranges from about 0.1 to about 5 weight percent, based upon the total weight of the compositions, and more preferably ranges from about 0.5 to about 3 weight percent, and even more preferably ranges from about 0.8 to about 2 weight percent, and still more preferably ranges from about 0.9 to about 1.5 weight percent, and even more preferably ranges from about 0.95 to about 1.2 weight percent, and most preferably is about 1.0 weight percent.

Additional information about hydrocortisone and/or its uses is present in *Hydrocortisone—A Medical Dictionary, Bibliography and Annotated Research Guide to Internet References* (ICON Health Publications, ISBN-10: 0497005581, 2004); *Hydrocortisone: Webster's Timeline History, 1950-2007* (ICON Group International, Inc., ASIN: B003N2QNFS, 2010); *Hydrocortisone and Cortisone* (Merck & Co., ASIN: B000GSVX48, 1956); and Francis D. W. Lukins, *Medical Uses of Cortisone including Hydrocortisone and Corticotropin* (The Blakiston Company, ASIN: B000SAR10W, 1954).

One or a plurality of a wide variety of topical active ingredients other than hydrocortisone, or in addition to hydrocortisone, alone or in a combination with one or more other active agents, such as one or a plurality of steroids other than hydrocortisone, antibiotics, antifungals, antihistamines, anti-inflammatories, local anesthetics, anti-itch agents and/or the like, may alternately, or additionally, be included in the active-agent containing topical compositions of the invention, and produced in the manner described herein, to treat, repair, improve and/or heal (fully or partially) a same or similar, or different, skin disease, disorder, condition and/or the like, and/or to provide one or a plurality of other (different) beneficial effects to the skin of a human being, animal and/or other mammal. These active ingredients include, but are not limited to, clindamycin (topical antibiotic), erythromycin (topical antibiotic), neomycin (topical antibiotic), tretinoin (topical retinoid), doxepin (topical antihistamine), flurandrenolide (topical corticosteroid), terbinafine (topical antifungal), permethrin (insecticide), malathion (insecticide), silver sulfadiazine (antiseptic), salicyclic acid (keratolytic), and various herbal agents. The foregoing are only a few examples of the numerous different active agents that may be employed in the compositions of the invention, alone or in combination. Such active ingredients are known by those having ordinary skill in the art, and also are described in sources that are known by those having ordinary skill in the art, such as in Maryadele J. O'Neil, *The Merck Index, an Encyclopedia of Chemicals, Drugs and Biologicals* (Merck, 14th Edition, ISBN 091191000X, 2006) and in *PDR: The Physician's Desk Reference* 2010 (PDR Network, LLC, ISBN-10: 1563637480, 2009).

Active ingredients that may be employed with, or in, the base compositions of the invention, and in the active agent-containing compositions of the invention, include, but are not limited to, those that are identified below, and those that may be invented, developed and/or produced in the future, alone or in any combination (including all of the various and/or alternative chemical, brand, trade, generic and/or other names that are, or may be, employed to identify each active ingredient, which are known by those having ordinary skill in the art). Sources for these active ingredients are described herein and are known by those having ordinary skill in the art.

Topical Steroids
Clobetasol propionate 0.05% (Dermovate)
Betamethasone dipropionate 0.25% (Diprolene)
Halobetasol proprionate 0.05% (Ultravate)
Diflorasone diacetate 0.05% (Psorcon)
Fluocinonide 0.05% (Lidex)
Halcinonide 0.05% (Halog)
Amcinonide 0.05% (Cyclocort)
Desoximetasone 0.25% (Topicort)
Triamcinolone acetonide 0.5% (Kenalog, Aristocort cream)
Mometasone furoate 0.1% (Elocon ointment)
Fluticasone propionate 0.005% (Cutivate)
Betamethasone dipropionate 0.05% (Diprosone)
Fluocinolone acetonide 0.01-0.2% (Synalar, Synemol, Fluonid)
Hydrocortisone valerate 0.2% (Westcort)
Hydrocortisone butyrate 0.1% (Locoid)
Flurandrenolide 0.05% (Cordran)
Triamcinolone acetonide 0.1% (Kenalog, Aristocort A ointment)
Mometasone furoate 0.1% (Elocon cream, lotion)
Triamcinolone acetonide 0.1% (Kenalog, Aristocort cream, lotion)
Fluticasone propionate 0.05% (Cutivate cream)
Desonide 0.05% (Tridesilon, DesOwen ointment)
Fluocinolone acetonide 0.025% (Synalar, Synemol cream)
Hydrocortisone valerate 0.2% (Westcort cream)
Prednicarbate 0.05% (Aclovate cream, ointment)
Triamcinolone acetonide 0.025% (Aristocort A cream, Kenalog lotion)
Fluocinolone acetonide 0.01% (Capex shampoo, Dermasmooth)
Desonide 0.05% (DesOwen cream, lotion)
Hydrocortisone 2.5% (Hytone cream, lotion, ointment)
Hydrocortisone 1%
Topical Antibiotics/Anti-Infectives
Topical erythromycin (ATS and others)
Topical mupirocin (Bactroban)
Topical retapamulin (Altabax)
Topical bacitracin/polymyxin B (Polysporin)
Topical bacitracin/neomycin/polymyxin B (Neosporin)
Topical sulfacetamide sodium/urea (Sulfa drugs)
Topical Antifungals
Natamycin
Rimocidin
Filipin
Nystatin
Amphotericin B
Candicin
Hamycin
Miconazole, miconazole nitrate (Micatin)
Ketoconazole (Nizoral, Sebizole)
Clotrimazole (Lotriminm, Lotrimin AF, Canesten)
Econazole
Bifonazole
Butoconazole
Fenticonazole
Isoconazole Oxiconazole
Sertaconazole (Ertaczo)
Sulconazole
Tioconazole
Fluconazole
Itraconazole
Isavuconazole
Ravuconazole
Posaconazole
Voriconazole
Terconazole
Abafungin
Terbinafine (Lamisil)
Naftifine (Naftin)
Butenafine (Lotrimin Ultra)
Anidulafungin
Caspofungin
Micafungin
Polygodial
Ciclopirox, ciclopirox olamine
Tolnaftate (Tinactin, Desenex, Aftate)
Undecylenic acid
Flucytosine, 5-fluorocytosine
Griseofulvin
Haloprogin
Sodium bicarbonate
Topical Immunomodulators
Pimecrolimus 1% Cream (Elidel)
Tacrolimus 0.1% ointment (Protopic)
Topical Antihistamines
Clemastine
Diphenhydramine (Benadryl)
Doxylamine
Loratadine
Desloratadine
Fexofenadine
Pheniramine
Cetirizine
Ebastine
Promethazine
Chlorpheniramine
Levocetirizine
Olopatadine
Quetiapine
Meclizine
Dimenhydrinate
embramine
dimethindene
dexchlorpheniramine
Vitamin C (Ascorbic acid)
Cimetidine
Famotidine
Ranitidine
Nizatidine
Roxatidine
Lafutidine
A-349,821
ABT-239
Ciproxifan
Clobenpropit
Thioperamide
Thioperamide
JNJ 7777120
VUF-6002
Cromoglicate (Cromolyn)
Nedocromil
β2 adrenergic agonists Topical Analgesics
    Acetaminophen (Tylenol)
    Diclofenac (Cataflam, Voltaren)
    Diflunisal (Dolobid)
    Etodolac (Lodine, Lodine XL)
    Fenoprofen (Nalfon)
    Flurbiprofen (Ansaid)
    Ibuprofen (Advil, Cramp End, Dolgesic, Excedrin IB, Genpril, Haltran, Ibren, Ibu, Ibuprin, Ibuprohm, Ibu-Tab, Medipren, Midol IB, Motrin, Nuprin, Pamprin-IB, Q-Profen, Rufen, Trendar)
    Indomethacin (Indocin, Indocin SR)
    Ketoprofen (Actron, Orudis, Oruvail)
    Ketorolac (Toradol)
    Meclofenamate (Meclomen)
    Mefenamic Acid (Ponstel)
    Meloxicam (Mobic)
    Nabumetone (Relafen)
    Naproxen (Aleve, Anaprox, Anaprox DS, EC-Naprosyn, Naprelan, Naprosyn)
    Oxaprozin (Daypro)
    Phenylbutazone (Cotylbutazone)
    Piroxicam (Feldene)
    Sulindac (Clinoril)
    Tolmetin (Tolectin, Tolectin DS)
    Celecoxib (Celebrex)
    Buprenorphine (Buprenex)
    Butorphanol (Stadol)
    Codeine
    Hydrocodone
    Hydromorphone (Dilaudid, Dilaudid-5, Dilaudid-HP, Hydrostat IR)
    Levorphanol (Levo-Dromoran)
    Meperidine (Demerol)
    Methadone (Dolophine, Methadose)
    Morphine (Astramorph PF, AVINZA, Duramorph, Kadian, M S Contin, MSIR, Oramorph SR, Rescudose, Roxanol)
    Nalbuphine (Nubain)
    Oxycodone (OxyContin, Roxicodone)
    Oxymorphone (Numorphan)
    Pentazocine (Talwin)
    Propoxyphene (Cotanal-65, Darvon)
    Tramadol (Ultram)
    Tramadol and Acetaminophen (Ultracet)
    Butalbital, Acetaminophen, and Caffeine (Femcet, Fioricet, Esgic, Esgic-Plus)
    Butalbital, Aspirin, and Caffeine (Fiorinal)
    Butalbital, acetaminophen, caffeine, and codeine (Fioricet with Codeine)
    Hydrocodone and Ibuprofen (Hydrostal IR, Vicoprofen)
    Pentazocine/Naloxone (Talwin NX)
    Acetaminophen and Codeine (Capital with Codeine, Margesic #3, Phenaphen with Codeine, Tylenol with Codeine)
    Dihydrocodeine, Acetaminophen, and Caffeine (DHC-plus)
    Hydrocodone and Acetaminophen (Allay, Anexsia 5/500, Anexsia 7.5/650, Dolacet, Dolagesic, Duocet, Hycomed, Hydrocet, Hydrogesic, HY—PHEN, Lorcet 10/650, Lorcet-HD, Lortab, Panacet 5/500, Panlor, Stagesic, T-Gesic, Ugesic, Vicodin, Zydone)
    Oxycodone and Acetaminophen (Endocet, Percocet, Roxicet, Roxilox, Tylox)
    Pentazocine and Acetaminophen (Talacen)
    Propoxyphene and Acetaminophen (Darvocet-N 50, Darvocet-N 100, E-Lor, Propacet 100)
    Aspirin, Caffein and Dihydrocodeine (Synalgos-DC)

Aspirin and Codeine (Empirin with Codeine)
Hydrocodone and Aspirin (Damason-P, Lortab ASA, Panasal 5/500)
Oxycodone and Aspirin (Endodan, Percodan, Percodan-Demi, Roxiprin)
Pentazocine and Aspirin (Talwin Compound)
Propoxyphene, Aspirin, and Caffeine (Darvon Compound 65, PC-Cap, Propoxyphene Compound 65)
Capsaicin (ArthriCare, ARTH-RX, Axsain, Capsagel, Dura-Patch, Methacin, Zotrix, Zotrix-HP)
Benzocaine (Americaine, Endocaine, Lagol)
Benzocaine/Menthol (Benzocol, Butyl Aminobenzoate, Dermoplast)
Dibucaine (Cinchocaine, Nupercainal Cream, Nupercainal Ointment)
Lidocaine (LidaMantle, Lidoderm, Lignocainem, Xylocalne)
Lidocaine/Prilocalne (EMLA)
Topical Neurotoxins
onabotulinumtoxinA (Botox)
abobotulinumtoxinA (Dysport)
incobotulinumtoxinA (Xeomin)
Botulinum Toxin Type A (Purtox)
Topical Insect Repellents
DEET (N,N-diethyl-m-toluamide)
Essential Oil (Corymbia citriodora/p-menthane-3,8-diol [PMD])
Icaridin (Picaridin, Bayrepel, KBR 3023)
Nepetalactone (Catnip Oil)
Citronella oil
Permethrin
Neem oil
Bog Myrtle
IR 3535 (3-[N-Butyl-N-acetyl]-aminopropionic acid, ethyl ester)
Sunscreen Active Ingredients
p-Aminobenzoic acid (PABA)
Padimate O (OD-PABA, octyldimethyl-PABA or σ-PABA)
Phenylbenzimidazole sulfonic acid (Ensulizole, Eusolex 232, PBSA or Parsol HS)
Cinoxate (2-Ethoxyethyl p-methoxycinnamate)
Dioxybenzone (Benzophenone-8)
Oxybenzone (Benzophenone-3, Eusolex 4360 or Escalol 567)
Homosalate (Homomethyl salicylate or HMS)
Menthyl anthranilate (Meradimate)
Octocrylene (Eusolex OCR, 2-cyano-3,3diphenyl acrylic acid, or 2-ethylhexylester)
Octyl methoxycinnamate (Octinoxate, EMC, OMC, Ethylmethoxycinnamate, Escalol 557, 2-ethylhexyl-paramethoxycinnamate or Parsol MCX)
Octyl salicylate (Octisalate, 2-Ethylhexyl salicylate or Escalol 587)
Sulisobenzone (2-Hydroxy-4-Methoxybenzophenone-5-sulfonic acid, 3-benzoyl-4-hydroxy-6-methoxybenzenesulfonic acid, Benzophenone-4 or Escalol 577)
Trolamine salicylate (Triethanolamine salicylate)
Avobenzone (1-(4-methoxyphenyl)-3-(4-tert-butylphenyl)propane-1,3-dione, Butyl methoxy dibenzoylmethane, BMDBM, Parsol 1789 or Eusolex 9020)
Ecamsule (Mexoryl SX or Terephthalylidene Dicamphor Sulfonic Acid)
Titanium dioxide (CI77891)
Zinc oxide
4-Methylbenzylidene camphor (Enzacamene, Parsol 5000, Eusolex 6300 or MBC)
Tinosorb M (Bisoctrizole, Methylene Bis-Benzotriazolyl, Tetramethylbutylphenol or MBBT)
Tinosorb S (Bis-ethylhexyloxyphenol methoxyphenol triazine, Bemotrizinol, BEMT or anisotriazine)
Neo Heliopan AP (Bisdisulizole Disodium, Disodium phenyl dibenzimidazole tetrasulfonate, bisimidazylate or DPDT)
Mexoryl XL (Drometrizole Trisiloxane)
Benzophenone-9 (Uvinul DS 49, CAS 3121-60-6 or Sodium Dihydroxy Dimethoxy Disulfobenzophenone)
Uvinul T 150 (Octyl triazone, ethylhexyl triazone or EHT)
Uvinul A Plus (Diethylamino Hydroxybenzoyl Hexyl Benzoate)
Uvasorb HEB (Iscotrizinol, Diethylhexyl butamido triazone or DBT)
Parsol SLX (Dimethico-diethylbenzalmalonate, Polysilicone-15)
Isopentenyl-4-methoxycinnamate (Isoamyl p-Methoxycinnamate, IMC, Neo Heliopan E1000, Amiloxate)

FANCOL VB

FANCOL VB (also known as FANCOL or *Butyrospermum Parkii* Butter *Limnanthes Alba* Seed Oil) is employed as a base ingredient in the base compositions of the invention, and in the topical active agent-containing compositions of the invention, and functions primarily to cause, or aid in causing (generally in combination with one or more other ingredients), such compositions to properly form, or be present in a form of, a solid or semi-solid structure (preferably a solid stick), but may also function to moisturize, condition and/or protect the epidermal and/or other layers of the skin, to promote skin pigment wetting, skin penetration of active agents, spreadability on the skin, skin shine and/or binding of various composition ingredients together.

FANCOL VB consists of vegetable derived lipids and sterol enriched shea butter extract. Its INCI name is *Limnanthes Alba* (Meadowfoam) Seed Oil, *Butyrospermum Parkii* (Shea Butter) Extract, and it preferably has the chemical and physical data shown below.

Chemical and Physical Data

Color (Gardner) 3 max.
Saponification Value 175 max.
Iodine Value 105 max.
Acid Value 0.5 max.

The solubility of FANCOL VB in various other ingredients or compositions at both 25° C. and 75° C. is shown below.

Solubility of FANCOL VB at 25° C. and 75° C.

| Composition | 25° C. | 75° C. |
| --- | --- | --- |
| Castor Oil | Soluble (Clear Solution) | Soluble (Clear Solution) |
| Mineral Oil | Soluble (Clear Solution) | Soluble (Clear Solution) |
| Propylene Glycol | Insoluble | Insoluble |
| Glycerine | Insoluble | Insoluble |
| Ethyl Acetate | Soluble (Clear Solution) | Soluble (Clear Solution) |
| Ethyl Alcohol | Insoluble | Soluble (Clear Solution) |
| Water | Insoluble | Slightly Soluble |

-continued

| Composition | 25° C. | 75° C. |
|---|---|---|
| Isopropyl Myristate | Soluble (Clear Solution) | Soluble (Clear Solution) |

FANCOL VB is commercially available from sources that are known by those having ordinary skill in the art, for example, from The Fanning Corporation (Chicago, Ill.) or Elementis Specialties, Inc. (Hightstown, N.J.).

The amount of FANCOL VB that is present in the active agent-containing compositions of the invention is an amount that is effective to cause the compositions to have one or more of the beneficial characteristics that are described herein, such as causing, or aiding in causing (generally in combination with one or more other ingredients), such compositions to properly form, or be present in a form of, a solid structure, or semi-solid structure, or example, in the shape of a solid stick (i.e., cylinder shaped), or any another shape desired or required, or present in a pot or jar.

Original Active Agent-Containing Compositions

When none of the above-described optional base ingredients is present in the original active agent-containing compositions of the invention, the amount of FANCOL VB that is present in these compositions preferably ranges from about 13 to about 25 weight percent, and more preferably ranges from about 16 to about 22 weight percent (with the total compositions having 100 percent weight). When, however, one or more of such optional base ingredients is present in these compositions, the amount of FANCOL VB that is present therein may be much less, such as about 9 weight percent (or possibly even lower, depending upon the number of optional base ingredients included in these compositions, and the weight percents thereof), and preferably ranges from about 9 to about 13 weight percent, and more preferably ranges from about 10 to about 12 weight percent.

Improved Active Agent-Containing Compositions

The amount of FANCOL VB that is present in the improved active agent-containing compositions of the invention preferably ranges from about 6 to about 25 weight percent, and more preferably ranges from about 6 to about 16 weight percent, and still more preferably ranges from about 10 to about 12 weight percent, and is most preferably about 11 weight percent (whether or not any favoring ingredients are present in the compositions).

Additional information about FANCOL VB is present at the Elementis Specialties, Inc. Internet web site and at other web sites known by those having ordinary skill in the art.

Natunola Castor 1023

Natunola Castor 1023 (INCI name *Ricinus Communis* (Castor) Seed Oil (and) *Glycine Soja* (Soybean) Germ Extract (and) *Zea Mays* (Corn) Starch (and) Silica,) is employed as a base ingredient in the compositions of the invention, and in the topical active agent-containing compositions of the invention. It functions primarily to cause, or aid in causing (generally in combination with one or more other ingredients), such compositions to properly form, or be present in a form of, a solid or semi-solid structure (preferably a solid stick), but may also function to soften the skin and to bind various composition ingredients together, and typically resists oxidation, and has a high degree of stability.

Natunola Castor 1023 is a glossy gel that is derived from castor oil (*ricinus communis*) which, in turn, is derived from the bean of the Castor plant *Ricinus communis*, and is the primary component within Natunola Castor 1023, with the other components being glycerine soybean germ extract, corn starch and silica. It typically has the following characteristics:

Characteristics

Appearance: clear, transparent gel
Odor: light, characteristic
Solubility: soluble in all vegetable oils, glycerol tri-isostearate, isostearyl isostearate, oleic acid, isostearic acid, coco-caprylate/caprate and mixed glycerides; insoluble in water silicone oil; partially soluble in ethanol and 1,2propanediol
pH (1:20 water emulsion): 4.6-6.6
Stability: Stable at room temperature
Formulating pH: a pH range of from about 3 to about 8 is preferred
Formulating Temperature: a working temperature range of from about 45° C. to about 95° C. is preferred Natunola Castor 1023 is commercially available from sources that are known by those having ordinary skill in the art, for example, from Natunola Health Biosciences, Inc. (Winchester, Ontario, Canada) or Natunola Health, Inc. (Winchester, Ontario, Canada), or distributors or retailers thereof, which are known by those having ordinary skill in the art.

The amount of Natunola Castor 1023 that is present in the active agent-containing compositions of the invention is an amount that is effective to cause the compositions to have one or more of the beneficial characteristics that are described herein, such as causing, or aiding in causing (generally in combination with one or more other ingredients), such compositions to properly form, or be present in a form of, a solid or semi-solid structure, for example, in the shape of a stick, or in any another shape desired or required, or present in a pot or jar.

Original Active-Agent Containing Compositions

When none of the above-described optional base ingredients is present in the original active agent-containing compositions of the invention, the amount of Natunola Castor 1023 that is present in these compositions preferably ranges from about 23 to about 39 weight percent, and more preferably ranges from about 26 to about 35 weight percent (with the total compositions having 100 percent weight). When, however, one or more of such optional base ingredients is present in these compositions, the amount of Natunola Castor 1023 that is present therein may be much less, such as about 16 weight percent (or possibly even lower, depending upon the number of optional base ingredients included in these compositions, and the weight percents thereof), and preferably ranges from about 16 to about 20 weight percent, and more preferably ranges from about 17 to about 19 weight percent.

Improved Active Agent-Containing Compositions

The amount of Natunola Castor 1023 that is present in the improved active agent-containing compositions of the invention preferably ranges from about 5 to about 39 weight percent, and more preferably ranges from about 5 to about 15 weight percent, and still more preferably ranges from about 9 to about 11 weight percent, and is most preferably about 10 weight percent (whether or not any favoring ingredients are present in the compositions).

Additional information about Natunola Castor 1023 is present at a Natunola Health Biosciences, Inc. or Natunola Health, Inc. Internet web site and at other web sites known by those having ordinary skill in the art.

Finsolv TN

Finsolv TN (INCI name $C_{12-15}$ Alkyl Benzoate, CAS Registry Number 68411-27-8, EINECS Number 270-1,2-4, also known as Finsolv) is employed as a base ingredient in the compositions of the invention, and in the topical active agent-containing compositions of the invention, and functions primarily as an emollient, but may also function to as a binder (to bind composition ingredients together), a thickening agent, a dispersing aid and/or a lubricant therein. $C_{12-15}$ Alkyl Benzoate is the ester of benzoic acid and $C_{12-15}$ alcohols (q.v.), and conforms to a formula below in which R represents a $C_{12-15}$ alkyl group ($C_{12}$, $C_{13}$, $C_{14}$ and/or $C_{15}$):

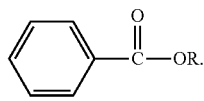

Finsolv TN is an emollient ester that typically is non-toxic, non-irritating, non-sensitizing, water insoluble, readily emulsifiable and stable over a wide pH range, and has a high positive spreading coefficient. It typically has the following properties:

Properties

Appearance: clear, almost colorless liquid
Odor: very mild, and practically odorless
Boiling Point: 300° C. (572° F.)
Pour Point: 14° C. (approximately)
Freezing Point Range: −3 to −12° C.
Flash Point: 163-166° C.
Specific Gravity at 25° C.: 0.928
Refractive Index at 20° C.: 1.485
Surface Tension at 15° C.: 31.5 dynes/cm
Interfacial Tension in Water at 15° C.: 7.13 dynes/cm
Spreading Coefficient at 15° C.: 34.5 dynes/cm
Viscosity (Brookfield at 70° F., RV #1 Spindle, 100 RPM): 38 cps
Acidity (mg KOH/g): <0.10%
% Moisture: <0.10

Finsolv TN is commercially available from sources that are known by those having ordinary skill in the art, for example, from Finetex, Inc. (Elmwood Park, N.J.) or Innospec Active Chemicals, LLC (Edison, N.J.).

The amount of Finsolv TN that is present in the active agent-containing compositions of the invention is an amount that is effective to cause the compositions to have one or more of the beneficial characteristics that are described herein, such as causing, or aiding in causing (possibly along with one or more other ingredients), such compositions to function as an emollient upon the skin (i.e., to render the skin more soft than it would have been prior to applying the compositions thereto).

Original Active-Agent Containing Compositions

When none of the above-described optional base ingredients is present in the original active agent-containing compositions of the invention, the amount of Finsolv TN that is present in these compositions preferably ranges from about 13 to about 25 weight percent, and more preferably ranges from about 16 to about 22 weight percent (with the total compositions having 100 percent weight). When, however, one or more of such optional base ingredients is present in these compositions, the amount of Finsolv TN that is present therein may be much less, such as about 9 weight percent (or possibly even lower, depending upon the number of optional base ingredients included in these compositions, and the weight percents thereof), and preferably ranges from about 9 to about 13 weight percent, and more preferably ranges from about 10 to about 12 weight percent.

Improved Active Agent-Containing Compositions

The amount of Finsolv TN that is present in the improved active agent-containing compositions of the invention preferably ranges from about 9 to about 25 weight percent, and more preferably ranges from about 10 to about 20 weight percent, and still more preferably ranges from about 14 to about 16 weight percent, and is most preferably about 15 weight percent (whether or not any favoring ingredients are present in the compositions).

Additional information about Finsolv TN is present at an Innospec Active Chemicals, LLC Internet web site and at other web sites known by those having ordinary skill in the art.

Bees Wax

Bees wax (also known as *Cera alba* and *Cera flava*) is employed as a base ingredient in the compositions of the invention, and in the topical active agent-containing compositions of the invention, and it functions primarily to cause, or aid in causing (generally in combination with one or more other ingredients), such compositions to properly form, or be present in a form of, a solid structure (preferably a solid stick), but may also function as a moisturizing agent, a softening agent, a thickening agent, an emollient (skin softener) and/or a provider of skin protective action (of the nonoclusive type). It typically protects the skin from, for example, damaging environmental factors, such as chemicals, adverse weather conditions, and the like, by providing skin with a protective coating against environmental elements. Bees wax permits, or helps permit, the compositions of the invention to be formulated into a desired form and shape, such as a stick that is soft, somewhat rigid or relatively hard (generally firm and/or very rigid), such as a traditional ChapStick® form. It also functions as a binder (helping to bind all of the composition ingredients together).

Bees wax is generally a colorless, nutrient-rich, liquid lipid that is secreted from special abdominal glands of honey bee, *Apis Mellifera*, generally as they build honeycomb walls, and transforms into a semi-solid substance upon contact with the atmosphere. It typically is non-allergenic and has water repellent properties, and may be purified from its raw state by freeing it of solid impurities by melting and centrifugation. Bees wax typically contains from about 10 to about 15 percent paraffin carbohydrates, from about 35 to about 37 percent esters of $C_{16}$ to $C_{36}$ fatty acids and about 15 percent cerotic acid, melis sic acid and their homologues. Typically, bees wax has a melting point of from about 62° C. to about 65° C., has an acid value of from about 17 to about 24, has a saponification value of from about 89 to about 103, and has an ester value of from about 72 to about 79.

Bees wax is commercially available from sources that are known by those having ordinary skill in the art, for example, from Columbus Foods Company (Des Plaines, Ill.) or Hangzhou Golden Harvest Health Industry Co., Ltd. (Zhejiang, China).

The amount of bees wax that is present in the active agent-containing compositions of the invention is an amount that is effective to cause the compositions to have one or more of the beneficial characteristics that are described herein, such as causing, or aiding in causing (generally in combination with one or more other ingredients), such compositions to properly form, or be present in a form of, a solid or semi-solid structure, for example, in the shape of a stick or any another shape desired or required, or present in a pot or jar.

Original Active-Agent Containing Compositions

When none of the above-described optional base ingredients is present in the original active agent-containing compositions of the invention, the amount of bees wax that is present in these compositions preferably ranges from about 26 to about 43 weight percent, and more preferably ranges from about 29 to about 39 weight percent (with the total compositions having 100 percent weight). When, however, one or more of such optional base ingredients is present in these compositions, the amount of bees wax that is present therein may be much less, such as about 18 weight percent (or possibly even lower, depending upon the number of optional base ingredients included in these compositions, and the weight percents thereof), and preferably ranges from about 18 to about 22 weight percent, and more preferably ranges from about 19 to about 21 weight percent.

Improved Active Agent-Containing Compositions

The amount of bees wax that is present in the improved active agent-containing compositions of the invention preferably ranges from about 6 to about 43 weight percent, and more preferably ranges from about 6 to about 16 weight percent, and still more preferably ranges from about 10 to about 12 weight percent, and is most preferably about 11 weight percent (whether or not any favoring ingredients are present in the compositions).

Additional information about bees wax is present in, for example, Roger A. Morse et al., "*Beeswax: Production, Harvesting, Processing and Products*" (Wicwas Pr, 1st Edition, ISBN-10: 1878075063, 1984); and Huber H. Root, "*Beeswax: Its Properties, Testing, Production and Applications*" (Chemical Pub. Co., ASIN: B0007E742G, 1951).

Plant and Plant Seed Oils

One or a plurality of plant or plant seed oils (i.e., oils procured or derived from one or more parts of a plant, shrub or tree, such as a root, stem, bark, leaf, flower, seed, fruit and/or the like) (or other similar oils) are optionally, but preferably, employed as a base ingredient in the base compositions of the invention, and in the topical active agent-containing compositions of the invention, and functions primarily as an emollient (skin softener), but may also function as a lubricant and/or binder. Preferred plant or plant seed oils for use in the base and active agent-containing compositions of the invention include Castor Oil, Rice Brand Oil, Coconut Oil, Sunflower Oil and Olive Oil, with Castor Oil being the most preferred such oil, and is preferably present therein (without other plant or plant seed oils). A wide variety of plant and plant seed oils are known by those having ordinary skill in the art and/or are described elsewhere herein and below.

Plant and plant seed oils (or possibly fats in some cases) that may be employed in the base and other compositions of the invention include, but are not limited to, Soybean Oil, Rapeseed Oil, Cottonseed Oil, Sunflower Seed Oil, Ground Nut Oil, Palm Oil, Palm Kernel Oil, Peanut Oil, Copra Oil, Sesame Oil, Sesame Seed Oil, Linseed Oil, Castor Oil, Maize Oil, Coconut Oil, Olive Oil, Almond Oil, Coffee Oil, Costus Root Oil, Agarwood (*Aquilaria Malaccensis*)(Agar) Oil, *Angelica Archangelica* (Angelica Root) Oil, Apricot Kernel Oil, *Artemisia Dracunculus* (Tarragon) Oil, *Artemisia Pallens* (Davana) Oil, Asafoetida Oil, Avocado Oil, Babassu Oil, Basil Oil, Bay Oil, Bergamot Oil, Birch Oil, Borage Oil, Buchu Shrub (Buchu) Oil, Calamus Root Oil, *Calendula* Oil, Camellia Oil, Camphor Oil, *Cannabis* Flower Essential Oil, Canola Oil, Caraway Oil, Carrot Seed Oil (Essential Oil), *Carum Copticum* (Ajwain) Oil, Cedarwood Oil, Cetyl Rinoleate, Chamomile Oil, Cinnamon Oil, Cistus Species Oil, Citronella Oil, Clary Sage Oil, Clove Leaf Oil, Coconut Oil, *Cocos Nucifera* (Coconut) Oil, Coriander Oil, Corn Oil, Costus Root Oil, Cranberry Seed Oil, Cumin Oil, Black Seed Oil, Curry Leaf Oil, Cypress Oil, Cypriol Oil, Dill Oil, Elecampane Oil, *Elettaria Cardamomum* (Cardamom) Seed Oil, Emu Oil, Ethyl Ricinoleate Oil, *Eucalyptus Globulus* (Eucalyptus) Leaf Oil, *Eugenia Caryophyllus* (Clove) Flower Oil, Evening Primrose Oil, Fennel Seed Oil, Fenugreek Oil, Fir Oil, Flax (Linseed) Oil, Florentine Iris (Iris Florentina) (Orris) Oil, Frankincense Oil, Galangal Oil, Galbanum Oil, Geranium Oil, Ginger Oil, Glyceryl Ricinoleate, Glyceryl Ricinoleate Se, Glycol Ricinoleate, Goldenrod Oil, Grapefruit Oil, Grapeseed Oil, Hazelnut Oil, *Helichrysum* Oil, Hemp Seed Oil, Henna Oil, Horseradish Oil, Hydrogenated Castor Oil, Hyssop Oil, Idaho Tansy Oil, *Illicium Verum* (Anise) Oil, Illipe Oil, Isopropyl Ricinoleate, Jasmine Oil, Jojoba Oil, Juniper Berry Oil, Kukui Nut Oil, Laurus Nobilis Oil, Lavender Oil, Ledum Oil, Lemongrass Oil, Lime Oil, Litsea Cubeba Oil, Macadamia Nut Oil, Marjoram Oil, Meadowfoam Oil, *Melaleuca Alternifolia* (Tea Tree) Oil, Melissa Oil (Lemon Balm), *Mentha Arvensis* (Mint) Oil, *Mentha Viridis* (Spearmint) Leaf Oil, Methyl Ricinoleate, Mink Oil, Monoi De Tahiti, Mountain Savory Oil, Mugwort Oil, Mustard Oil (Essential Oil), *Myroxylon Pereirae* (Balsam) Oil, Myrrh Oil, Myrtle Oil, Neem Oil, Neem Tree Oil, Neroli, Nutmeg Oil, Octyldodecyl Ricinoleate, Olive Oil, Orange Oil, Oregano Oil, Palm Kernel Oil, Palm Oil, Palo Santo Oil, Parsley Oil, Patchouli Oil, Pennyroyal Oil, Peppermint Oil, *Perilla* Essential Oil, Petitgrain Oil, *Pimpinella Anisum* (Anise) Oil, Pine Oil, *Piper Nigrum* (Black Pepper) Essential Oil, Plum Kernel Oil, Pomegranate Oil, Potassium Ricinoleate, *Prunus Dulcis* (Almond) Oil, Pumpkin Seed Oil, Ravensara Oil, Red Cedar Oil, Red Palm Oil, Rice Bran Oil, Ricinoleic Acid, Roman Chamomile Oil, *Rosa Mosqueta* (Rosehip) Oil, *Rosa Rubiginosa* (Rosehip) Oil, Rose Oil, Rosehip Seed Oil, Rosewood Oil, *Rosmarinus Officinalis* (Rosemary) Oil, Safflower Oil, Sage Oil, Sandalwood Oil, Sassafras Root Bark (Sassafras) Oil, *Satureja* Species (Savory) Oil, *Schisandra Chinensis* (Schisandra) Oil, Sesame Oil, Shea Nut Oil, Sodium Ricinoleate Oil, Spearmint Oil, Spice Star Anise (Star Anise) Oil, Spikenard Oil, Spruce Oil, Sunflower Oil, Sweet Almond Oil, Tamanu Oil, *Tanacetum Balsamita* (Costmary) Oil, Tangerine Oil, Thyme Oil, *Tsuga* Oil, Turmeric Oil, Valerian Oil, Vetiver Oil (Khus Oil), *Vitis Vinifera* (Grape) Seed Oil, Walnut Oil, Western Red Cedar Oil, Wheat Germ Oil, Wintergreen Oil, Yarrow Oil, Ylang-Ylang Oil, Zedoary Oil, Zinc Ricinoleate Oil, Zingiberaceae (Ginger) (Cardamom Seed) Oil, and/or the like.

Castor Oil, which is the most preferred plant or plant seed oil for use in the base compositions and active agent-containing compositions of the invention, is derived from the seeds of the Castor Oil plant, and typically consists of from about 87% to about 90% ricinoleic acid (major component), about 7% oleic acid, about 3% linoleic acid, about 2% palmitic acid and about 1% stearic acid. Most chemical and physical properties of Castor Oil are based on the molecular structure of ricinoleic acid.

Ricinoleic Acid

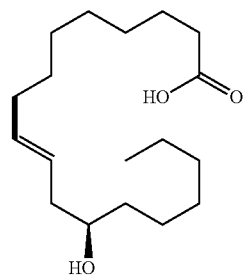

Castor oil, and other plant and plant seed (and other) oils, are commercially available from sources that are known by those having ordinary skill in the art, for example, from Rita Corporation (Crystal Lake, Ill.), Bulkoil.com (Greenbrae, Calif.) and Inner Mongolia Tianrun Castor Development Co., Ltd. (Inner Mongolia, China).

The amount (combined) of one or more plant or plant seed oils that is optionally present in the active agent-containing compositions of the invention, such as Castor oil, is an amount that is effective to cause the compositions to have one or more of the beneficial characteristics that are described herein, such as causing, or aiding in causing (possibly along with one or more other ingredients), such compositions to function as an emollient upon the skin (i.e., to render the skin more soft than it would have been prior to applying the compositions thereto).

Original Active Agent-Containing Compositions

When present in the original active agent-containing compositions, the amount (combined) of one or more plant or plant seed oils that is present therein preferably ranges from about 0.1 to about 24 weight percent, and more preferably ranges from about 8 to about 17 weight percent, and still more preferably ranges from about 10 to about 15 weight percent, and even more preferably ranges from about 11 to about 12 weight percent.

Improved Active Agent-Containing Compositions

When present in the improved active agent-containing compositions, the plant oil(s) and/or plant seed oil(s), such as castor oil, preferably is present in the compositions in an amount (combined) preferably ranging from about 0.1 to about 37.50 (from about 0.1 to about 37.0 if one or more flavoring ingredients are present) weight percent, and more preferably ranging from about 12.50 to about 37.50 (from about 12.0 to about 37.0 if one or more flavoring ingredients are present) weight percent, and still more preferably ranging from about 24.0 to about 26.0 (from about 23.50 to about 25.50 if one or more flavoring ingredients are present), and is most preferably about 25.0 (about 24.5 if one or more flavoring ingredients are present) weight percent.

Additional information about plant and plant seed oils generally, and about Caster Oil specifically, including extraction and refining methods therefore, is present in, for example, Carol Schiller et al., "*The Aromatherapy Encyclopedia: A Concise Guide to over 385 Plant Oils*" (Basic Health Publications, 1st Edition, ISBN-10: 1591202280, 2008); Frederic P. Miller, "*Castor Oil*" (Alphascript Publishing, ISBN-10: 6130261918, 2009); D. S. Oqunniyi, "Castor Oil: A Vital Industrial Raw Material (Bioresource Technology)" (Elsevier, 2006); Johann Vollmann, "*Oil Crops: Handbook of Plant Breeding*" (Springer, 1st Edition, ISBN-10: 0387775935, 2009); Hermann Janson, "*Castor Oil Production and Processing*" (United Nations, ASIN: B0006DZ23G, 1974); and/or Ernest Guenther, "*The Essential Oils, Individual Essential Oils of the Plant Families*" (Krieger Pub Co., ISBN-10: 0894647733, 1992).

Fatty Alcohols

One or a plurality of fatty alcohols, such as stearyl alcohol, is optionally, but preferably, employed as a base ingredient in the compositions of the invention, and in the topical active agent-containing compositions of the invention, and functions primarily to cause, or aid in causing (generally in combination with one or more other ingredients), such compositions to properly form, or be present in a form of, a solid or semi-solid structure (preferably a solid stick), but may also function as an emollient (skin softener), thickener and/or binding agent therein. The fatty alcohol often functions as a bonding agent that binds, or helps bind, all of the ingredients in the compositions together.

Preferred fatty alcohols for use in the base and active agent-containing compositions of the invention include stearyl alcohol, cetyl alcohol, cetyl stearyl alcohol and behenyl alcohol, with stearyl alcohol being the most preferred, and is preferably present therein (without other fatty alcohols). A wide variety of other fatty alcohols are known by those having ordinary skill in the art and are described in sources that are known by those having ordinary skill in the art, such as in Stephen Mudge, "*Fatty Alcohols: Anthropogenic and Natural Occurrence in the Environment*" (Royal Society of Chemistry, 1st Edition, ISBN-10: 0854041524, 2008).

Stearyl alcohol (also known as octadecyl alcohol or 1-octadecanol), which is the most preferred fatty alcohol for use in the base compositions and active agent-containing compositions of the invention, is a substance prepared from stearic acid by the process of catalytic hydrogenation, and has the molecular formula $C_{18}H_{38}O$. It is a fatty alcohol that generally is in the form of white solid granules or flakes that are insoluble in water, and has a melting point of 60° C. and a boiling point of 210° C. (at 15 mmHg or 2.0 kPa).

Stearyl Alcohol

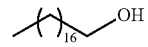

Stearyl alcohol, and other fatty alcohols, are commercially available from sources that are known by those having ordinary skill in the art, for example, from Rita Corporation (Woodstock, Ill.), Sciencelab.com, Inc. (Houston, Tex.) or Alpha Aesar (Ward Hill, Mass.).

Examples of other fatty alcohols that may be employed in the base compositions and active agent-containing compositions of the invention include, but are not limited, to Stearamine Oxide, Stearyl Acetate, Stearyl Caprylate, Stearyl Citrate, Stearyldimethyl Amine, Stearyl Glycyrrhetinate, Stearyl Heptanoate, Stearyl Octanoate, Stearyl Stearate, Plant Sources, Vegetable Stearic Acid, Cetyl Alcohol, Arachidyl Alcohol, Behenyl Alcohol, Capric Alcohol, Capryl Alcohol, Ceryl Alcohol, Cetearyl Alcohol, Cetyl Alcohol, Cluytyl Alcohol, Elaidolinolenyl Alcohol, Elaidolinoleyl Alcohol, Elaidyl Alcohol, Erucyl Alcohol, Geddyl Alcohol, Heneicosyl, Heptadecyl Alcohol, Isostearyl Alcohol, Lauryl Alcohol, Lignoceryl Alcohol, Linolenyl Alcohol, Linoleyl Alcohol, Melissyl Alcohol, Montanyl Alcohol, Myricyl Alcohol, Myristyl Alcohol, Nonadecyl Alcohol, Oleyl Alcohol, Palmitoleyl Alcohol, Pelargonic Alcohol, Pentadecyl Alcohol, Ricinoleyl Alcohol, Tridecyl Alcohol, Undecyl Alcohol and Isostearyl Alcohol.

The amount (combined) of one or more fatty alcohols that is optionally present in the active agent-containing compositions of the invention is an amount that is effective to cause the compositions to have one or more of the beneficial characteristics that are described herein, such as causing, or aiding in causing (generally in combination with one or more other ingredients), such compositions to properly form, or be present in a form of, a solid or semi-solid structure, for example, in the shape of a stick or any another shape desired or required, or present in a pot or jar.

Original Active Agent-Containing Compositions

When present in the original active agent-containing compositions, the amount (combined) of one or more fatty alcohols that is present in these compositions, such as stearyl alcohol, preferably ranges from about 0.1 to about 22 weight percent, and more preferably ranges from about 10 to about 22 weight percent, and still more preferably ranges from about 18 to about 22 weight percent.

Improved Active Agent-Containing Compositions

When present in the improved active agent-containing compositions, the fatty alcohol(s), such as stearyl alcohol, preferably is present in the compositions in an amount (combined) preferably ranging from about 0.1 to about 25 weight percent, and more preferably ranging from about 15 to about 25 weight percent, and still more preferably ranging from about 19 to about 21 weight percent, and is most preferably about 20 weight percent (whether or not any favoring ingredients are present in the compositions).

Additional information about fatty alcohols is present, for example, in Sylvia S. Talmage, "*Environmental and Human Safety of Major Surfactants: Alcohol Ethoxylates and Alkylphenol Ethoxylates*" (CRC Press, 1st Edition, ISBN-10: 1566700175, 1994); and Egon Matijevic, "*Surface and Colloid Science, Vol. 16*" (Springer, 1st Edition, ISBN-10: 030646456X, 2001).

Fats

One or a plurality of fats, preferably having a melting point of at least about 85° F. (29.444° C.), such as from about 34° C. to about 38° C. (from about 93° F. to about 100° F.), and which more preferably have a melting point of at least about 90° F. (32.222° C.) or higher, such as cocoa butter (also called *theobroma* oil or *theobroma cacao*), is optionally, but preferably, employed as a base ingredient in the compositions of the invention, and in the topical active agent-containing compositions of the invention. Such fat(s) function primarily to cause, or aid in causing (generally in combination with one or more other ingredients), such compositions to properly form, or be present in a form of, a solid structure (preferably a solid stick), but may also function as an emollient (skin softener), a moisturizer and/or a binding agent therein.

Examples of fats (and possibly oils in some cases) that may be employed in base and other compositions of the invention include, but are not limited, to Cocoa Butter, Shea Butter, Shea Nut Butter, Mango Butter, Costus Root, Calamas Root, Canola, Crisco, Cubeb, Ethyl Ricinoleate, Kokum Butter, Lanolin, Lard, Mowrah Butter and Tallow (Beef). A wide variety of fats are known by those having ordinary skill in the art and are described in sources that are known by those having ordinary skill in the art, such as in Richard D. Obrien, "*Fats and Oils: Formulating and Processing for Applications*" (CRC Press, 3rd Edition, ISBN-10: 1420061666, 2008), Glen D. Lawrence, "*The Fats of Life: Essential Fatty Acids in Health and Disease*" (Rutgers University Press, ISBN-10: 081354677X, 2010), and Icon Group International, "*The* 2009 *Report on Confectionery and Ice Cream Coatings made from Cacao Bean Cocoa and Fats other than Cocoa Butter: World Market Segmentation by City*" (ICON Group International, Inc., ASIN: B002AJG6AC, 2009).

Preferred fats for use in the base compositions and active agent-containing compositions of the invention include cocoa butter, shea butter and mango butter, with cocoa butter being the most preferred, and preferably present therein alone (i.e. without other fats).

Typically, cocoa butter is solid at room temperature, but readily melts at body temperature. It generally has a melting point of from about 34° C. to about 38° C. (from about 93° F. to about 100° F.). Cocoa butter displays polymorphism, generally having α, γ, β' and β crystals, with melting points of about 17, 23, 26 and 35-37° C., respectively, with the β crystal form being the most stable form.

Cocoa butter, and other fats, are commercially available from sources that are known by those having ordinary skill in the art, for example, from Rita Corporation (Crystal Lake, Ill.) and Bulkoil.com (Greenbrae, Calif.).

The amount (combined) of one or fats that is optionally present in the active agent-containing compositions of the invention, such as cocoa butter, is an amount that is effective to cause the compositions to have one or more of the beneficial characteristics that are described herein, such as causing, or aiding in causing (generally in combination with one or more other ingredients), such compositions to properly form, or be present in a form of, a solid or semi-solid structure, for example, in the shape of a stick or any another shape desired or required, or present in a pot or jar.

Original Active Agent-Containing Compositions

When present in the original active agent-containing compositions, the amount (combined) of the one or more fats that is present therein preferably ranges from about 0.1 to about 9 weight percent, and more preferably ranges from about 5 to about 9 weight percent, and still more preferably ranges from about 6 to about 8 weight percent.

Improved Active Agent-Containing Compositions

When present in the improved active agent-containing compositions, the fat(s), such as cocoa butter, preferably is present in the compositions in an amount (combined) preferably ranging from about 0.1 to about 12 weight percent, and more preferably ranging from about 2 to about 12 weight percent, and still more preferably ranging from about 6 to about 8 weight percent, and is most preferably about 7 weight percent (whether or not any favoring ingredients are present in the base compositions).

Additional information about fats is present, for example, in Robin Dand, "*The International Cocoa Trade*" (CRC Press, 2nd edition, ISBN-10: 0849322669, 1999); and Emmanuel Ohene Afoakwa, "*Chocolate Science and Technology*" (Wiley-Blackwell, ISBN-10: 1405199067, 2010).

Flavorings

One or more flavorings are, optionally, but preferably, employed as a base ingredient in the compositions of the invention, and in the topical active agent-containing compositions of the invention, and function to: (i) provide such compositions with a desirable and/or distinct aroma, fragrance and/or taste (i.e., they make the compositions smell and/or taste good and/or otherwise desirable to consumers thereof, who may apply them to their lips); and/or (ii) effectively reduce, mask or eliminate one or more bitter and/or other undesirable tastes and/or odors that are caused by, or otherwise result from, an inclusion of a different ingredient in these compositions, such as hydrocortisone, which has a very bitter taste and odor, and generally causes compositions including hydrocortisone to have a very undesirable bitter taste and odor.

The flavorings that may be employed in the active agent-containing compositions of the invention may vary widely and include, but are not limited to, vanilla, chocolate, citrus flavors (lemon, orange, grapefruit and/or the like), fruit flavors (strawberry, cherry, kiwi, pineapple, blueberry, apple, grape, pear, cantaloupe and/or the like), cinnamon, mint (spearmint, peppermint, wintergreen and/or the like), pina colada, honey, molasses, caramel, butterscotch, butter pecan, ginger, sassafras, hot pepper, soda (cola, root beer, sprite, ginger ale, cream soda, Dr. Pepper and/or the like) and/or the like. Virtually any type of a desired flavor or flavoring, or a combination thereof, may be employed.

The flavorings that may be employed in the base compositions and active agent-containing compositions of the invention may be natural flavorings, for example, a vanilla flavoring procured from vanilla beans, peppermint flavoring procured from a peppermint plant, spearmint flavoring procured from a spearmint plant, wintergreen flavoring procured from a creeping wintergreen or teaberry plant, lemon flavoring procured from a lemon or lemon peel, ginger flavoring procured from a ginger plant or root, sassafras flavoring procured from the dried root bark of a sassafras tree, or synthetic or artificial flavorings, or extracts, such as an almond extract. All of the foregoing types of flavorings may be obtained by methods that are known by those having ordinary skill in the art or are commercially available from sources that are known by those having ordinary skill in the art, for example, from Bell Flavors & Fragrances Inc. (Northbrook, Ill.), International Flavors and Fragrances (New York, N.Y.) and the Spice Barn (Lewis Center, Ohio).

The amount (combined) of one or more flavorings that is optionally present in the active agent-containing compositions of the invention is an amount that is effective to cause these compositions to: (i) have a pleasant or desirable, or a specific, taste and/or odor, such as a good and/or desirable vanilla taste and odor; (ii) have no, a reduced, or a minimal, unpleasant taste and/or odor (in comparison with how the taste and/or odor would have been if no flavoring(s) had been included in the compositions), such as a reduction of a bitter taste and/or odor that would otherwise have been present as a result of an inclusion of hydrocortisone in the compositions; or (iii) have no taste and/or no odor.

Original Active Agent-Containing Compositions

When present in the original active agent-containing compositions, the amount (combined) of one or more flavorings that is present therein preferably ranges from about 0.1 to about 3.5 weight percent, and more preferably ranges from about 0.2 to about 3 weight percent, and even more preferably ranges from about 0.3 to about 2 weight percent, and still more preferably ranges from about 0.4 to about 1 weight percent.

Improved Active Agent-Containing Compositions

When present in the improved active agent-containing compositions, the flavoring(s), such as vanilla flavorings, preferably is present therein in an amount (combined) preferably ranging from about 0.1 to about 3.5 weight percent, and more preferably ranging from about 0.1 to about 2.5 weight percent, and still more preferably ranging from about 0.3 to about 1.5 weight percent, and is most preferably about 0.5 weight percent.

Additional information about flavorings is present, for example, in Virginia Lanzotti et al., "*Flavour and Fragrance Chemistry* (*Proceedings of the Photochemical Society of Europea*) (Springer, 1st edition, ISBN-10: 079236211X, 2000); Carol Schiller et al., "*The Aromatherapy Encyclopedia: A Concise Guide to over 385 Plant Oils*" (Basic Health Publications, 1st Edition, ISBN-10: 1591202280, 2008); and Orlindo Secondini, "*Handbook of Perfumes and Flavors*" (Chemical Publishing Company, ISBN-10: 0820603341, 1990).

Other Optional Ingredients

The base compositions and active agent-containing compositions of the invention may, in some cases, optionally, contain one or more other (additional or substitute) active or inactive ingredients, such as various vitamins, minerals, antioxidants, anti-inflammatory agents, antibiotic agents, antibacterial agents, antiviral agents, whitening agents, dispersing agents, thickening agents (xanthan gum, guar gum, gum arabic, methylcellulose, sodium carboxymethyl cellulose, carrageenan, starch and the like), anti-itch agents, polymers, pigments, cell activating agents, sunscreen agents, preservatives, colorants, collagen, glycerin, lecithin, talc, aloe vera, lanolin or other agents, for example, vitamin E (ą-tocopherol, β-tocopherol, γ-tocopherol, δ-tocopherol and the like). However, the compositions need not include any ingredients other than those that are described herein.

Various optional ingredients that may possibly be employed in the base compositions and active agent-containing compositions of the invention may be described in, for example, "*Cosmetic Additives—An Industrial Guide*" (William Andrew Publishing, 1991), "*Cosmetic and Toiletry Formulations*" (Volume 3, $2^{nd}$ Edition, William Andrew Publishing, 1995), "*Handbook of Cosmetics and Personal Care*" (Gower Publishing Unlimited, ISBN 0566074702, 1994), "*Cosmetic Ingredients*" (Three Rivers Press, ISBN 0609803670, 1999) and "*Cosmetics Unmasked*" (Thorsons, Harper Collins, ISBN 0-00-710568-1, 2001), and/or may be commercially available from Base Formula, Ltd. (Melton Mowbray, England), Well Naturally Products, Ltd. (Blaine, Wash.), Essential Wholesale (Clackamas, OR), Urist Cosmetics, Inc. (Richmond, Calif.) and/or Sciencelab.com, Inc. (Houston, Tex.). Those having ordinary skill in the art may determine the weight percents of one or more optional ingredients that may be employed in the base compositions and active agent-containing compositions of the invention, and how to vary the other ingredients present therein accordingly.

Optional ingredients that may possibly be included in the base compositions and active agent-containing compositions of the present invention include, but are not limited to, the ingredients that are identified below, and suitable amounts thereof, which may readily be determined by those having ordinary skill in the art.

Glycols
Glycerin
Propylene Glycol
Butylene Glycol
Hexylene Glycol
2-Methyl Propane Diol
Other Alcohols Ethanol
Isopropanol
n-propanol
lauryl alcohol
oleyl alcohol
Esters Isopropyl Myristate
Isopropyl Palmitate
Jojoba Oil
Glyceryl tri caprate/caprylate
Butyl Acetate
Propylene Glycol di Caprate/Caprylate
Sorbitan Esters
Diesters of Diacids
Ethyl Acetate
Ethoxylated Materials Ethoxylated Fatty Alcohols
Ethoxylated Fatty Acids
Ethoxylated Sorbitan Esters
Ethoxylated Glycerides
Ethoxydiglycol -continued Ketones Acetone
Methyl Ethyl Ketone
Other Waxes/Bases Lubragels
Zigels
Jojoba Glaze
Absorption Bases
Aliphatic Compounds n-alkanes
branched alkanes
Permethyls
Propoxylated Materials
Propoxylated Fatty Alcohols
Propoxylated Fatty Acids
Esters of Propoxylated Fatty Alcohols
Ethoxylated Propoxylates
Aerosol Propellant Gases
Anhydrous Ionic Surfactants Phosphate Esters
Sulfates
Carboxylates
Fatty Amine Salts
Quaternary Nitrogen Salts
Other Fats, Oils and Waxes Derived from Animals, Minerals, Marine
or Other Sources
Silicones Dimethicone
Simethicone
Cyclomethicone
Dimethicone Ethoxylates and
Propoxylates
Fluorocarbons and Derivatives Zonyls
Fluorocarbon Alcohols
Amides Fatty Acid Diethanolamides
Fatty Acid Monoethanolamides
Fatty Acid Dimethylaminopropyl
Amides
Polymers Polyalkenes
Polyoxyethylenes
Polyoxypropylenes
Polyamides
Polyesters
Polyurethanes
Cellulostics and Derivatives
Copolymers

Most Preferred Active Agent-Containing Compositions

Two of the most preferred original active agent-containing compositions of the present invention, and two of the most preferred improved active agent-containing compositions of the present invention, contain the ingredients that are set forth below, and the weight percents thereof (of the 100% total weight of the composition), and preferably do not include any different or additional ingredients, and are produced in the form of a solid cylinder (stick), such as a traditional Chap-Stick® form, but in various sizes, for example, in the two different sizes that are illustrated in FIG. 1, and in a form that is contained in a pot, jar or can. The first original formulation includes a flavoring, and is the more preferred of the two, and the second formulation does not include any flavoring (and the weight percent of the Castor Oil is increased by the same weight percent that is missing with respect to the missing flavoring to compensate for the absent flavoring, which may also be done with other absent formulation ingredients). This is the same case with the two improved formulations. These compositions have all been determined via topical skin application testing on human beings, as is discussed in the "Examples" section, and as is illustrated in FIGS. 2-17, to be extremely efficacious for deeply penetrating, conditioning and healing, various layers of, and tissues present in, the skin of human beings, including the dermis and epidermis, in connection with various skin disorders, diseases and conditions of human beings, as are described herein, and for maintaining their forms, shapes and consistencies under adverse environmental conditions.

Original Active Agent-Containing Formulations

| Ingredient | Weight Percent |
|---|---|
| Hydrocortisone | 1.0 |
| FANCOL VB | 11.0 |
| Natunola Castor 1023 | 18.0 |
| Finsolv TN | 11.0 |
| Bees Wax | 20.0 |
| Castor Oil | 11.5 |
| Stearyl Alcohol | 20.0 |
| Cocoa Butter | 7.0 |
| Flavoring (Vanilla) | 0.5 |
| TOTAL | 100 |

| Ingredient | Weight Percent |
|---|---|
| Hydrocortisone | 1.0 |
| FANCOL VB | 11.0 |
| Natunola Castor 1023 | 18.0 |
| Finsolv TN | 11.0 |
| Bees Wax | 20.0 |
| Castor Oil | 12.0 |
| Stearyl Alcohol | 20.0 |
| Cocoa Butter | 7.0 |
| Flavoring (Vanilla) | 0.0 |
| TOTAL | 100 |

Improved Active Agent-Containing Formulations

| Ingredient | Weight Percent |
|---|---|
| Hydrocortisone | 1.0 |
| FANCOL VB | 11.00 |
| Natunola Castor 1023 | 10.00 |
| FINSOLV TN | 15.00 |
| Bees Wax | 11.00 |
| Castor Oil | 24.50 |
| Stearyl Alcohol | 20.00 |
| Cocoa Butter | 7.00 |
| Flavoring (Vanilla) | 0.50 |
| TOTAL | 100 |

| Ingredient | Weight Percent |
| --- | --- |
| Hydrocortisone | 1.0 |
| FANCOL VB | 11.00 |
| Natunola Castor 1023 | 10.00 |
| FINSOLV TN | 15.00 |
| Bees Wax | 11.00 |
| Castor Oil | 25.00 |
| Stearyl Alcohol | 20.00 |
| Cocoa Butter | 7.00 |
| Flavoring (Vanilla) | 0.0 |
| TOTAL | 100 |

Preparation of Compositions

The base compositions and active-agent containing compositions of the invention (whether or not including one or more active agents) are preferably prepared in the manner that is described below, or elsewhere herein, preferably employing the specified order of steps and process conditions identified therein (amounts, times, temperatures, mixing and the like), but may be prepared using other methods that produce compositions having the features and/or characteristics that are described herein, using customary equipment that is known by those having skill in the art for preparing topical skin products or other equipment.

Although the methods that are described below (and elsewhere herein) refer to the active agent hydrocortisone, other active agents can be used in these methods in addition to, or alternatively to, hydrocortisone (in the same or similar manner described). The hydrocortisone (and/or other active agent(s)) may be physically combined with the base composition that is described herein to achieve the concentrations that are described herein by stirring together, or otherwise mixing or combining, the individual components in the manner that is described herein (preferably with continuous mixing). Preferably, sufficient agitation to achieve relative homogeneity of the various ingredients in the compositions is employed. Agitation may be achieved, for example, using a standard (or other) mixer, at a slow, moderate or even vigorous speed. Using the information that is provided herein, those having ordinary skill in the art will be able to vary these methods and compositions in a manner desired or required under a particular set of circumstances or to produce a particular base composition or active agent-containing composition of the invention.

To prepare the original base and active-agent formulations of the invention, an amount (combined) of one or more plant oils or plant seed oils, such as castor oil, that is sufficient for producing an effective base or active agent-containing composition of the invention in a form that may properly be filled into a suitable container or packaging, and topically applied to the skin of a mammal, with the amount thereof possibly varying widely depending upon the size of the batch of the composition being produced, which may be determined by those having ordinary skill in the art and, as one example may be about 11.5 g, is optionally added to a standard stainless steel drum including a mixer and heated using a conventional hot plate to a temperature that is effective for evenly heating the plant oil(s) and/or plant seed oil(s) in the drum, which generally ranges from about 75° C. to about 85° C., while stifling it continuously using the mixer.

An amount of FANCOL VB that is sufficient for producing an effective composition of the invention in a form that may be properly filled into a suitable container or packaging, and topically applied to the skin of a mammal, with the amount of FANCOL VB possibly varying widely depending upon the size of the batch of the composition being produced, which may be determined by those having ordinary skill in the art and, as one example may be about 11.0 g, is then added to the plant oil(s) and/or plant seed oil(s) in the drum (if present), and mixed with therewith until it is preferably completely dissolved therein, which generally takes from about 30 to about 45 minutes, while maintaining a temperature that is effective for preferably evenly heating the mixture and completely dissolving the FANCOL VB in the oil(s), which generally ranges from about 75° C. to about 85° C. If no plant oil(s) or plant seed oil(s) are employed in the first step, the FANCOL VB is added to the steel drum and heated using a conventional hot plate to the foregoing temperature, which is effective for evenly heating the FANCOL VB in the drum An amount of Natunola Castor 1023 that is sufficient for producing an effective composition of the invention in a form that may be properly filled into a suitable container or packaging, and topically applied to the skin of a mammal, with the amount of Natunola Castor 1023 possibly varying widely depending upon the size of the batch of the composition being produced, which may be determined by those having ordinary skill in the art and, as one example may be about 18.0 g, is then added to the above product, such as a mixture of plant oil(s) and/or plant seed oil(s) and FANCOL VB, in the drum while a temperature that is effective for preferably evenly heating the mixture and dissolving the Natunola Castor 1023 therein is maintained, which generally ranges from about 75° C. to about 85° C. Mixing is then preferably continued for a period of time that is sufficient to completely dissolve the Natunola Castor 1023 therein, which typically ranges from about 30 to about 60 minutes.

An amount of bees wax that is sufficient for producing an effective composition of the invention in a form that may be properly filled into a suitable container or packaging, and topically applied to the skin of a mammal, with the amount of bees wax possibly varying widely depending upon the size of the batch of the composition being produced, which may be determined by those having ordinary skill in the art and, as one example may be about 20.0 g, is added to the above mixture in the drum while a temperature that is effective for preferably evenly heating the mixture and dissolving the bees wax therein is maintained, that temperature generally ranging from about 75° C. to about 85° C. Mixing is preferably continued for a period of time that is sufficient to completely dissolve the bees wax therein, which typically ranges from about 30 to about 45 minutes.

An amount (combined) of one or more fatty alcohols, such as stearyl alcohol, that is sufficient for producing an effective composition of the invention in a form that may be properly filled into a suitable container or packaging, and topically applied to the skin of a mammal, with the amount of the fatty alcohol(s) possibly varying widely depending upon the size of the batch of the composition being produced, which may be determined by those having ordinary skill in the art and, as one example may be about 20.0 g, is then optionally added to the above mixture in the drum while a temperature that is effective for preferably evenly heating the mixture and dissolving the fatty alcohol(s) therein is maintained, that temperature generally ranging from about 75° C. to about 85° C. If fatty alcohol(s) are added, mixing is preferably continued for a period of time that is sufficient to completely dissolve the fatty alcohol(s) therein, which typically ranges from about 30 to about 45 minutes.

An amount (combined) of one or more fats, such as cocoa butter, that is sufficient for producing an effective composition of the invention in a form that may be properly filled into a suitable container or packaging, and topically applied to the skin of a mammal, with the amount of the fat(s) possibly varying widely depending upon the size of the batch of the composition being produced, which may be determined by those having ordinary skill in the art and, as one example may be about 7.0 g, is optionally added to the above mixture in the drum while a temperature that is effective for preferably evenly heating the mixture and dissolving the fat(s) therein is maintained, that temperature generally ranging from about 75° C. to about 85° C. If fat(s) are added, mixing is preferably continued for a period of time that is sufficient to completely dissolve the fat(s) therein, which typically ranges from about 30 to about 45 minutes.

An amount of Finsolv TN that is sufficient for producing an effective composition of the invention in a form that may be properly filled into a suitable container or packaging, and topically applied to the skin of a mammal, with the amount of Finsolv TN possibly varying widely depending upon the size of the batch of the composition being produced, which may be determined by those having ordinary skill in the art and, as one example may be about 11.0 g, is added to the above mixture in the drum while a temperature that is effective for preferably evenly heating the mixture and dissolving the Finsolv TN therein is maintained, that temperature generally ranging from about 75° C. to about 85° C. Mixing is preferably continued for a period of time that is sufficient to completely dissolve the Finsolv TN therein, which typically ranges from about 30 to about 45 minutes.

The above mixture is preferably mixed for an additional period of time that is sufficient to have any remaining particles present therein preferably be completely dissolved in the mixture, which generally ranges from about 30 to about 60 minutes, while a temperature that is sufficient to dissolve such particles in the mixture is preferably maintained, which generally ranges from about 75° C. to about 85° C.

If the composition being produced is an active-agent containing composition, the resulting mixture is then preferably permitted to cool (naturally or using conventional cooling equipment, such as a refrigerator) to a temperature that is effective for mixing hydrocortisone (and/or other active ingredient(s)) therewith in a manner that does not render the hydrocortisone (and/or other active ingredient(s)) ineffective or significantly less effective than it was in its original form (i.e., prior to adding it to the above mixture), which typically ranges from about 55° C. to about 60° C.

An amount of hydrocortisone (and/or other active ingredient(s)) that is sufficient for producing an effective active agent-containing composition of the invention in a form that may be properly filled into a suitable container or packaging, and topically applied to the skin of a mammal, with the combined amount of the hydrocortisone and/or other active ingredient(s) possibly varying widely depending upon the size of the batch of the composition being produced, which may be determined by those having ordinary skill in the art and may be, as one example about 1.0 g, is then added to the above mixture and mixed therewith preferably until it is dissolved while maintaining the temperature of the mixture at the above temperature (i.e., preferably ranging from about 55° C. to about 60° C.), which typically takes from about 30 to about 45 minutes.

The resulting mixture (not including any active ingredient(s) for a base composition or including one or more active ingredient(s) for an active agent-containing composition) is then permitted to cool (naturally or using conventional cooling equipment, such as a refrigerator) to a temperature that is effective for optionally incorporating one or more flavorings therein in a manner that preferably does not render the flavoring less flavorful or less aromatic, or substantially less flavorful or less aromatic, than it was originally (i.e., prior to incorporating it therein), which generally ranges from about 50° C. to about 55° C., and then the flavoring(s) is added to the mixture. The flavoring(s), if added, is preferably mixed with the mixture for a period of time that is sufficient to incorporate it evenly throughout the mixture, which generally ranges from about 15 to about 20 minutes, while preferably maintaining a temperature that is effective for permitting such even distribution of the flavoring in the mixture, that temperature generally ranging from about 50° C. to about 55° C.

At this point in the above process, the resulting mixture will preferably be liquid in nature, and may have a light yellow color and a general appearance of a thin, milky liquid. For active agent-containing compositions, a sample of the resulting mixture is then preferably analyzed using standard techniques known by those having ordinary skill in the art, such as High Performance Liquid Chromatography (HPLC) or Gas Chromatography (GS), to determine the concentration of the active agent(s) that is present in the mixture, as one example, 1 weight percent of hydrocortisone.

For the active agent-containing compositions, once the sample is found to be acceptable (i.e., to possess the above characteristics and the desired concentration of the active agent(s) therein), the entire batch of the composition is preferably transferred to a filler assembly line, where it is poured or otherwise transferred (manually, robotically or otherwise) into individual (or other) containers or molds of any desired size, shape and/or other characteristics, to preferably form a solid, preferably in a cylindrical shape, such as those that are illustrated in FIG. 1, or a traditional ChapStick® type (or other) stick. Standard filling equipment that is known by those having ordinary skill in the art may be used for this step.

A wide variety of plastic, glass, metal and other types and materials of containers, cases, pouches, bottles, jars, squeezable (or other) tubes (lip balm, roll-on, roll-up and/or the like), vials, boxes, bags, pots, tins, cans, lids, other closures, and/or the like, having a wide variety of different sizes, shapes, colors and/or other physical attributes, and made from a wide variety of different materials, or combinations thereof, which may be used to removably or irremovably contain or house the compositions are available from sources that are known by those having ordinary skill in the art, such as from SKS Bottle and Packaging, Inc. (Watervliet, N.Y.). For example, the compositions may be present in individual containers that form around, house or contain a solid in a shape of a stick, as is shown in FIG. 1, which may be partially or fully removed from the container for use by a user by exerting a twisting or turning action of the end of the container that does not include the closure (lid, cap or the like). Alternatively, they may be present in lip gloss sized and types of pots or jars, and do not become removed from the containers by a user when being used, and/or the like.

After the compositions settle, and possibly harden into solid forms, in the containers, which generally takes a period of time ranging from about 60 to about 120 minutes, a container cap is preferably applied to the open end of each container, preferably along with a label including identifying and/or other information, such as a lot code.

The resulting product is then preferably individually packaged using conventional packaging equipment known by those having ordinary skill in the art, or otherwise, into required or desired packaging of any type, which may or may not be tamper-evident and/or childproof, such as a paper or cardboard box, an aluminum or plastic pouch or sheath, and/ or the like. Alternatively, or in addition, tamper-evident and/ or childproof plastic and/or other material may be placed, formed, wrapped and/or sealed around the cap (or other)

area(s) of the container in a manner that indicates (to a consumer) tampering of the container when torn, perforated or otherwise damaged or disrupted.

The improved base and active-agent formulations of the invention may be prepared in a similar manner using the same or similar steps and conditions. However, it is preferred that such formulations be prepared by adding the various ingredients in the following order, rather than in the order described above, with mixing until the various ingredients are fully dissolved within the prior-listed ingredients:

(1) Castor Oil (Plant Oil);
(2) FANCOL VB;
(3) Bees wax;
(4) Stearyl Alcohol (Fatty Alcohol);
(5) Cocoa Butter (Fat);
(6) Finsolv TN;
(7) Natunola 1023;
(8) Hydrocortisone (Active Ingredient); and
(9) Flavor Ingredient(s).

Application and Application Rates

The base compositions and active-agent containing compositions of the invention, such as those including hydrocortisone and/or other active ingredients, and the related methods, can be employed by physicians, such as dermatologists, nurse practitioners, nurses, other skin care professionals, veterinarians, and/or the like, as well as by lay (or other) individuals, to repair, improve, partially heal (i.e., having a healing of the skin that is greater than about 0% but less than about 100% in comparison with the condition of the skin just prior to a first application of a composition of the invention to the skin) or fully heal (i.e., having a healing of about 100%) a wide variety of different skin disorders, diseases and adverse conditions, as are described herein (or otherwise), of the skin of a mammal and/or to produce or increase some other benefit to the skin.

An improvement in (greater than 0%, but less than 100%, repair or healing), or a full (100%) healing of, the skin of a mammal that has been treated with a composition of the invention may be detected in a variety of different manners, such as by a visually observable or otherwise detectable (by palpitation, touch, feel, smell and/or the like) improvement in the morphology, tone, texture and/or appearance of the skin of the mammal, including, but not limited to, a reduction or elimination in the quantity and/or severity of pain, discomfort, soreness, burning, itching, inflammation, redness (or other discoloration), bruising, bumps, blisters, cracking, cuts, perforations, punctures, other wounds, dryness or other defects, deformations and/or conditions, and/or the like. In addition, or alternatively, to being detected visually or manually, such an improvement may also be detected by questioning a patient for, example, to determine whether or not less pain and/or discomfort is present or experienced by the patent, or by using a wide variety of different dermatologic and/or other medical devices, tests and/or equipment, which are known by those having ordinary skill in the art, such as photographic analysis, grading scales related to psoriatic and eczematous disease such as, but not limited to, the PASI (Psoriasis Area and Severity Index) and EASI (Eczema Severity and Severity Index) scores, and visual observation. As is illustrated in the accompanying drawings, photographic, visual observation or other comparisons may readily be made between a mammal's skin, as it existed prior to initiating a first treatment thereof with a composition of the invention, and as it existed at the termination of such treatment, or at any point or time in between the two.

The compositions of the invention that include one or more active components may be applied to different areas of the skin of a mammal directly or indirectly in any convenient or desired manner, such as by rolling it directly upon the skin using a plastic or metal (or other) roll-up applicator, as is shown in FIG. 1, or roll-on applicator, like those used to apply deodorant to the skin, indirectly by using one or more fingers to brush or sweep across the surface of the compositions, such as when they are present in a roll-up applicator, a roll-on applicator, a lip gloss type of a pot or jar, a spray, foam or other can, or the like, and then using the fingers to apply the compositions to the skin using rubbing, sweeping, patting or other actions. These compositions may be applied to any sized area of the skin including, but not limited to, an area the size of a pinpoint (or smaller) to an area that spans one or a plurality of square centimeters, inches or even feet (or larger). As a general rule, the larger the area to be treated, the larger a roll-up or roll-on or other applicator should be (for ease and speed of application).

The active agent-containing compositions may be distributed to, or otherwise applied to, the skin, using a variety of different types of applicators and may, optionally, be externally or internally heated by a heating device, such as an electrical current from a battery or similar device, to elevate the temperature of the compositions prior to an application to the skin, for example, from ambient temperature to a temperature ranging from about 5° C. (9° F.) to about 10° C. (18° F.) above ambient temperature (or higher) upon application or desire to apply. If the temperature of the composition is elevated to one that is at, or greater than, the melting point of the composition, a portion or all of the composition may become transformed by melting from a "solid" form to a "semi-solid" form or "liquid." Such an elevated temperature may cause a "solid" composition to partially or fully melt and become transformed into a "semi-solid" or even a liquid, and applied to the skin of a mammal in such transformed form. An elevated temperature that is below the melting point of the composition may cause the composition to become softened or more pliable. A separated chamber of a container housing the composition may or may not contain the composition to be softened or melted prior to application to the body and/or lips. The ability to push the composition to this potential separate chamber may be controlled, for example, by a small aperture in the composition which could be small enough to push composition through upon revolution of the composition chamber below and pressure upward. This chamber could then be heated selectively, allowing the composition below it to remain in its non-melted form. The ability to heat it would be controllable by, for example, a button-device on the side of the chamber. It is also possible to alter the amounts of the compositions that are delivered to the skin at one time by sealing off a device delivery system from the actual composition below, thereby reducing the potential contamination of the product below the area touching the skin or lips.

The compositions of the invention that include hydrocortisone and/or one or a plurality of other active agents are preferably applied directly or indirectly to the skin of a mammal in an amount, and for a number of applications, that are effective for causing or providing: (i) a repair of, or an improvement in, the mammal's skin in some manner and/or partially or fully healing one or more disorders, diseases, adverse (or other) conditions, maladies and/or the like of the mammal's skin, for example, a decrease in inflammation, swelling, irritation, burning, itching, redness, pain, soreness, extreme (or other) dryness, bumps, blisters, itching, cracking, acne excoriae, insect bite size, wound size and/or the like, as are described herein or otherwise; and/or (ii) a reduction in pain, soreness, discomfort, itchiness and/or the like, and/or an increase in a soothing, softening, conditioning and/or the like, of the mammal's skin.

The total amount of the hydrocortisone (and/or other active agent) formulation of the invention that is effective for improving the skin in some manner and/or for partially or fully healing one or more skin conditions, disorders, diseases, maladies and/or the like, as are described herein (or otherwise), may vary widely, depending upon a variety of factors, such as the type, age, sex, genetic predisposition and general health of the mammal being treated, whether the mammal is a human or non-human mammal, the amount of the mammal's exposure to adverse or harsh environmental conditions, such as the sun, wind, heat and/or cold, the particular active agent, or combination of active agents employed, the particular formulation employed, the particular condition(s), disorder(s), disease(s), malady(s) and/or the like being treated, and/or the like, and may readily be determined by those having ordinary skill in the art using the information that is provided herein.

The amount of an active agent-containing composition of the invention that will generally be effective for achieving or obtaining one or more of the goals that are described herein may readily be determined by those having ordinary skill in the art. The quantity of such a composition to be administered to a mammal for each application, and the number of applications to be applied, depend upon the nature of the composition, the condition(s) being treated and the area(s) of the body involved, and may be determined by those having ordinary skill in the art using the information contained herein. With that being said, the amount of a composition that is applied to the skin of a mammal per each application preferably ranges from about 1 to about 20 g or ml, and more preferably ranges from about 2 to about 12 g or ml, and still more preferably ranges from about 3 to about 8 g or ml, and even still more preferably ranges from about 4 to about 6 g or ml, with about 5 g or ml being most preferred. For example, about 5 g of the composition may be applied to the skin of a mammal from a suitable container or applicator and spread over, or rubbed into, the skin using the hands or fingers or a suitable application or other device. However, such amounts can vary widely, with the lowest quantity generally being an amount that renders some improvement in the skin (either alone or in a series of multiple applications), with there not being an upper limit to the largest quantity (other than safety concerns). Although there generally is no upper limit to the quantity of composition that can be applied per application, above a certain quantity, no further improvement in the mammal's skin may be observed or otherwise detected.

The following types and sizes of applicators for compositions within the invention were used in the experiments that are described in Examples 6-9 hereinbelow.
  (i) a 0.15 fluid ounce stick-shaped roll-up skin balm measuring about 6.0 cm in length and about 1.5 cm in diameter (a suitable size for a lip and face balm—a small stick);
  (ii) a 0.50 fluid ounce stick-shaped roll-up skin balm measuring about 7.6 cm in length and about 2.0 cm in diameter (a suitable size for a body balm—a large stick); and
  (iii) a 0.25 fluid ounce jar-shaped skin balm measuring about 3.0 cm in length and about 3.3 cm in diameter (a suitable size for a face balm—a pot or jar).

In these or other experiments, about 0.1 g or ml of composition was delivered to a patient per application using the small stick, about 0.5 g or ml of composition was delivered to a patient per application using the large stick, and about 0.15 g or ml of composition was delivered to a patient per application using the pot or jar. However, such quantities to be delivered per application can be decreased or increased, as is desired or required by a user, by rolling (or otherwise applying) the stick(s) (or other application device) over smaller or larger areas of the skin per application and/or by decreasing or increasing the number of times that the stick(s) (or other application device) is rolled (or otherwise applied) over the same or different areas of the skin per application.

Thus, as only by way of some examples, the following quantities of compositions within the present invention, or others, may be administered to a user per application (in g or ml), as well as any quantities in between:
  0.01. 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9. 7.0, 7.1, 7.2, 7.3, 7.4, 7.5, 7.6, 7.7, 7.8, 7.9, 8.0. 8.1, 8.2, 8.3, 8.4, 8.5, 8.6, 8.7, 8.8, 8.9, 9.0. 9.1, 9.2, 9.3, 9.4, 9.5, 9.6, 9.7, 9.8, 9.9, 10.0, 10.1, 10.2, 10.3, 10.4, 10.5, 10.6, 10.7, 10.8, 10.9, 11.0, 11.1, 11.2, 11.3, 11.4, 11.5, 11.6, 11.7, 11.8, 11.9, 12.0, 12.1, 12.2, 12.3, 12.4, 12.5, 12.6, 12.7, 12.8, 12.9, 13.0, 13.1, 13.2, 13.3, 13.4, 13.5, 13.6, 13.7, 13.8, 13.9, 14.0, 14.1, 14.2, 14.3, 14.4, 14.5, 14.6, 14.7, 14.8, 14.9, 15.0, 15.1, 15.2, 15.3, 15.4, 15.5, 15.6, 15.7, 15.8, 15.9, 16.0, 16.1, 16.2, 16.3, 16.4, 16.5, 16.6, 16.7, 16.8, 16.9, 17.0, 17.1, 17.2, 17.3, 17.4, 17.5, 17.6, 17.7, 17.8, 17.9, 18.0, 18.1, 18.2, 18.3, 18.3, 18.4, 18.5, 18.6, 18.7, 18.8, 18.9, 19.0, 19.1, 19.2, 19.3, 19.4, 19.5, 19.6, 19.7, 19.8, 19.9, 20.0, 20.1, 20.2, 20.3, 20.4, 20.5, 20.6, 20.7, 20.8, 20.9, 21, 22, 23, 24, 25, 26, 27, 28, 29, 30, 31, 32, 33, 34, 35, 36, 37, 38, 39, 40 and so forth.

The number of applications of a composition to the skin of a mammal that will generally be effective for producing one or more desired effects, as are described herein, and the period of time during which such applications are made, may vary widely, depending upon a variety of factors, such as the concentration of the one or more active agents that are present in the composition, the amount of the composition that is applied to the mammal's skin, the condition of the mammal's skin, the amount of the mammal's sun exposure and the type, age, sex, genetic predisposition and general health of the mammal, and may readily be determined by those having ordinary skill in the art using the information provided herein. While the skin of a mammal may exhibit some improvement after only one application of a composition thereto, in order to obtain a more pronounced or full effect or benefit, it is typically beneficial to provide two or more applications to the mammal's skin, and more typically beneficial to provide at least about three applications of the composition to the skin of the mammal (three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty and so forth applications) continuously over a period of at least about one day or week, or a series of days or weeks (one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty and so forth days or one, two, three, four, five, six, seven, eight, nine, ten, eleven, twelve, and so forth weeks). The compositions may, for example, be applied as a solid stick (or other solid form), a cream, a gel, a lotion, an ointment or other convenient form as frequently as once per 15 minutes (or per fewer minutes, such as 1, 5 or 10 minutes) and as infrequently as once per day or so or on an "as needed" basis (i.e., applied as believed to be necessary or desirable, or required, typically depending upon the types and severity of symptoms).

Usually, the greater the number of applications of the composition to the skin of a mammal within a given period of time, such as a period of one week, the greater an improvement will be observed or otherwise detected in the mammal's skin, and the less time will be required for achieving such results. Although there generally is no upper limit to the number of applications of the composition that can be applied to the skin of a mammal, above a certain number of applications, no further improvement in the mammal's skin may be observed or otherwise detected. It will typically not be recommended to apply the compositions to the skin of a mammal more than about 48 times within a one-day (24 hour) period.

The table below shows examples of some of the application protocols that can be employed with the hydrocortisone and other active agent-containing compositions of the invention at concentrations that are described herein.

Examples of Application Protocols

| Number of Applications | Number of Days |
|---|---|
| 1 time each day | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 215, 220, 250, 230 and so forth (more days) |
| 2 times each day | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 215, 220, 250, 230 and so forth (more days) |
| 3 times each day | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 215, 220, 250, 230 and so forth (more days) |
| 4 times each day | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 215, 220, 250, 230 and so forth (more days) |
| 5 times each day | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, |

-continued

| Number of Applications | Number of Days |
|---|---|
| | 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 215, 220, 250, 230 and so forth (more days) |
| 6 times each day | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 215, 220, 250, 230 and so forth (more days) |
| 7 times each day | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 215, 220, 250, 230 and so forth (more days) |
| 8 times each day | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 215, 220, 250, 230 and so forth (more days) |
| 9 times each day | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 215, 220, 250, 230 and so forth (more days) |
| 10 times each day | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 215, 220, 250, 230 and so forth (more days) |
| 11 times each day | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, |

-continued

| Number of Applications | Number of Days |
|---|---|
| | 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 215, 220, 250, 230 and so forth (more days) |
| 12 times each day | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 215, 220, 250, 230 and so forth (more days) |
| 13 times each day | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 215, 220, 250, 230 and so forth (more days) |
| 14 times each day | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 215, 220, 250, 230 and so forth (more days) |
| 15 times each day | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 215, 220, 250, 230 and so forth (more days) |
| 16 times each day | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 215, 220, 250, 230 and so forth (more days) |
| 17 times each day | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, |

-continued

| Number of Applications | Number of Days |
|---|---|
| | 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 215, 220, 250, 230 and so forth (more days) |
| 18 times each day | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 215, 220, 250, 230 and so forth (more days) |
| 19 times each day | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 215, 220, 250, 230 and so forth (more days) |
| 20 times each day | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 215, 220, 250, 230 and so forth (more days) |
| 21 times each day | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 215, 220, 250, 230 and so forth (more days) |
| 22 times each day | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 215, 220, 250, 230 and so forth (more days) |
| 23 times each day | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, |

| Number of Applications | Number of Days |
| --- | --- |
| | 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 215, 220, 250, 230 and so forth (more days) |
| 24 times each day | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 215, 220, 250, 230 and so forth (more days) |
| 25 times each day | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 215, 220, 250, 230 and so forth (more days) |

It is preferable, but not necessary, that the various applications of the composition of the invention that are applied each day be equally spaced with a 24-hour period. For example, it is preferable that two applications that are to be applied in one day are applied approximately 12 hours apart. It is preferable that three applications that are to be applied in one day are applied approximately 8 hours apart. It is preferable that four applications that are to be applied in one day are applied approximately 6 hours apart. It is preferable that five applications that are to be applied in one day are applied approximately 4.8 hours apart, and so forth. It is also preferable that days not be missed when a series of applications are to be made over a specified number of days.

An improvement in an adverse (or other) skin condition, disease, disorder and/or the like of a mammal, and/or an improvement in one or more characteristics of the mammal's skin generally, will very often be observed or otherwise detected (via touch, a test and/or the like) as soon as one day after a first topical application of a composition of the invention thereto and no later than one week after such first application. However, such times may vary depending upon a variety of factors, such as the type and severity of skin problem being treated, the age, sex and general health of the patient being treated, the amount of the active ingredient(s) present therein, and like factors, which may be determined by those having ordinary skill in the art.

As an example, after a composition containing about 1 weight percent of hydrocortisone (and/or one or more other active agents) is applied one time per day to the skin of a mammal that requires, or could benefit from, skin treatment, an improvement in the condition of the skin will often be observed or otherwise detected after a period of from about one to about seven days. If the same composition is applied two times per day to the mammal's skin, an improvement in the condition of the skin of the mammal will often be observed or otherwise detected after a period of from about one to about four days. If the same composition is applied three times per day to the mammal's skin, an improvement in the condition of the mammal's skin will often be observed or otherwise detected after a period of from about one to about three days. If the same composition is applied four times per day to the mammal's skin, an improvement in the condition of the mammal's skin will often be observed or otherwise detected after a period of from about one to about two days. If the same composition is applied five times per day to the mammal's skin, an improvement in the condition of the mammal's skin will often be observed or otherwise detected after a period of from about one to about two days. More rapid results may likely be achieved when compositions containing higher weight percents of the hydrocortisone (and/or other active agent), such as 2, 3, 4 or 5 weight percent of the hydrocortisone (and/or other active agent), are applied to the skin of a mammal using the foregoing application rates. Typically, the higher the concentration of the hydrocortisone (or other active agent) that is present in the compositions, the more rapid the beneficial results thereof will be observed or otherwise detected.

Sources of Ingredients

All of the ingredients, materials and equipment employed in the methods of the invention are commercially available from sources known by those having ordinary skill in the art, such as those that are described hereinabove, and Botagenics, Inc. (Northridge, Calif.), Base Formula, Ltd. (Melton Mowbray, England), Well Naturally Products, Ltd. (Blaine, Wash.), Essential Wholesale (Clackamas, Oreg.), Urist Cosmetics, Inc. (Richmond, Calif.), Sciencelab.com, Inc. (Houston, Tex.), Fluka Chemical and Biochemical Co. (Ronkonkoma, N.Y.), Sony North America (New York, N.Y.), NOVA Technology Corporation (Portsmouth, N.H.), ServoMed (Sweden), (Expo Engineered Inc., Cicero, Ill.) and LovelySkin (Omaha, Nebr.).

The following examples describe and illustrate the base compositions and active agent-containing compositions, and methods, of the present invention. These examples are intended to be merely illustrative of the present invention, and not limiting thereof in either scope or spirit. Those having ordinary skill in the art will readily understand that variations of certain of the ingredients, amounts, conditions and/or steps employed in the procedures described in the examples can be employed.

All of the experimental testing of compositions within the present invention that is described in these examples was performed by, or under the complete direction and control of, inventor and board certified dermatologist and cosmetic surgeon Joel Schlessinger, MD, FAAD, FAACS with patients having various skin maladies under confidential conditions and circumstances in order to determine the efficacy of these compositions generally, and under different conditions, using different application rates and/or different application devices, to treat different medical skin disorders (cuts, cracks, peeling, eczema, rashes, irritation, dryness, excessive dryness and inflammation), and as applied to different body parts (lips, cheeks, chin, face, fingers, hands and/or arms) of different human beings (those of different ages and sexes, and having different weights), and in comparison with different control or known compositions.

EXAMPLE 1

Preparation of a Hydrocortisone Composition
(Including Vanilla Flavoring)

Initial Formulation

A batch of a vanilla-flavored hydrocortisone-containing topical skin formulation of the present invention in the form of a roll-up balm was prepared in the manner described below, and designated as batch LTC#6-47 AHV. The composition contained the components, and weight percents thereof, that are set forth below.

| Ingredient | Weight Percent |
| --- | --- |
| Hydrocortisone | 1.0 |
| FANCOL VB | 11.0 |
| Natunola Castor 1023 | 18.0 |
| Finsolv TN | 11.0 |
| Bees Wax | 20.0 |
| Castor Oil | 11.5 |
| Stearyl Alcohol | 20.0 |
| Cocoa Butter | 7.0 |
| Flavoring (Vanilla) | 0.5 |
| TOTAL | 100 |

11.5 g of castor oil was added to a standard stainless steel drum including a mixer and heated using a standard hot plate to a temperature ranging from about 75° C. to about 85° C., while stirring it continuously using the mixer.

11.0 g of FANCOL VB was added to the castor oil in the drum, and mixed with the castor oil until it was completely dissolved therein, which took about 30 minutes, while maintaining a temperature ranging from about 75° C. to about 85° C.

18.0 g of Natunola Castor 1023 was added to the mixture of castor oil and FANCOL VB in the drum while a temperature ranging from about 75° C. to about 85° C. was maintained. Mixing of the ingredients was then continued for about 60 minutes.

20.0 g of bees wax was then added to the above mixture in the drum while a temperature ranging from about 75° C. to about 85° C. was maintained. Mixing was continued for about 30 minutes, which was sufficient to completely dissolve the bees wax therein.

20.0 g of stearyl alcohol was then added to the above mixture in the drum while a temperature ranging from about 75° C. to about 85° C. was maintained. Mixing was continued for a period of about 30 minutes, which was sufficient to completely dissolve the stearyl alcohol therein.

7.0 g of cocoa butter was then added to the above mixture in the drum while a temperature ranging from about 75° C. to about 85° C. was maintained. Mixing was continued for about 30 minutes, which was sufficient to completely dissolve the cocoa butter therein.

11.0 g of Finsolv TN was then added to the above mixture in the drum while a temperature ranging from about 75° C. to about 85° C. was maintained. Mixing was continued for a period of about 30 minutes, which was sufficient to completely dissolve the Finsolv TN therein.

The above mixture was mixed for an additional period of about 30-60 minutes, which was sufficient to cause any remaining particles present therein be completely dissolved in the mixture, while a temperature ranging from about 75° C. to about 85° C. was maintained.

The resulting mixture was then permitted to cool naturally to a temperature ranging from about 55° C. to about 60° C.

1.0 g of hydrocortisone was then added to the above mixture and mixed therewith until it dissolved therein, which took about 30 minutes, while maintaining the temperature of the mixture ranging from about 55° C. to about 60° C.

The resulting mixture was then permitted to cool naturally to a temperature ranging from about 50° C. to about 55° C., and then 0.5 g of vanilla flavoring was added to the mixture. The vanilla flavoring was mixed with the mixture for about 15-20 minutes, which was sufficient to incorporate it evenly throughout the mixture, while maintaining a temperature ranging from about 50° C. to about 55° C.

The resulting mixture was liquid in nature, light yellow in color, and had a general appearance of a thin milky liquid. A sample of this mixture was analyzed using High Performance Liquid Chromatography (HPLC) to determine the weight percentage of hydrocortisone in the mixture, which was determined to be 1 weight percent. (Gas chromatography (GS) may also be used to perform this function.)

Once the sample was found to be acceptable (i.e., to possess the above characteristics), the entire batch of the composition was transferred to a filler assembly line, where it was manually poured into individual plastic container molds to form stick-shaped roll-up skin balms measuring about 5.5 cm in length and about 1.5 cm in diameter.

After the compositions settled and hardened in the containers, which generally took about 60 minutes, a plastic container cap was placed onto the open end of each container. (While not done with respect to the skin balms described in this example, a label including a batch code (or other information) may be placed onto one or a plurality of the container tubes.)

Several other forms of a topical hydrocortisone-containing composition, but not including the particular ingredients that are described herein, or the particular percent weights thereof, were also produced in the same, or a similar, manner as is described above. Many of these forms were not deemed to be acceptable because they were too thick (and did not spread well on the skin), too bitter tasting, ineffective in improving, repairing and/or healing one or more skin conditions or maladies and/or exhibited one or more other unacceptable characteristics. For example, samples designated as 6-25A, 6-25B, 6-26A, 6-26B, 6-16C, 5-22-004, 5-22-005, 5-22-006, 5-22-007, 5-22-008, 5-22-009, 5-22-010 and 6-16, as well as others, were all deemed to be inferior or not acceptable (i.e., they did not include one or more (or all) of the beneficial characteristics that are described herein). It was also determined that hydrocortisone containing compositions and base formulations that did not include the ingredient Finsolv TN exhibited a problem with consistency over time as they deteriorated over time, thereby producing an undesirable gritty consistency. Finsolv TN is, thus, an important ingredient for inclusion in the hydrocortisone-containing and other active-agent containing compositions and base formulations of the invention.

After many different topical hydrocortisone-containing formulations were produced, and after a very significant amount of experimentation and testing of the same on human beings, it was determined that the topical hydrocortisone-containing composition, and related base compositions, that include the particular ingredients that are described herein, and the particular percent weights thereof have the very beneficial and advantageous characteristics that are described herein.

EXAMPLE 2

Preparation of a Hydrocortisone Composition (not Including Flavoring)

Initial Formulation

A batch of the same formulation that is described in Example 1 was prepared in the same manner as is described in Example 1, with the exception that this batch did not include any flavoring. To compensate for the absence of the 0.5 weight percent flavoring in this batch, additional castor oil was employed, bringing the total weight percent of castor oil up to 12 weight percent. This batch of the formulation was designated as batch LTC#6-47 AH, and contained the components, and weight percents thereof, that are set forth below.

| Ingredient | Weight Percent |
| --- | --- |
| Hydrocortisone | 1.0 |
| FANCOL VB | 11.0 |
| Natunola Castor 1023 | 18.0 |
| Finsolv TN | 11.0 |
| Bees Wax | 20.0 |
| Castor Oil | 12.0 |
| Stearyl Alcohol | 20.0 |
| Cocoa Butter | 7.0 |
| Flavoring (Vanilla) | 0.0 |
| TOTAL | 100 |

EXAMPLE 3

Preparation of a Base Composition (not Including Flavoring or Hydrocortisone)

Initial Formulation

A batch of the same formulation that is described in Example 1 was prepared in the same manner as is described in Example 1, with the exception that this batch did not include any flavoring or any hydrocortisone. To compensate for the absence of the 0.5 weight percent flavoring and the 1.0 weight percent hydrocortisone in this batch, additional castor oil was employed, bringing the total weight percent of castor oil up to 13%. This batch of the formulation was designated as batch LTC#6-47 A, and contained the components, and weight percents thereof, that are set forth below.

| Ingredient | Weight Percent |
| --- | --- |
| Hydrocortisone | 0.0 |
| FANCOL VB | 11.0 |
| Natunola Castor 1023 | 18.0 |
| Finsolv TN | 11.0 |
| Bees Wax | 20.0 |
| Castor Oil | 13.0 |
| Stearyl Alcohol | 20.0 |
| Cocoa Butter | 7.0 |
| Flavoring (Vanilla) | 0.0 |
| TOTAL | 100 |

EXAMPLE 4

Testing of Hydrocortisone Composition Prepared in Example 1 on Forearm, Wrist and Face of a Sixteen-Year-Old Male Patient Having Eczema In the three topical skin treatment experiments that are described below, a hydrocortisone formulation prepared as described in Example 1 in a form of a large solid stick was applied to various areas of the skin of a sixteen-year-old male patient at varying application rates (of about 0.5 ml/application), as is described below, using a roll-up applicator, as is shown in FIG. 1. These experiments were conducted by Joel Schlessinger, M.D., FAAD, FAACS, a board certified dermatologist and cosmetic surgeon.

Figure 2:
FIG. 2 is a photograph showing the left forearm of a sixteen-year-old male patient with eczema, as the forearm was present prior to receiving any type of treatment for the two plaques (elevated, solid, superficial lesions greater than 0.5 cm in diameter) appearing thereon.
Figure 3:
FIG. 3 is a photograph showing the same forearm (with two plaques) that is shown in FIG. 2 (i.e., a view that is closer up).
Figure 5:
FIG. 5 is a photograph showing the same forearm that is shown in FIG. 2, but as the forearm existed after being treated only with a hydrocortisone-containing solid composition of the invention, prepared in the manner described in Example 1, and having the larger size shown in FIG. 1, with twenty applications of about 0.5 ml/application of the composition being applied to the forearm spaced equally apart over a period of seven days.

In a first experiment, the composition was applied to the left forearm of the male patient, who had eczema on this forearm. FIGS. 2 and 3 are photographs showing the left forearm of the patient (with eczema) as the forearm existed prior to receiving any type of treatment for the eczema. FIGS. 2 and 3 show the forearm having two plaques (elevated, solid, superficial lesions greater than 0.5 cm in diameter) present in the skin of the forearm. FIG. 5 is a photograph showing the same forearm that is shown in FIGS. 2 and 3, but as the forearm existed after being treated only with the hydrocortisone-containing composition of the invention, with twenty applications of the composition being applied to the forearm spaced equally apart over a period of seven days. FIG. 5 shows that the two eczema plaques that are present on the forearm shown in FIGS. 2 and 3 completely disappeared after such treatment (i.e., the skin on the forearm was fully healed).

Figure 4:
FIG. 4 is a photograph showing the left wrist of the same male patient discussed in FIGS. 2 and 3, as the wrist was present prior to receiving any type of treatment for the eczema appearing thereon.

In a second experiment, the composition was applied to the left wrist of the same male patient, who had eczema on this wrist. FIG. 4 is a photograph showing the left wrist of the patient (with eczema) as the wrist existed prior to receiving any type of treatment for the eczema. FIG. 5 is a photograph showing the same wrist that is shown in FIG. 4, but as the wrist existed after being treated only with the hydrocortisone-containing composition of the invention, with thirty applications of the composition being applied to the wrist spaced equally apart over a period of seven days. FIG. 5 shows that the eczema that is present on the wrist in FIG. 4 completely disappeared after such treatment (i.e., the skin on the wrist was fully healed).

Figure 6:
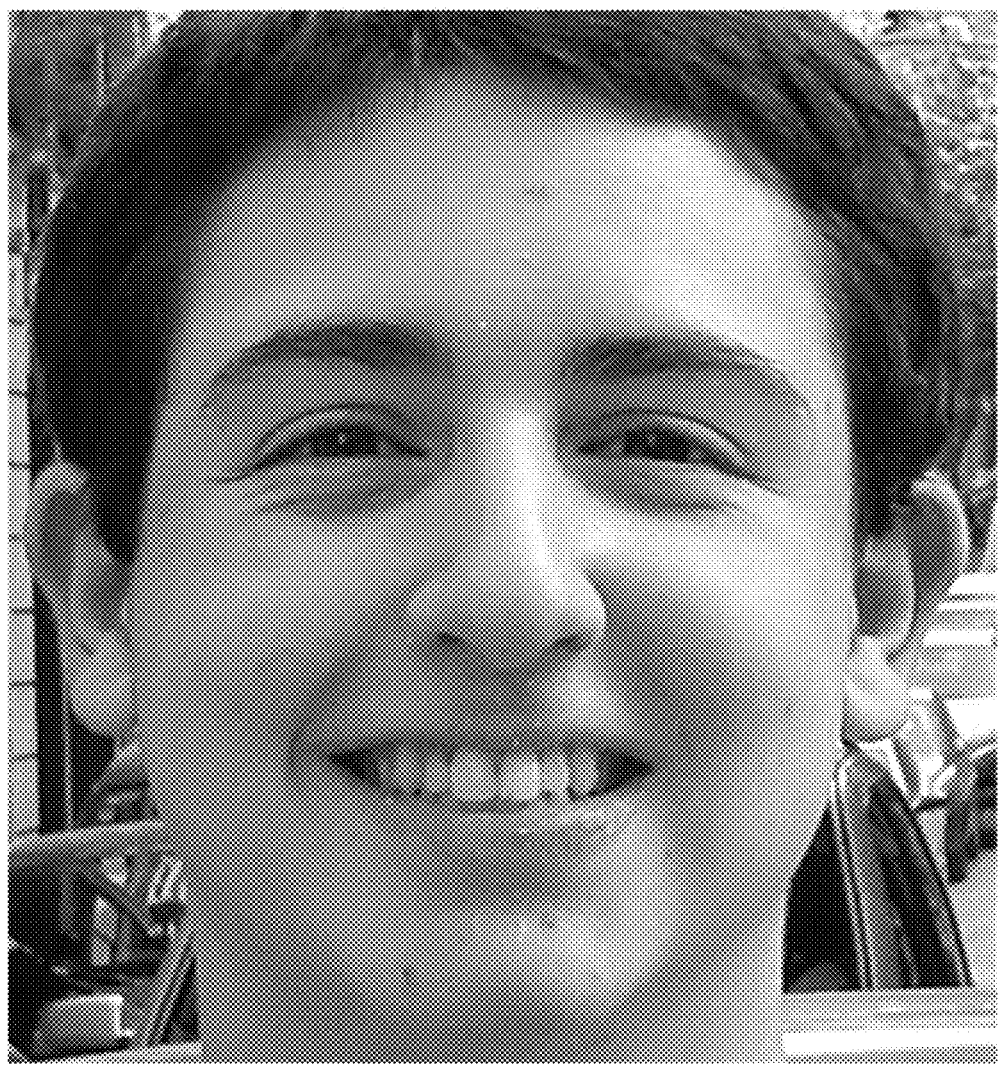
FIG. 6 is a photograph showing the full face of the same male patient discussed in FIGS. 2 and 3, as the face was present prior to receiving any type of treatment for the dry skin appearing thereon.
Figure 7:
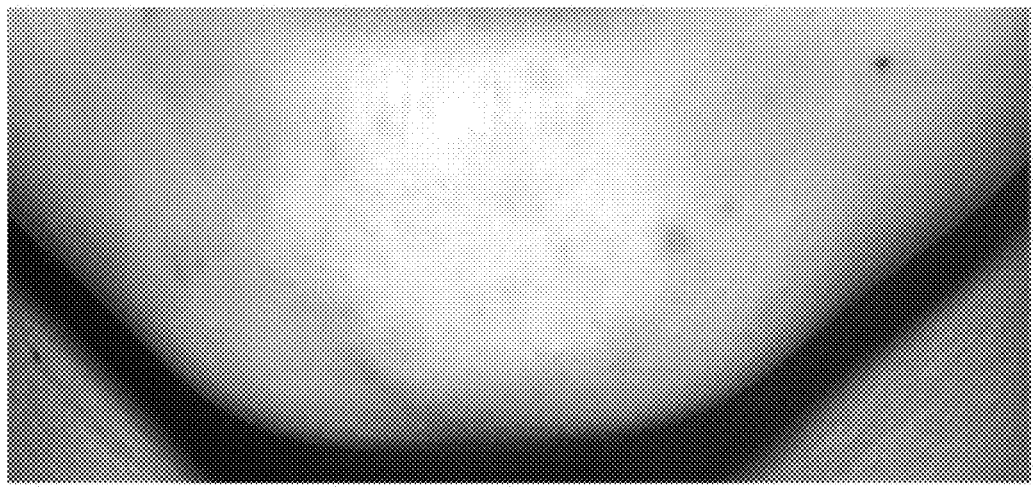
FIG. 7 is a photograph showing the chin area (with eczema) of the same face that is shown in FIG. 6 (i.e., a view that is closer up).
Figure 8:
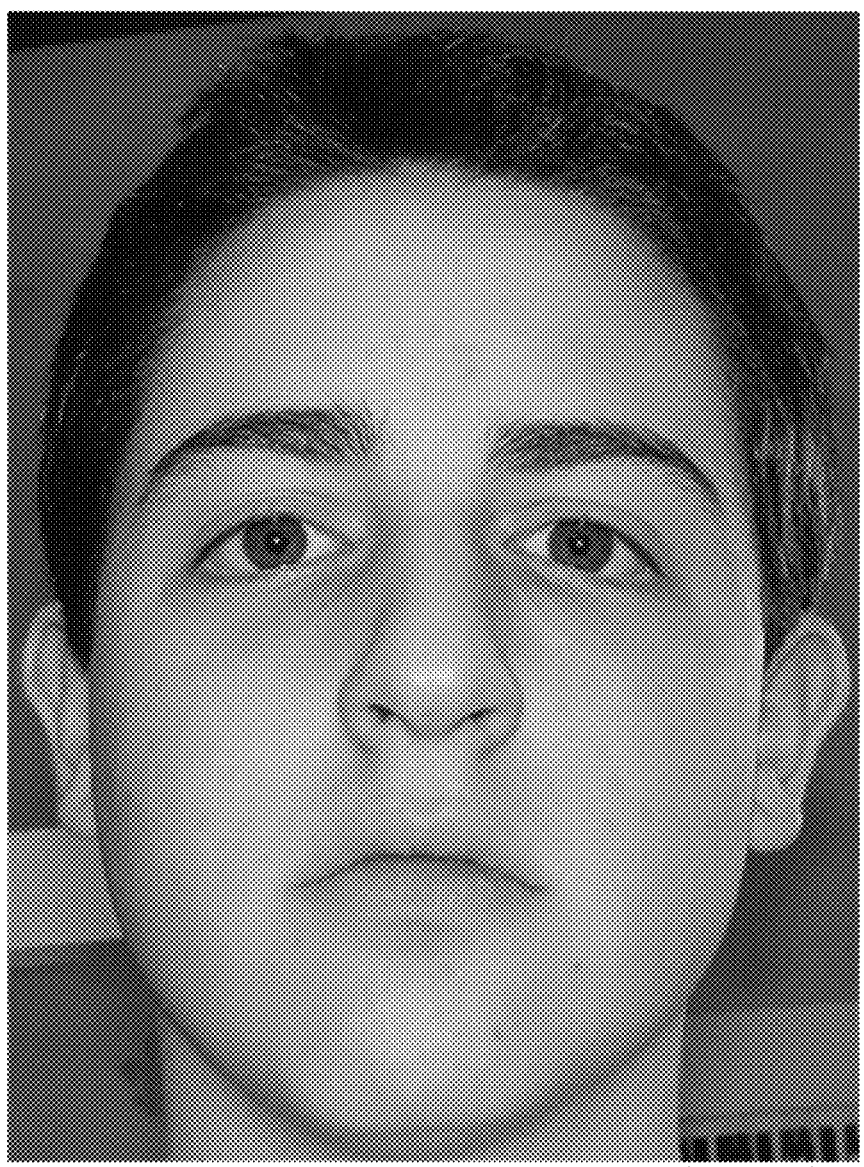
FIG. 8 is a photograph showing the same face that is shown in FIG. 6 (including the same chin that is shown in FIG. 7), but as the face (and chin) existed after being treated only with a hydrocortisone-containing solid composition of the invention, prepared in the manner described in Example 1, and having the larger size shown in FIG. 1, with twenty applications of about 0.5 ml/application being applied to the face spaced equally apart over a period of seven days.

In a third experiment, the composition was applied to the face of the same male patient, who had very dry lips, as well as eczema on the chin. FIG. 6 is a photograph showing the full face of the patient (with dry lips and eczema on the chin) as the face existed prior to receiving any type of treatment for the dry lips and eczema on the chin. FIG. 7 is a photograph showing the chin area (with eczema) of the same face that is shown in FIG. 6 (i.e., a view that is closer up). FIG. 8 is a photograph showing the same face that is shown in FIG. 6 (including the same chin that is shown in FIG. 7), but as the face (and chin) existed after being treated only with the hydrocortisone-containing composition of the invention, with ten applications of the composition being applied to the face (including the lips and chin) spaced equally apart over a period of seven days. FIG. 8 shows that the eczema on the chin in FIGS. 6 and 7 completely disappeared (i.e., the skin on the chin was fully healed), and that the lips no longer were dry.

EXAMPLE 5

Testing of Hydrocortisone Composition Prepared in Example 1 on Various Body Parts (Face, Cheeks, Chin, Lips, Fingers, Hands or Arms) of Eleven Other Patients Having Different Skin Disorders (Eczema, Cuts, Cracks, Peeling, Rashes, Irritation or Excessive Dryness)

In the topical skin treatment testing experiments that are described below, a hydrocortisone formulation of the invention, prepared as is described in Example 1, and in a form of a solid stick, was applied to various areas of the skin of eleven other human beings (patients) in varying quantities and at varying application rates, as is described below, using a roll-up applicator, as is shown in FIG. 1. Detailed patient feedback was subsequently provided to Joel Schlessinger, M.D., FAAD, FAACS, a board certified dermatologist and cosmetic surgeon, who oversaw each of these experiments, and is described below.

The test subjects used for these studies were both male and female patients ranging from sixteen to seventy-eight years of age.

A control formulation was also employed in some of these studies. The control product was a formulation described in U.S. Pat. No. 6,228,351 in most cases or an "over-the-counter" (non-prescription) lip balm or medication that was prescription in nature (i.e., prescribed by a medical doctor).

Initial applications of the hydrocortisone formation, and of the control formulation, topically to the skin of the test subjects, and instructions for subsequent applications, were supervised by Joel Schlessinger, M.D., FAAD, FAACS.

A variety of application procedures were employed with respect to number of applications of a test material and duration of applications in an attempt to reflect actual real world usage of these types of products, as well as to determine the extent to which observed results were a function of duration and/or frequency of use. The application protocols (frequency and duration of use) varied as is discussed below. Each test subject applied the hydrocortisone formulation, and separately the control, to the areas of his or her lips or body that are described below.

Patient Designated "TS," Age 17, Male: Tested the formulation on his lips, and liked the formulation, stating that it helped his lips to heal. The composition was applied over a two-month period and approximately five times per day.

Patient Designated "KS," Age 60, Female: Tested the formulation on an eczematous area on her cheek, and liked the formulation, stating that it healed the eczematous area on her cheek. The composition was applied over a four-month period and two to three times daily.

Patient Designated "LLH," Female, Age 28: Tested the formulation on her fingers and subsequently stated, "While it is a bit waxy in feeling, it was a rather clean appearance while doing magic for my condition on fingers." The composition was applied over a two-month period and two times daily.

Patient Designated "MW," Male, Age 22: Tested the formulation on his lips for excessive dryness and subsequently stated, "I have been using the lip balm and it seems to be working." The composition was applied over a three-month period and four times daily on average.

Patient Designated "JB," Male, Age 25: Tested the formulation on her face for facial dryness and subsequently stated, "I have been using it. It works very well." The composition was applied over a three-month period and twice daily.

Patient Designated "EC," Female, Age 78: Tested the formulation on her lips for irritation and subsequently stated, "No irritation of lips now." The composition was applied over a six-month period and six times daily.

Patient Designated "DS," Male, Age 16: Tested the formulation on his fingers, hands, cheeks, chin, lips and arms in connection with rashes and subsequently stated, "Worked wonderfully on my fingers, hands, cheeks, chin, lips and arms to clear up rashes." The composition was applied over an eight-month period and approximately four times daily for the lips and chin and three times daily for the body and hands.

Patient Designated "JHS," Female, Age 76: Tested the formulation on her fingers in connection with dry skin and cuts and subsequently stated, "Liked the taste, and it was especially helpful for my dry skin on the fingers and cuts." The composition was applied over a four-month period twice daily for the lips and fingers.

Patient Designated "JS," Male, Age 50: Tested the formulation on his fingers in connection with dry skin and subsequently stated, "This worked very nicely for me and helped my fingers when they were dry." The composition was applied over a nine-month period twice daily.

Patient Designated "SH," Female, Age 35: Tested the formulation on her dry lips and subsequently stated, "I was struggling with my lips becoming so dry. I told you about my concerns, dry, peeling, and my bottom lip would crack in the middle, it was very painful. You had me test your trial lip balm, and I absolutely loved it, and still love it. I would put it on at night for bedtime, and after two applications my lips were soft and perfect." The composition was applied over a five-month period at approximately twice daily.

Patient Designated "RMS," Female, Age 26: Tested the formulation on her dry hands and subsequently stated, "It worked really well. I was having pretty significant cracking due to the dry air and repeated hand washing. It was thick and protective and helped to heal the areas faster than any moisturizers I had tried. It was nice also to just put it on the trouble areas and not have a thick product over my entire hands." The composition was applied over a four-month period, using it three times daily on the areas.

EXAMPLE 6

Preparation of Another Hydrocortisone Composition (Including Vanilla Flavoring)

Improved Formulation—OTC

A batch of a preferred OTC vanilla-flavored hydrocortisone-containing topical skin formulation of the present invention was prepared in the manner described below. The composition contained the components, and weight percents thereof, that are set forth below.

| Ingredient | Weight Percent |
| --- | --- |
| Hydrocortisone | 1.00 |
| FANCOL VB | 11.00 |
| Natunola Castor 1023 | 10.00 |
| FINSOLV TN | 15.00 |
| Bees Wax | 11.00 |
| Castor Oil | 24.50 |
| Stearyl Alcohol | 20.00 |
| Cocoa Butter | 7.00 |
| Vanilla Flavoring | 0.50 |
| TOTAL | 100 |

60.88 pounds of castor oil were added to a standard stainless steel drum including a mixer and heated using Heating Bands (Expo Engineered Inc., Cicero, Ill.) to a temperature ranging from about 75° C. to about 85° C., while stirring it continuously using the mixer.

27.50 pounds of FANCOL VB were added to the castor oil in the drum, and mixed with the castor oil until it was completely dissolved therein, which took about 30 minutes, while maintaining a temperature ranging from about 75° C. to about 85° C.

27.50 pounds of bees wax were then added to the above mixture of castor oil and FANCOL VB in the drum while a temperature ranging from about 75° C. to about 85° C. was maintained. Mixing of the ingredients was continued for about 30 minutes, which was sufficient to completely dissolve the bees wax therein.

50.00 pounds of stearyl alcohol were then added to the above mixture in the drum while a temperature ranging from about 75° C. to about 85° C. was maintained. Mixing was continued for a period of about 30 minutes, which was sufficient to completely dissolve the stearyl alcohol therein.

17.50 pounds of cocoa butter were then added to the above mixture in the drum while a temperature ranging from about 75° C. to about 85° C. was maintained. Mixing was continued for about 30 minutes, which was sufficient to completely dissolve the cocoa butter therein.

37.50 pounds of FINSOLV TN were then added to the above mixture in the drum while a temperature ranging from about 75° C. to about 85° C. was maintained. Mixing was continued for a period of about 30 minutes, which was sufficient to completely dissolve the FINS OLV TN therein.

25.00 pounds of Natunola 1023 were added to the above mixture in the drum while a temperature ranging from about 75° C. to about 85° C. was maintained. Mixing of the ingredients was then continued for about 60 minutes.

The above mixture was mixed for an additional 30-60 minutes, which was sufficient to have any remaining particles present therein to be completely dissolved in the mixture, while a temperature ranging from about 75° C. to about 85° C. was maintained.

2.88 pounds of hydrocortisone were then added to the above mixture and mixed until it dissolved therein, which took about 30 minutes, while maintaining the temperature of the mixture ranging from about 75° C. to about 85° C.

The resulting mixture was then permitted to cool naturally to a temperature ranging from about 70° C. to about 80° C.

1.25 pounds of vanilla flavoring were added to the above mixture in the drum while a temperature ranging from about 70° C. to about 80° C. was maintained. Mixing of the ingredients was then continued for about 15-20 minutes.

The resulting mixture was liquid in nature, light yellow in color, and had a general appearance of a thin milky liquid.

Once the sample (mixture) was found to be acceptable (i.e., to possess the above characteristics), the entire batch of the composition was transferred to the filling area, where it was manually poured into the individual plastic containers to form the following shapes and sizes:

(i) a 0.15 fluid ounce stick-shaped roll-up skin balm measuring about 6.0 cm in length and about 1.5 cm in diameter (a suitable size for a lip balm);

(ii) a 0.50 fluid ounce stick-shaped roll-up skin balm measuring about 7.6 cm in length and about 2.0 cm in diameter (a suitable size for a body balm); and (iii) a 0.25 fluid ounce jar-shaped skin balm measuring about 3.0 cm in length and about 3.3 cm in diameter (a suitable size for a face balm).

After the compositions settled and hardened in the containers, which generally took about 60 minutes, a container cap made of plastic material was placed onto the open end of each container and then a label including a batch code and expiration date was placed onto either the label or the container.

A sample of the finished product was then analyzed using High Performance Liquid Chromatography (HPLC) or Gas Chromatography (GC) to detect the percentage of hydrocortisone for characteristics of one percent hydrocortisone. Also, a sample of the finished product was tested to confirm its compliance with an established U.S. specification for microbiological quality using the known USP Microbial Limits Test, which is described in Chapter 61 and 62 of the U.S. Pharmacopeia (USP) for Microbial Limits, which is hereby incorporated herein by reference in its entirety.

The topical skin formulation that was prepared in this example may be contained in stick, jar, pot and/or other suitable or desirable containers (of a wide variety of different shapes, sizes and materials) including the above, or other suitable or desirable, quantities thereof.

EXAMPLE 7

Preparation of another Hydrocortisone Composition (Not Including any Flavoring)

Improved Formulation—OTC

A batch of another preferred OTC hydrocortisone skin formulation of the present invention in the form of a roll-up balm was prepared in the manner described in Example 6, and designated as batch LTC#6-47 AH. This composition differed from the composition described in Example 6 in that it did not include any flavoring. The composition contained the components, and weight percents thereof, that are set forth in Example 6, with the exceptions that no flavoring component was included, and an additional 0.5 weight percent of Castor Oil was included (in place of the 0.5 weight percent of flavoring), as is shown below.

| Ingredient | Weight Percent |
| --- | --- |
| Hydrocortisone | 1.00 |
| FANCOL VB | 11.00 |
| Natunola Castor 1023 | 10.00 |
| FINSOLV TN | 15.00 |
| Bees Wax | 11.00 |

-continued

| Ingredient | Weight Percent |
| --- | --- |
| Castor Oil | 25.00 |
| Stearyl Alcohol | 20.00 |
| Cocoa Butter | 7.00 |
| TOTAL | 100 |

62.13 pounds of castor oil were added to a standard stainless steel drum including a mixer and heated using Heating Bands to a temperature ranging from about 75° C. to about 85° C., while stirring it continuously using the mixer.

27.50 pounds of FANCOL VB were added to the castor oil in the drum, and mixed with the castor oil until it was completely dissolved therein, which took about 30 minutes, while maintaining a temperature ranging from about 75° C. to about 85° C.

27.50 pounds of bees wax were then added to the above mixture of castor oil and FANCOL VB in the drum while a temperature ranging from about 75° C. to about 85° C. was maintained. Mixing of the ingredients was continued for about 30 minutes, which was sufficient to completely dissolve the bees wax therein.

50.00 pounds of stearyl alcohol were then added to the above mixture in the drum while a temperature ranging from about 75° C. to about 85° C. was maintained. Mixing was continued for a period of about 30 minutes, which was sufficient to completely dissolve the stearyl alcohol therein.

17.50 pounds of cocoa butter were then added to the above mixture in the drum while a temperature ranging from about 75° C. to about 85° C. was maintained. Mixing was continued for about 30 minutes, which was sufficient to completely dissolve the cocoa butter therein.

37.50 pounds of FINSOLV TN were then added to the above mixture in the drum while a temperature ranging from about 75° C. to about 85° C. was maintained. Mixing was continued for a period of about 30 minutes, which was sufficient to completely dissolve the FINSOLV TN therein.

25.00 pounds of Natunola 1023 were added to the above mixture in the drum while a temperature ranging from about 75° C. to about 85° C. was maintained. Mixing of the ingredients was then continued for about 60 minutes.

The above mixture was mixed for an additional 30-60 minutes, which was sufficient to have any remaining particles present therein to be completely dissolved in the mixture, while a temperature ranging from about 75° C. to about 85° C. was maintained.

2.88 pounds of hydrocortisone were then added to the above mixture and mixed until it dissolved therein, which took about 30 minutes, while maintaining the temperature of the mixture ranging from about 75° C. to about 85° C. The resulting mixture was liquid in nature, light yellow in color, and had a general appearance of a thin milky liquid.

Once the sample (mixture) was found to be acceptable (i.e., to possess the above characteristics), the entire batch of the composition was transferred to the filling area, where it was manually poured into the individual plastic containers to form the following shapes and sizes:
  (i) a 0.15 fluid ounce stick-shaped roll-up skin balm measuring about 6.0 cm in length and about 1.5 cm in diameter (a suitable size for a lip balm);
  (ii) a 0.50 fluid ounce stick-shaped roll-up skin balm measuring about 7.6 cm in length and about 2.0 cm in diameter (a suitable size for a body balm); and
  (iii) a 0.25 fluid ounce jar-shaped skin balm measuring about 3.0 cm in length and about 3.3 cm in diameter (a suitable size for a face balm).

After the compositions settled and hardened in the containers, which generally took about 60 minutes, a container cap made of plastic material was placed onto the open end of each container and then a label including a batch code and expiration date was placed onto either the label or the container.

A sample of the finished product was then analyzed using High Performance Liquid Chromatography (HPLC) or Gas Chromatography (GC) to detect the percentage of hydrocortisone for characteristics of one percent hydrocortisone. Also, a sample of the finished product was tested to confirm its compliance with an established U.S. specification for microbiological quality using the known USP Microbial Limits Test.

The topical skin formulation that was prepared in this example may be contained in stick, jar, pot and/or other suitable or desirable containers (of a wide variety of different shapes, sizes and materials) including the above, or other suitable or desirable, quantities thereof.

EXAMPLE 8

Preparation of Another Base Composition (not Including Hydrocortisone, but Including Vanilla Flavoring)

Improved Formulation—Non-OTC

A batch of a preferred non-OTC, vanilla-flavored, topical base composition of the present invention (not including hydrocortisone or any other active agent) was prepared in the manner described below. The base composition contained the components, and weight percents thereof, that are set forth below.

| Ingredient | Weight Percent |
| --- | --- |
| FANCOL VB | 11.00 |
| Natunola Castor 1023 | 10.00 |
| FINSOLV TN | 15.00 |
| Bees Wax | 11.00 |
| Castor Oil | 25.50 |
| Stearyl Alcohol | 20.00 |
| Cocoa Butter | 7.00 |
| Vanilla Flavoring | 0.50 |
| TOTAL | 100 |

63.75 pounds of castor oil were added to a standard stainless steel drum including a mixer and heated using Heating Bands to a temperature ranging from about 75° C. to about 85° C., while stirring it continuously using the mixer.

27.50 pounds of FANCOL VB were added to the castor oil in the drum, and mixed with the castor oil until it was completely dissolved therein, which took about 30 minutes, while maintaining a temperature ranging from about 75° C. to about 85° C.

27.50 pounds of bees wax were then added to the above mixture of castor oil and FANCOL VB in the drum while a temperature ranging from about 75° C. to about 85° C. was maintained. Mixing of the ingredients was continued for about 30 minutes, which was sufficient to completely dissolve the bees wax therein.

50.00 pounds of stearyl alcohol were then added to the above mixture in the drum while a temperature ranging from about 75° C. to about 85° C. was maintained. Mixing was continued for a period of about 30 minutes, which was sufficient to completely dissolve the stearyl alcohol therein.

17.50 pounds of cocoa butter were then added to the above mixture in the drum while a temperature ranging from about 75° C. to about 85° C. was maintained. Mixing was continued for about 30 minutes, which was sufficient to completely dissolve the cocoa butter therein.

37.50 pounds of FINS OLV TN were then added to the above mixture in the drum while a temperature ranging from about 75° C. to about 85° C. was maintained. Mixing was continued for a period of about 30 minutes, which was sufficient to completely dissolve the FINSOLV TN therein.

25.00 pounds of Natunola 1023 were added to the above mixture in the drum while a temperature ranging from about 75° C. to about 85° C. was maintained. Mixing of the ingredients was then continued for about 60 minutes.

The above mixture was mixed for an additional 30-60 minutes, which was sufficient to have any remaining particles present therein to be completely dissolved in the mixture, while a temperature ranging from about 75° C. to about 85° C. was maintained.

The resulting mixture was then permitted to cool naturally to a temperature ranging from about 70° C. to about 80° C.

1.25 pounds of vanilla flavoring were added to the above mixture in the drum while a temperature ranging from about 70° C. to about 80° C. was maintained. Mixing of the ingredients was then continued for about 15-20 minutes.

The resulting mixture was liquid in nature, light yellow in color, and had a general appearance of a thin milky liquid.

Once the sample (mixture) was found to be acceptable (i.e., to possess the above characteristics), the entire batch of the composition was transferred to the filling area, where it was manually poured into the individual plastic containers to form the following shapes and sizes:

(i) a 0.15 fluid ounce stick-shaped roll-up skin balm measuring about 6.0 cm in length and about 1.5 cm in diameter (a suitable size for a lip balm);

(ii) a 0.50 fluid ounce stick-shaped roll-up skin balm measuring about 7.6 cm in length and about 2.0 cm in diameter (a suitable size for a body balm); and (iii) a 0.25 fluid ounce jar-shaped skin balm measuring about 3.0 cm in length and about 3.3 cm in diameter (a suitable size for a face balm).

After the compositions settled and hardened in the containers, which generally took about 60 minutes, a container cap made of plastic material was placed onto the open end of each container and then a label including a batch code and expiration date was placed onto either the label or the container.

A sample of the finished product was then analyzed using High Performance Liquid Chromatography (HPLC) or Gas Chromatography (GC), and tested to confirm its compliance with an established U.S. specification for microbiological quality using the known USP Microbial Limits Test.

The base composition that was prepared in this example may be contained in stick, jar, pot and/or other suitable or desirable containers (of a wide variety of different shapes, sizes and materials) including the above, or other suitable or desirable, quantities thereof.

EXAMPLE 9

Preparation of Another Base Composition (not Including Hydrocortisone or any Flavoring)

Improved Formulation—Non-OTC

A batch of a preferred non-OTC, unflavored, topical base composition of the present invention (not including hydrocortisone or any other active agent) was prepared in the manner described below. The base composition contained the components, and weight percents thereof, that are set forth below.

| Ingredient | Weight Percent |
| --- | --- |
| FANCOL VB | 11.00 |
| Natunola Castor 1023 | 10.00 |
| FINSOLV TN | 15.00 |
| Bees Wax | 11.00 |
| Castor Oil | 26.00 |
| Stearyl Alcohol | 20.00 |
| Cocoa Butter | 7.00 |
| TOTAL | 100 |

65.00 pounds of castor oil were added to a standard stainless steel drum including a mixer and heated using Heating Bands to a temperature ranging from about 75° C. to about 85° C., while stirring it continuously using the mixer.

27.50 pounds of FANCOL VB were added to the castor oil in the drum, and mixed with the castor oil until it was completely dissolved therein, which took about 30 minutes, while maintaining a temperature ranging from about 75° C. to about 85° C.

27.50 pounds of bees wax were then added to the above mixture of castor oil and FANCOL VB in the drum while a temperature ranging from about 75° C. to about 85° C. was maintained. Mixing of the ingredients was continued for about 30 minutes, which was sufficient to completely dissolve the bees wax therein.

50.00 pounds of stearyl alcohol were then added to the above mixture in the drum while a temperature ranging from about 75° C. to about 85° C. was maintained. Mixing was continued for a period of about 30 minutes, which was sufficient to completely dissolve the stearyl alcohol therein.

17.50 pounds of cocoa butter were then added to the above mixture in the drum while a temperature ranging from about 75° C. to about 85° C. was maintained. Mixing was continued for about 30 minutes, which was sufficient to completely dissolve the cocoa butter therein.

37.50 pounds of FINS OLV TN were then added to the above mixture in the drum while a temperature ranging from about 75° C. to about 85° C. was maintained. Mixing was continued for a period of about 30 minutes, which was sufficient to completely dissolve the FINSOLV TN therein.

25.00 pounds of Natunola 1023 were added to the above mixture in the drum while a temperature ranging from about 75° C. to about 85° C. was maintained. Mixing of the ingredients was then continued for about 60 minutes.

The above mixture was mixed for an additional 30-60 minutes, which was sufficient to have any remaining particles present therein to be completely dissolved in the mixture, while a temperature ranging from about 75° C. to about 85° C. was maintained.

The resulting mixture was liquid in nature, light yellow in color, and had a general appearance of a thin milky liquid.

Once the sample (mixture) was found to be acceptable (i.e., to possess the above characteristics), the entire batch of the composition was transferred to the filling area, where it was manually poured into the individual plastic containers to form the following shapes and sizes:

(i) a 0.15 fluid ounce stick-shaped roll-up skin balm measuring about 6.0 cm in length and about 1.5 cm in diameter (a suitable size for a lip balm);

(ii) a 0.50 fluid ounce stick-shaped roll-up skin balm measuring about 7.6 cm in length and about 2.0 cm in diameter (a suitable size for a body balm); and (iii) a 0.25 fluid ounce jar-shaped skin balm measuring about 3.0 cm in length and about 3.3 cm in diameter (a suitable size for a face balm).

After the compositions settled and hardened in the containers, which generally took about 60 minutes, a container cap made of plastic material was placed onto the open end of each container and then a label including a batch code and expiration date was placed onto either the label or the container.

A sample of the finished product was then analyzed using High Performance Liquid Chromatography (HPLC) or Gas Chromatography (GC), and tested to confirm its compliance with an established U.S. specification for microbiological quality using the known USP Microbial Limits Test.

The base composition that was prepared in this example may be contained in stick, jar, pot and/or other suitable or desirable containers (of a wide variety of different shapes, sizes and materials) including the above, or other suitable or desirable, quantities thereof.

EXAMPLE 10

Testing of Hydrocortisone Composition Prepared in Example 6 on Left and Right Hands of Fifty-Year-Old Female Patient Having Psoriasis In the topical skin treatment experiments that are described below, a hydrocortisone formulation prepared as described in Example 6 in a form of a large solid stick (including approximately 14.78 ml of the formulation), was applied to the left and right hands (both sides of each hand) of a fifty-year-old female patient having psoriasis, whose initials are PT, at an application rate of about 100 applications of about 0.5 ml/application of the composition being equally spaced apart over a period of 30 days (i.e., about 3-4 applications per day). These experiments were conducted by Joel Schlessinger, M.D., FAAD, FAACS, a board certified dermatologist and cosmetic surgeon.

Long prior to these experiments, this same female patient had tried to improve or eradicate the above-described skin disorders on her left and right hands using a wide variety of different known "over-the-counter" (non-prescription) and prescription (prescribed by a medical doctor) topical skin products, including balms, and those including one or more active agents, such as hydrocortisone. She tried numerous different forms of topical compositions including hydrocortisone on her hands, as well as other, more powerful forms of corticosteroids, oral medications and injectable medications. She, however, did not have success with any of these topical compositions or medications (i.e., her skin disorders were not significantly improved or eradicated by any of these compositions or medications), as can clearly be seen in each of the "before" photographs that are shown in FIGS. 9A, 10A, 11A, 12A, 13A and 14A (photographs taken before the experiments described in this example were preformed).

Figure 9A:
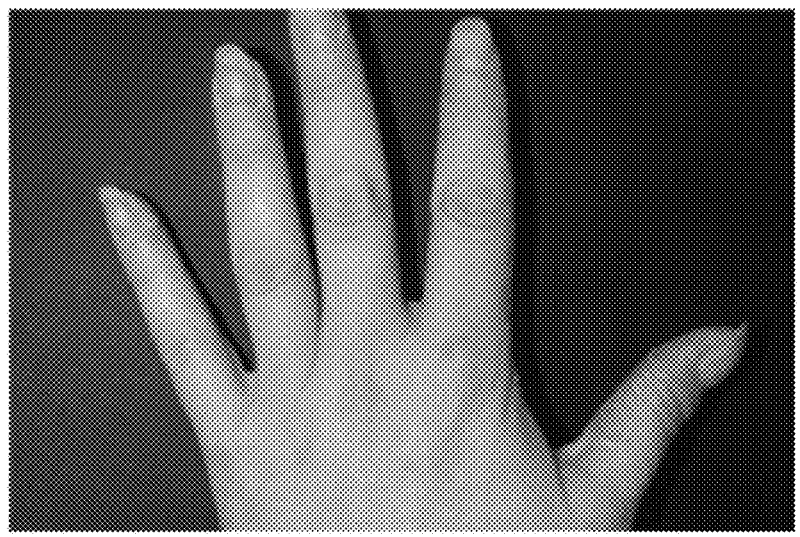
FIG. 9A shows this hand as it was present prior to receiving any type of treatment with any compositions of the invention for the dryness, cracks, and cuts appearing thereon, with an emphasis on the thumb and the index finger.
Figure 9B:
FIG. 9B shows the same dorsal aspect that is shown in FIG. 9A, but as this hand existed after being treated only with a hydrocortisone-containing solid composition of the invention in a form of a large solid stick, prepared in the manner described in Example 6, and having the larger size shown in FIG. 1, with about 100 applications of about 0.5 ml/application of the composition being applied to the palm spaced equally apart over a period of thirty days (i.e., about 3-4 applications per day). A comparison of the left hand that is shown in FIG. 9A with the left hand that is shown in FIG. 9B shows that the dryness and cracks that are shown in FIG. 9A are significantly moisturized and reduced, and that the cuts that are shown in FIG. 9A have completely disappeared (i.e., have a 100% improvement).

FIG. 9A shows the dorsal aspect of the left hand as it was present prior to receiving any type of treatment with a composition of the invention for the dryness, cracks, and cuts appearing thereon, with an emphasis on the thumb and the index finger. FIG. 9B shows the same dorsal aspect that is shown in FIG. 9A, but as this hand existed after being treated only with the hydrocortisone-containing solid composition (in the manner described above). A comparison of the left hand that is shown in FIG. 9A with the left hand that is shown in FIG. 9B shows that the dryness and cracks that are shown in FIG. 9A are significantly moisturized and reduced, and that the cuts that are shown in FIG. 9A have completely disappeared (i.e., have a 100% improvement).

Figure 10A:
FIG. 10A shows this hand as it was present prior to receiving any type of treatment with any compositions of the invention for the dryness, cracks, and cuts appearing thereon, with an emphasis on the thumb and the palm.
Figure 10B:
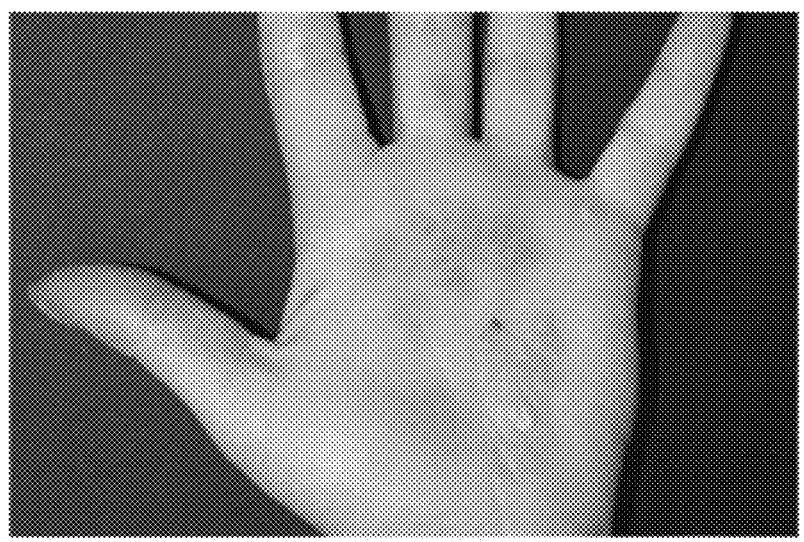
FIG. 10B shows the same palm that is shown in FIG. 10A, but as the palm existed after being treated only with a hydrocortisone-containing solid composition of the invention in a form of a large solid stick, prepared in the manner described in Example 6, and having the larger size shown in FIG. 1, with about 100 applications of about 0.5 ml/application of the composition being applied to the palm spaced equally apart over a period of thirty days (i.e., about 3-4 applications per day). A comparison of the left hand that is shown in FIG. 10A with the left hand that is shown in FIG. 10B shows that the dryness and cracks that are shown in FIG. 10A are significantly moisturized and reduced, and that the cuts that are shown in FIG. 10A have completely disappeared (i.e., have a 100% improvement).

FIG. 10A shows the palmar aspect of the same left hand as it was present prior to receiving any type of treatment with a composition of the invention for the dryness, cracks, and cuts appearing thereon, with an emphasis on the thumb and the palm. FIG. 10B shows the same palm that is shown in FIG. 10A, but as the palm existed after being treated only with the hydrocortisone-containing solid composition (in the manner described above). A comparison of the left hand that is shown in FIG. 10A with the left hand that is shown in FIG. 10B shows that the dryness and cracks that are shown in FIG. 10A are significantly moisturized and reduced, and that the cuts that are shown in FIG. 10A have completely disappeared (i.e., have a 100% improvement).

Figure 11A:
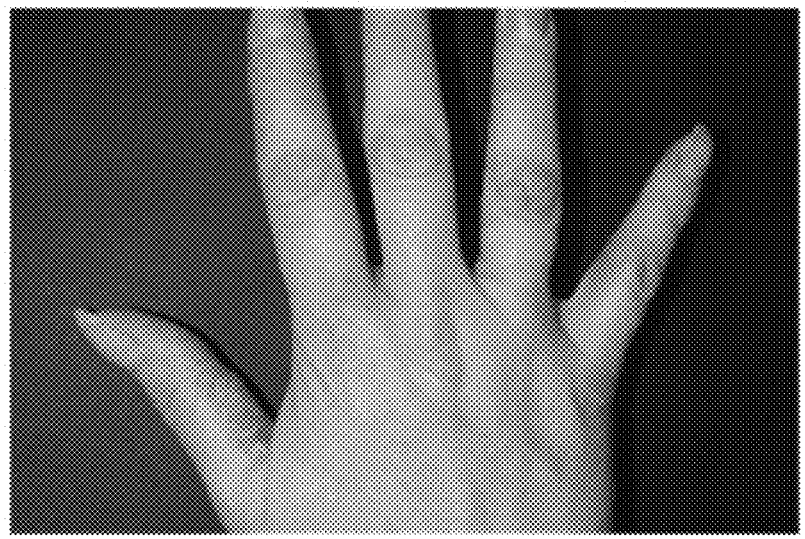
FIG. 11A shows this hand as it was present prior to receiving any type of treatment with any compositions of the invention for the dryness, cracks, and cuts appearing thereon, with an emphasis on the thumb, index finger, and knuckles.
Figure 11B:
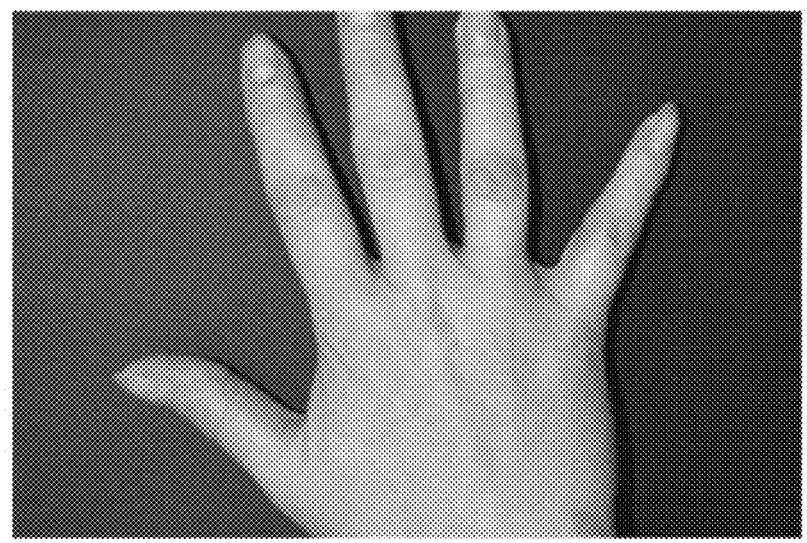
FIG. 11B shows the same dorsal aspect that is shown in FIG. 11A, but as the hand existed after being treated only with a hydrocortisone-containing solid composition of the invention in a form of a large solid stick, prepared in the manner described in Example 6, and having the larger size shown in FIG. 1, with about 100 applications of about 0.5 ml/application of the composition being applied to the palm spaced equally apart over a period of thirty days (i.e., about 3-4 applications per day). A comparison of the right hand that is shown in FIG. 11A with the right hand that is shown in FIG. 11B shows that the dryness and cracks that are shown in FIG. 11A are significantly moisturized and reduced, and that the cuts that are shown in FIG. 11A have completely disappeared (i.e., have a 100% improvement).

FIG. 11A shows the dorsal aspect of the right hand as it was present prior to receiving any type of treatment with a composition of the invention for the dryness, cracks, and cuts appearing thereon, with an emphasis on the thumb, index finger, and knuckles. FIG. 11B shows the same dorsal aspect that is shown in FIG. 11A, but as the hand existed after being treated only with the hydrocortisone-containing solid composition (in the manner described above). A comparison of the right hand that is shown in FIG. 11A with the right hand that is shown in FIG. 11B shows that the dryness and cracks that are shown in FIG. 11A are significantly moisturized and reduced, and that the cuts that are shown in FIG. 11A have completely disappeared (i.e., have a 100% improvement).

Figure 12A:
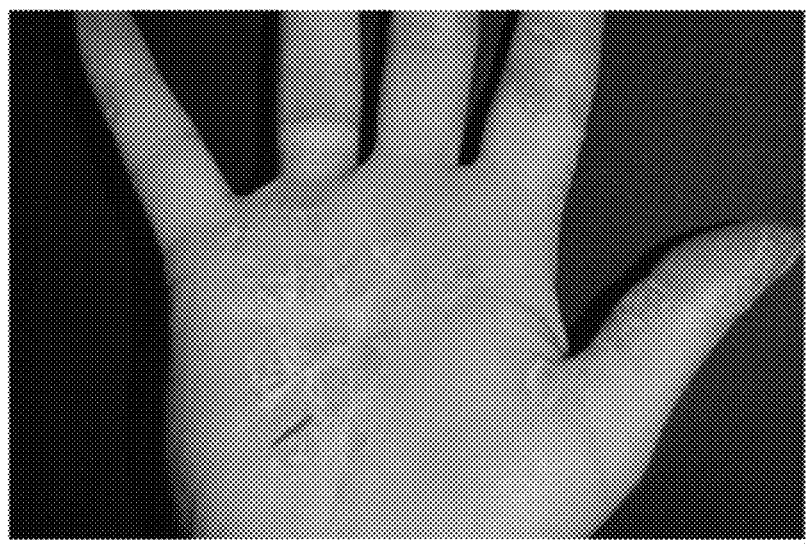
FIG. 12A shows this hand as it was present prior to receiving any type of treatment with any compositions of the invention for the dryness, cracks, and cuts appearing thereon, with an emphasis on the palm, thumb, and index finger.
Figure 12B:
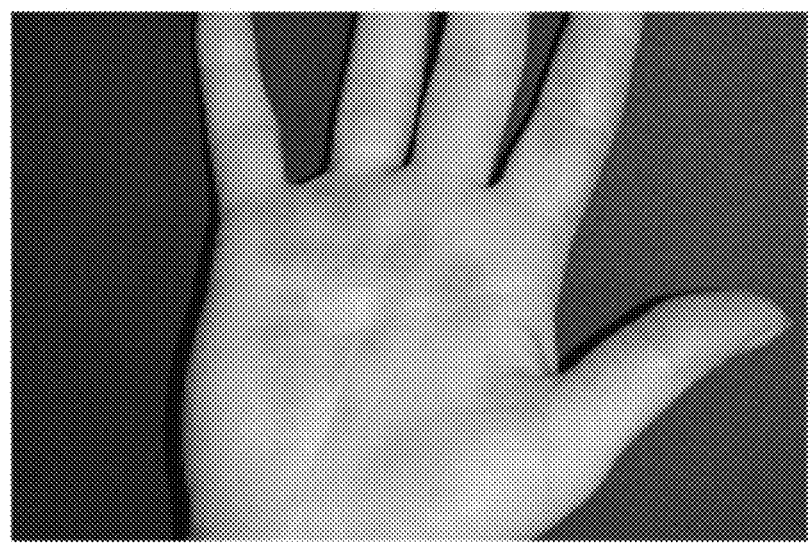
FIG. 12B shows the same palm that is shown in FIG. 12A, but as the palm existed after being treated only with a hydrocortisone-containing solid composition of the invention in a form of a large solid stick, prepared in the manner described in Example 6, and having the larger size shown in FIG. 1, with about 100 applications of about 0.5 ml/application of the composition being applied to the palm spaced equally apart over a period of thirty days (i.e., about 3-4 applications per day). A comparison of the right hand that is shown in FIG. 12A with the right hand that is shown in FIG. 12B shows that the dryness and cracks that are shown in FIG. 12A are significantly moisturized and reduced, and that the cuts that are shown in FIG. 12A have completely disappeared (i.e., have a 100% improvement).

FIG. 12A shows the palmar aspect of the right hand as it was present prior to receiving any type of treatment with a composition of the invention for the dryness, cracks, and cuts appearing thereon, with an emphasis on the palm, thumb, and index finger. FIG. 12B shows the same palm that is shown in FIG. 12A, but as the palm existed after being treated only with the hydrocortisone-containing solid composition (in the manner described above). A comparison of the right hand that is shown in FIG. 12A with the right hand that is shown in FIG. 12B shows that the dryness and cracks that are shown in FIG. 12A are significantly moisturized and reduced, and that the cuts that are shown in FIG. 12A have completely disappeared (i.e., have a 100% improvement).

FIG. 13A shows the same dorsal aspects of the same left and right hands, as they were present prior to receiving any type of treatment with a composition of the invention for the dryness, cracks, and cuts appearing thereon, with an emphasis on the thumbs, index fingers, and knuckles of both hands. FIG. 13B shows the same left and right hands that are shown in FIG. 13A, but as the left and right hands existed after being treated only with the hydrocortisone-containing solid composition (in the manner described above). A comparison of the left and right hands that are shown in FIG. 13A with the left and right hands that are shown in FIG. 13B shows that the dryness and cracks that are shown in FIG. 13A are significantly moisturized and reduced, and that the cuts that are shown in FIG. 13A have completely disappeared (i.e., have a 100% improvement).

Figure 14A:
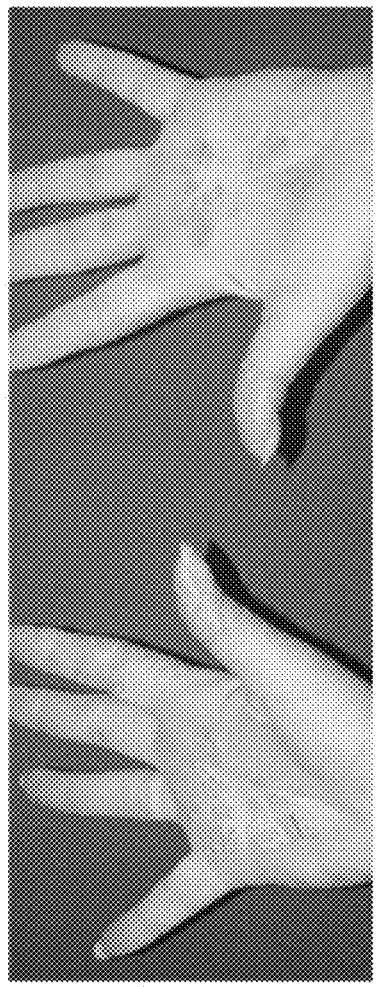
FIG. 14A shows the left and right hands as they were present prior to receiving any type of treatment with any compositions of the invention for the dryness, cracks, and cuts appearing thereon, with an emphasis on the palms, thumbs, and index fingers of both hands.
Figure 14B:
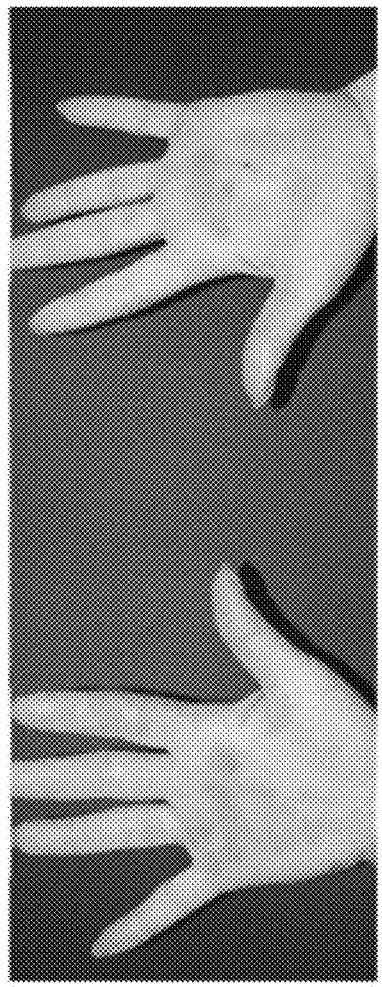
FIG. 14B shows the same left and right hands that are shown in FIG. 14A, but as the left and right hands existed after being treated only with a hydrocortisone-containing solid composition of the invention in a form of a large solid stick, prepared in the manner described in Example 6, and having the larger size shown in FIG. 1, with about 100 applications of about 0.5 ml/application of the composition being applied to the palm spaced equally apart over a period of thirty days (i.e., about 3-4 applications per day). A comparison of the left and right hands that are shown in FIG. 14A with the left and right hands that are shown in FIG. 14B show that the dryness and cracks that are shown in FIG. 14A are significantly moisturized and reduced, and that the cuts that are shown in FIG. 14A have completely disappeared (i.e., have a 100% improvement).

FIG. 14A shows the same palmar aspects of the same left and right hands, as they were present prior to receiving any type of treatment with a composition of the invention for the dryness, cracks, and cuts appearing thereon, with an emphasis on the palms, thumbs, and index fingers of both hands. FIG. 14B shows the same left and right hands that are shown in FIG. 14A, but as the left and right hands existed after being treated only with a hydrocortisone-containing solid composition of the invention (in the manner described above). A comparison of the left and right hands that are shown in FIG.

14A with the left and right hands that are shown in FIG. 14B shows that the dryness and cracks that are shown in FIG. 14A are significantly moisturized and reduced, and that the cuts that are shown in FIG. 14A have completely disappeared (i.e., have a 100% improvement).

The experiments that are described in this example show the very significant advantages and benefits of hydrocortisone-containing topical compositions of the present invention, which were very efficacious in healing the above-described skin disorders, in comparison with other known hydrocortisone-containing topical compositions, which were not efficacious in healing the same skin disorders on the same hands of the same patient.

EXAMPLE 11

Testing of Hydrocortisone Composition Prepared in Example 6 on Face of Thirty-Five-Year-Old Female Patient Having Seborrheic Dermatitis In the topical skin treatment experiments that are described below, a hydrocortisone formulation prepared as described in Example 6, and in a form of a small solid stick having the smaller size shown in FIG. 1, was applied to the face of a thirty-five-year-old female patient having seborrheic dermatitis, whose initials are SN, at an application rate of 21 applications of about 0.1 ml/application of the composition being equally spaced apart over a period of 7 days (i.e., 3 applications per day). These experiments were conducted by Joel Schlessinger, M.D., FAAD, FAACS, a board certified dermatologist and cosmetic surgeon.

Figure 15A:
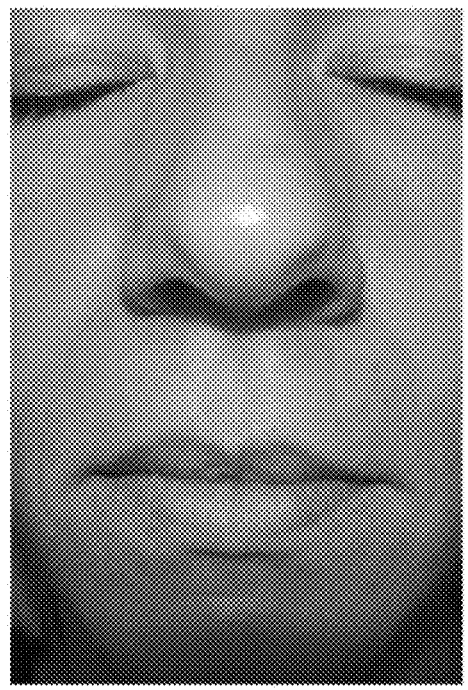
FIG. 15A shows this face as it was present prior to receiving any type of treatment for the erythema of the nasolabial folds appearing thereon.
Figure 15B:
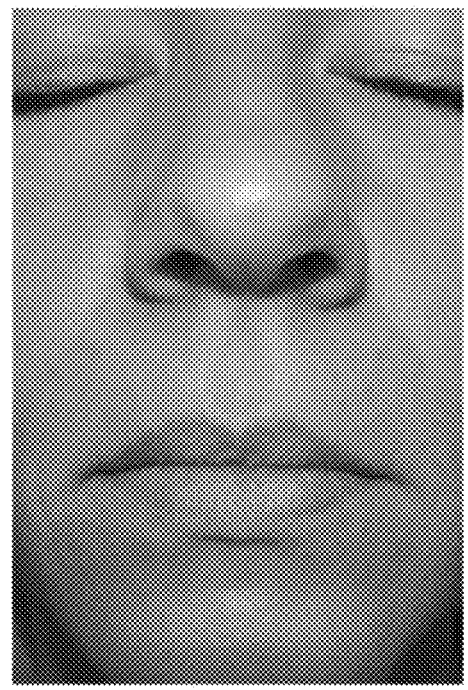
FIG. 15B shows the same face that is shown in FIG. 15A, but as the face existed after being treated only with a hydrocortisone-containing solid composition of the invention in a form of a small solid stick, prepared in the manner described in Example 6, and having the smaller size shown in FIG. 1, with 21 applications of about 0.1 ml/application of the composition being applied to the nasolabial folds spaced equally apart over a period of seven days (i.e., 3 applications per day). A comparison of the face that is shown in FIG. 15A with the face that is shown in FIG. 15B shows that the scaling and erythema that is shown in FIG. 15A was significantly reduced.

FIG. 15A shows this patient's face as it was present prior to receiving any type of treatment for the erythema of the nasolabial folds appearing thereon. FIG. 15B shows the same face that is shown in FIG. 15A, but as the face existed after being treated only with the hydrocortisone-containing solid composition (in the manner described above). A comparison of the face that is shown in FIG. 15A with the face that is shown in FIG. 15B shows that the scaling and erythema that is shown in FIG. 15A was significantly reduced.

EXAMPLE 12

Testing of Hydrocortisone Composition Prepared in Example 6 on Face of Forty-One-Year-Old Male Patient Having Seborrheic Dermatitis In the topical skin treatment experiments that are described below, a hydrocortisone formulation prepared as described in Example 6, and in a form of a small solid stick having the smaller size shown in FIG. 1, was applied to the face of a forty-one-year-old male patient having seborrheic dermatitis, whose initials are JT, at an application rate of 21 applications of about 0.1 ml/application of the composition being equally spaced apart over a period of 7 days (i.e., 3 applications per day). These experiments were conducted by Joel Schlessinger, M.D., FAAD, FAACS, a board certified dermatologist and cosmetic surgeon.

Figure 16A:
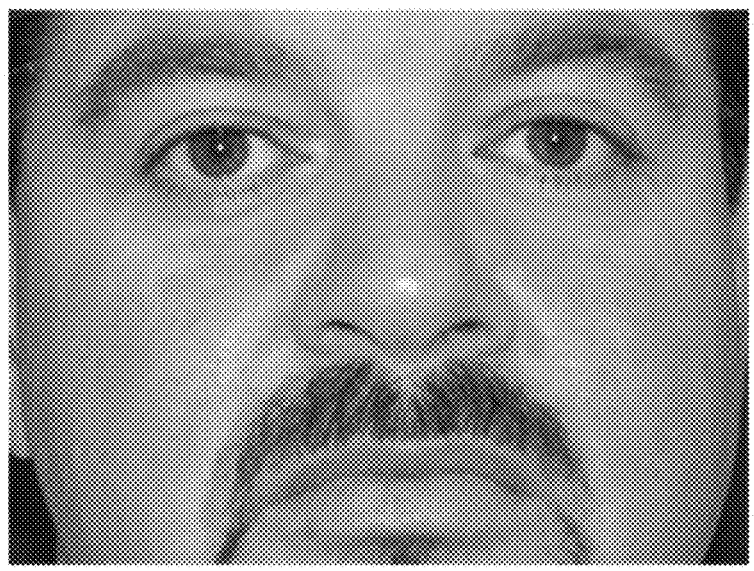
FIG. 16A shows this face as it was present prior to receiving any type of treatment for the seborrheic dermatitis appearing thereon.
Figure 16B:
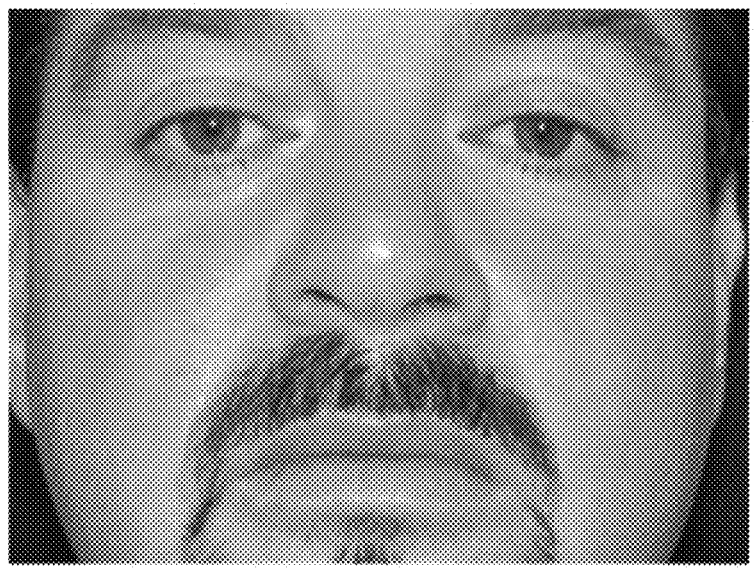
FIG. 16B shows the same face that is shown in FIG. 16A, but as the face existed after being treated only with a hydrocortisone-containing solid composition of the invention in a form of a small solid stick, prepared in the manner described in Example 6, and having the smaller size shown in FIG. 1, with 21 applications of about 0.1 ml/application of the composition being applied to the seborrheic dermatitis present on the face spaced equally apart over a period of 7 days (i.e., 3 applications per day). A comparison of the face that is shown in FIG. 16A with the face that is shown in FIG. 16B shows that the seborrheic dermatitis, scaling and erythema that is shown in FIG. 16A was significantly reduced.

FIG. 16A shows this patient's face as it was present prior to receiving any type of treatment for the seborrheic dermatitis appearing thereon. FIG. 16B shows the same face that is shown in FIG. 16A, but as the face existed after being treated only with the hydrocortisone-containing solid composition (in the manner described above). A comparison of the face that is shown in FIG. 16A with the face that is shown in FIG. 16B shows that the seborrheic dermatitis, scaling and erythema that is shown in FIG. 16A was significantly reduced.

EXAMPLE 13

Testing of Hydrocortisone Composition Prepared in Example 6 on Face of Seventeen-Year-Old Female Patient Having Eczema In the topical skin treatment experiments that are described below, a hydrocortisone formulation prepared as described in Example 6, and in a form of a small solid stick having the smaller size shown in FIG. 1, was applied to the face of a 17-year-old female patient having eczema, whose initials are SR, at an application rate of 21 applications of about 0.1 ml/application of the composition being equally spaced apart over a period of 7 days (i.e., 3 applications per day). These experiments were conducted by Joel Schlessinger, M.D., FAAD, FAACS, a board certified dermatologist and cosmetic surgeon.

Figure 17A:
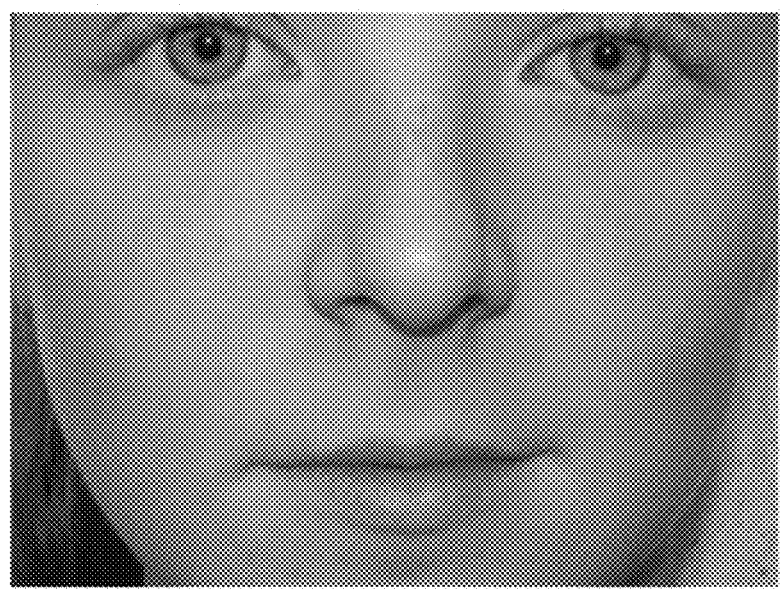
FIG. 17A shows this face as it was present prior to receiving any type of treatment for the eczema appearing thereon.
Figure 17B:
FIG. 17B shows the same face that is shown in FIG. 17A, but as the face existed after being treated only with a hydrocortisone-containing solid composition of the invention in a form of a small solid stick, prepared in the manner described in Example 6, and having the smaller size shown in FIG. 1, with 21 applications of about 0.1 ml/application of the composition being applied to the eczema spaced equally apart over a period of 7 days (i.e., 3 applications per day). A comparison of the face that is shown in FIG. 17A with the face that is shown in FIG. 17B shows that the eczema that is shown in FIG. 17A was significantly reduced (by about 80%).

FIG. 17A shows this patient's face as it was present prior to receiving any type of treatment for the eczema appearing thereon. FIG. 17B shows the same face that is shown in FIG. 17A, but as the face existed after being treated only with the hydrocortisone-containing solid composition (in the manner described above). A comparison of the face that is shown in FIG. 17A with the face that is shown in FIG. 17B shows that the eczema that is shown in FIG. 17A was significantly reduced (reduced by about 80%).

EXAMPLE 14

Testing of Hydrocortisone Composition Prepared in Example 6 on Hands of Fifty-Three-Year-Old Female Patient Having Eczema In the topical skin treatment experiments that are described below, a hydrocortisone formulation prepared as described in Example 6, and in a form of a small solid stick having the smaller size shown in FIG. 1, was applied to the hands of a 53-year-old female patient with initials PR for eczema that a steriod ointment was unable to completely clear. Specifically, 18 applications of about 0.1 ml/application of the composition were applied to each hand, the applications being equally spaced apart over a period of 9 days (i.e., 2 applications per day per hand). These experiments were conducted by Joel Schlessinger, M.D., FAAD, FAACS, a board certified dermatologist and cosmetic surgeon.

Figure 18A:
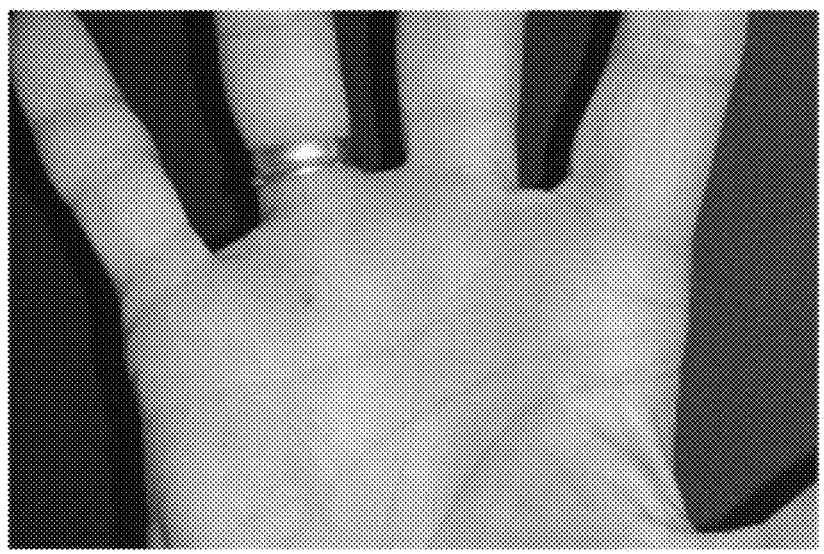
FIG. 18A shows this patient's left hand as it was present prior to receiving any type of treatment for the eczema appearing just below the base of the ring finger.
Figure 18B:
FIG. 18B shows the same hand that is shown in FIG. 18A, but as the hand existed after being treated only with the hydrocortisone-containing solid composition (in the manner described above). A comparison of the hand that is shown in FIG. 18A with the hand that is shown in FIG. 18B shows that the eczema that is shown in FIG. 18A had completely cleared (i.e., a 100% improvement).
Figure 19A:
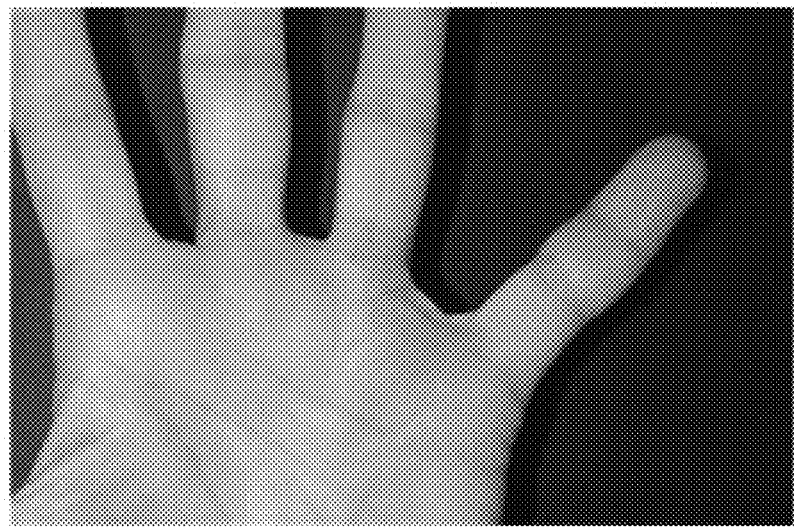
FIG. 19A shows this patient's right hand as it was present prior to receiving any type of treatment for the eczema appearing thereon at the base of the fourth finger.
Figure 19B:
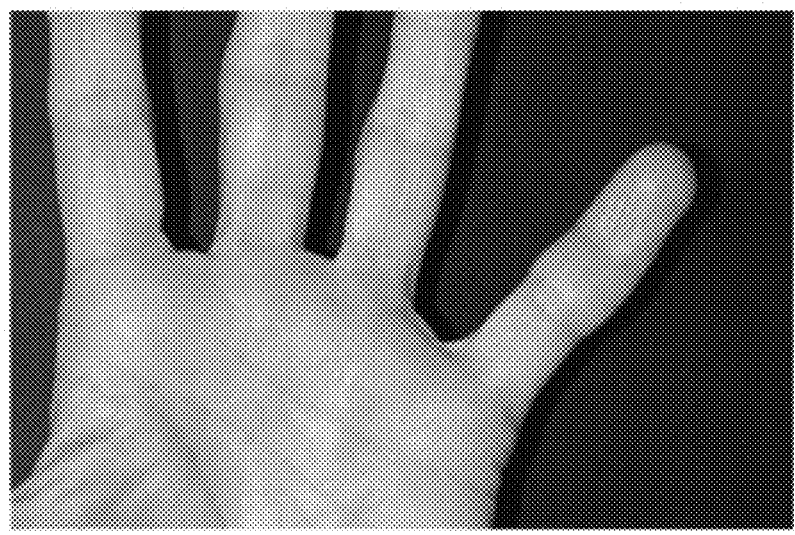
FIG. 19B shows the same hand that is shown in FIG. 19A, but as the hand existed after being treated only with the hydrocortisone-containing solid composition (in the manner described above). A comparison of the hand that is shown in FIG. 19A with the hand that is shown in FIG. 19B shows that the eczema that is shown in FIG. 19A had completely cleared (i.e., a 100% improvement).

FIG. 18A shows this patient's left hand as it was present prior to receiving any type of treatment for the eczema appearing thereon just below the base of the ring finger. FIG. 18B shows the same hand that is shown in FIG. 18A, but as the hand existed after being treated only with the hydrocortisone-containing solid composition (in the manner described above). A comparison of the hand that is shown in FIG. 18A with the hand that is shown in FIG. 18B shows that the eczema that is shown in FIG. 18A had completely cleared (i.e., a 100% improvement). Similarly, FIG. 19A shows this patient's right hand as it was present prior to receiving any type of treatment for the eczema appearing thereon at the base of the fourth finger. FIG. 19B shows the same hand that is shown in FIG. 19A, but as the hand existed after being treated only with the hydrocortisone-containing solid composition (in the manner described above). A comparison of the hand that is shown in FIG. 19A with the hand that is shown in FIG.

19B shows that the eczema that is shown in FIG. 19A had completely cleared (i.e., a 100% improvement).

While the present invention has been described herein with specificity, and with reference to certain preferred embodiments thereof, those of ordinary skill in the art will recognize numerous variations, modifications and substitutions of that which has been described which can be made, and which are within the scope and spirit of the invention. It is intended that all of these modifications and variations be within the scope of the present invention as described and claimed herein, and that the invention be limited only by the scope of the claims which follow, and that such claims be interpreted as broadly as is reasonable.

Throughout this document, various books, patents, patent applications, journal articles, web sites and other publications have been cited. The entireties of each of these books, patents, patent applications, journal articles, web sites and other publications are hereby incorporated by reference herein.

What is claimed is:

1. A topical base composition in a solid or semi-solid form for use as a carrier vehicle for one or a plurality of active agents, consisting of: (i) *Limnanthes Alba* (Meadowfoam) Seed Oil, *Butyrospermum Parkii* (Shea Butter) Extract, (ii) *Ricinus Communis* (Castor) Seed Oil (and) *Glycine Soja* (Soybean) Germ Extract (and) *Zea Mays* (Corn) Starch (and) Silica, (iii) $C_{12-15}$ Alkyl Benzoate, and (iv) bees wax, each in amounts that are effective for collectively forming a base composition having an ability to function effectively as a topically-applied carrier vehicle for the active agents, wherein the base composition is effective in promoting or causing a penetration of the active agents within one or more layers, tissues, or layers and tissues, of skin of a mammal that is damaged, injured, diseased or has an inflammatory reaction or condition.

2. A topical base composition in a solid or semi-solid form for use as a carrier vehicle for one or a plurality of active agents, consisting of: (i) *Limnanthes Alba* (Meadowfoam) Seed Oil, *Butyrospermum Parkii* (Shea Butter) Extract, (ii) *Ricinus Communis* (Castor) Seed Oil (and) *Glycine Soja* (Soybean) Germ Extract (and) *Zea Mays* (Corn) Starch (and) Silica, (iii) $C_{12-15}$ Alkyl Benzoate, and (iv) bees wax, and one or a plurality of plant oils, plant seed oils, fatty alcohols or fats, or any combination thereof, each in combined amounts that are effective for collectively forming a base composition having an ability to function effectively as a topically-applied carrier vehicle for the active agents, wherein the base composition is effective in promoting or causing a penetration of the active agents within one or more layers, tissues, or layers and tissues, of skin of a mammal that is damaged, injured, diseased or has an inflammatory reaction or condition.

3. A topical base composition in a solid or semi-solid form for use as a carrier vehicle for one or a plurality of active agents, consisting of: (i) *Limnanthes Alba* (Meadowfoam) Seed Oil, *Butyrospermum Parkii* (Shea Butter) Extract, (ii) *Ricinus Communis* (Castor) Seed Oil (and) *Glycine Soja* (Soybean) Germ Extract (and) *Zea Mays* (Corn) Starch (and) Silica, (iii) $C_{12-15}$ Alkyl Benzoate, and (iv) bees wax, and one or a plurality of flavorings, and one or a plurality of plant oils, plant seed oils, fatty alcohols or fats, or any combination thereof, each in combined amounts that are effective for collectively forming a base composition having an ability to function effectively as a topically-applied carrier vehicle for the active agents, wherein the base composition is effective in promoting or causing a penetration of the active agents within one or more layers, tissues, or layers and tissues, of skin of a mammal that is damaged, injured, diseased or has an inflammatory reaction or condition, and wherein the base composition does not have a bitter taste or odor, has no distinctive taste or odor or has a pleasant taste or odor.

4. A topical base composition in a solid or semi-solid form for use as a carrier vehicle for one or a plurality of active agents, comprising (i) 11.00 weight percent *Limnanthes Alba* (Meadowfoam) Seed Oil, *Butyrospermum Parkii* (Shea Butter) Extract, (ii) 10.00 weight percent *Ricinus Communis* (Castor) Seed Oil (and) *Glycine Soja* (Soybean) Germ Extract (and) *Zea Mays* (Corn) Starch (and) Silica, (iii) 15.00 weight percent $C_{12-15}$ Alkyl Benzoate, (iv) 11.00 weight percent Bees Wax, (v) 26.00 weight percent Castor Oil, (vi) 20.00 weight percent Stearyl Alcohol, (vii) 7.00 weight percent Cocoa Butter, and (viii) 0.00 weight percent Flavoring (Vanilla), wherein the base composition has an ability to function effectively as a topically-applied carrier vehicle for the active agents, and wherein the base composition is effective in promoting or causing a penetration of the active agents within one or more layers, tissues, or layers and tissues, of skin of a mammal that is damaged, injured, diseased or has an inflammatory reaction or condition.

5. A topical base composition in a solid or semi-solid form for use as a carrier vehicle for one or a plurality of active agents, consisting of:
   (a) *Limnanthes Alba* (Meadowfoam) Seed Oil, *Butyrospermum Parkii* (Shea Butter) Extract, wherein the *Limnanthes Alba* (Meadowfoam) Seed Oil, *Butyrospermum Parkii* (Shea Butter) Extract is present in the base composition in an amount ranging from about 6 to about 25 weight percent;
   (b) *Ricinus Communis* (Castor) Seed Oil (and) *Glycine Soja* (Soybean) Germ Extract (and) *Zea Mays* (Corn) Starch (and) Silica, wherein the *Ricinus Communis* (Castor) Seed Oil (and) *Glycine Soja* (Soybean) Germ Extract (and) *Zea Mays* (Corn) Starch (and) Silica is present in the base composition in an amount ranging from about 5 to about 39 weight percent;
   (c) $C_{12-15}$ Alkyl Benzoate, wherein the $C_{12-15}$ Alkyl Benzoate is present in the base composition in an amount ranging from about 9 to about 25 weight percent;
   (d) bees wax, wherein the bees wax is present in the base composition in an amount ranging from about 6 to about 43 weight percent;
   (e) optionally, one or a plurality of plant oils or plant seed oils, wherein the plant oils or plant seed oils are present in the base composition in a combined amount ranging from about 0 to about 38.5 weight percent;
   (f) optionally, one or a plurality of fatty alcohols, wherein the fatty alcohols are present in the base composition in a combined amount ranging from about 0 to about 25 weight percent;
   (g) optionally, one or a plurality of fats, wherein the fats are present in the base composition in a combined amount ranging from about 0 to about 12 weight percent; and
   (h) optionally, one or a plurality of flavorings, wherein the flavorings are present in the base composition in a combined amount ranging from about 0 to about 3.5 weight percent;
wherein the base composition has an ability to function effectively as a topically-applied carrier vehicle for the active agents, and wherein the base composition is effective in promoting or causing a penetration of the active agents within one or more layers, tissues, or layers and tissues, of skin of a mammal that is damaged, injured, diseased or has an inflammatory reaction or condition.

6. A base composition of claim 5, wherein the base composition includes one or more flavorings.

7. A topical base composition in a solid or semi-solid form for use as a carrier vehicle for one or a plurality of active agents, consisting of:
(a) *Limnanthes Alba* (Meadowfoam) Seed Oil, *Butyrospermum Parkii* (Shea Butter) Extract, wherein the *Limnanthes Alba* (Meadowfoam) Seed Oil, *Butyrospermum Parkii* (Shea Butter) Extract is present in the base composition in an amount ranging from about 6 to about 25 weight percent;
(b) *Ricinus Communis* (Castor) Seed Oil (and) *Glycine Soja* (Soybean) Germ Extract (and) *Zea Mays* (Corn) Starch (and) Silica, wherein the *Ricinus Communis* (Castor) Seed Oil (and) *Glycine Soja* (Soybean) Germ Extract (and) *Zea Mays* (Corn) Starch (and) Silica is present in the base composition in an amount ranging from about 5 to about 39 weight percent;
(c) $C_{12-15}$ Alkyl Benzoate, wherein the $C_{12-15}$ Alkyl Benzoate is present in the base composition in an amount ranging from about 9 to about 25 weight percent;
(d) bees wax, wherein the bees wax is present in the base composition in an amount ranging from about 6 to about 43 weight percent;
(e) one or more plant oils or plant seed oils, wherein the plant oils or plant seed oils are present in the base composition in a combined amount ranging from about 0.1 to about 38.5 weight percent;
(f) one or more fatty alcohols, wherein the fatty alcohols are present in the base composition in a combined amount ranging from about 0.1 to about 25 weight percent;
(g) one or more fats, wherein the fats are present in the base composition in a combined amount ranging from about 0.1 to about 12 weight percent; and
(h) optionally, one or more flavorings, wherein the flavorings are present in the base composition in an amount ranging from about 0 to about 3.5 weight percent;
wherein the base composition has an ability to function effectively as a topically-applied carrier vehicle for the active agents, and wherein the base composition is effective in promoting or causing a penetration of the active agents within one or more layers, tissues, or layers and tissues, of skin of a mammal that is damaged, injured, diseased or has an inflammatory reaction or condition.

8. A base composition of claim 7, wherein the base composition includes one or more flavorings.

9. A topical base composition in a solid or semi-solid form for use as a carrier vehicle for one or a plurality of active agents, consisting of:
(a) *Limnanthes Alba* (Meadowfoam) Seed Oil, *Butyrospermum Parkii* (Shea Butter) Extract, wherein the *Limnanthes Alba* (Meadowfoam) Seed Oil, *Butyrospermum Parkii* (Shea Butter) Extract is present in the base composition in an amount ranging from about 6 to about 16 weight percent;
(b) *Ricinus Communis* (Castor) Seed Oil (and) *Glycine Soja* (Soybean) Germ Extract (and) *Zea Mays* (Corn) Starch (and) Silica, wherein the *Ricinus Communis* (Castor) Seed Oil (and) *Glycine Soja* (Soybean) Germ Extract (and) *Zea Mays* (Corn) Starch (and) Silica is present in the base composition in an amount ranging from about 5 to about 15 weight percent;
(c) $C_{12-15}$ Alkyl Benzoate, wherein the $C_{12-15}$ Alkyl Benzoate is present in the base composition in an amount ranging from about 10 to about 20 weight percent;
(d) bees wax, wherein the bees wax is present in the base composition in an amount ranging from about 6 to about 16 weight percent;
(e) one or more plant oils or plant seed oils, wherein the plant oils or plant seed oils are present in the base composition in a combined amount ranging from about 13 to about 38.5 weight percent;
(f) one or more fatty alcohols, wherein the fatty alcohols are present in the base composition in a combined amount ranging from about 15 to about 25 weight percent;
(g) one or more fats, wherein the fats are present in the base composition in a combined amount ranging from about 2 to about 12 weight percent; and
(h) optionally, one or more flavorings, wherein the flavorings are present in the base composition in an amount ranging from about 0 to about 3.5 weight percent;
wherein the base composition has an ability to function effectively as a topically-applied carrier vehicle for the active agents, and wherein the base composition is effective in promoting or causing a penetration of the active agents within one or more layers, tissues, or layers and tissues, of skin of a mammal that is damaged, injured, diseased or has an inflammatory reaction or condition.

10. A base composition of claim 9, wherein the base composition includes one or more flavorings.

11. A topical base composition in a solid or semi-solid form for use as a carrier vehicle for one or a plurality of active agents, consisting of:
(a) *Limnanthes Alba* (Meadowfoam) Seed Oil, *Butyrospermum Parkii* (Shea Butter) Extract, wherein the *Limnanthes Alba* (Meadowfoam) Seed Oil, *Butyrospermum Parkii* (Shea Butter) Extract is present in the base composition in an amount ranging from about 10 to about 12 weight percent;
(b) *Ricinus Communis* (Castor) Seed Oil (and) *Glycine Soja* (Soybean) Germ Extract (and) *Zea Mays* (Corn) Starch (and) Silica, wherein the *Ricinus Communis* (Castor) Seed Oil (and) *Glycine Soja* (Soybean) Germ Extract (and) *Zea Mays* (Corn) Starch (and) Silica is present in the base composition in an amount ranging from about 9 to about 11 weight percent;
(c) $C_{12-15}$ Alkyl Benzoate, wherein the $C_{12-15}$ Alkyl Benzoate is present in the base composition in an amount ranging from about 14 to about 16 weight percent;
(d) bees wax, wherein the bees wax is present in the base composition in an amount ranging from about 10 to about 12 weight percent;
(e) one or more plant oils or plant seed oils, wherein the plant oils or plant seed oils are present in the base composition in a combined amount ranging from about 24.5 to about 27 weight percent;
(f) one or more fatty alcohols, wherein the fatty alcohols are present in the base composition in a combined amount ranging from about 19 to about 21 weight percent;
(g) one or more fats, wherein the fats are present in the base composition in a combined amount ranging from about 6 to about 8 weight percent; and
(h) optionally, one or more flavorings, wherein the flavorings are present in the base composition in an amount ranging from about 0 to about 3.5 weight percent;
wherein the base composition has an ability to function effectively as a topically-applied carrier vehicle for the active agents, and wherein the base composition is effective in promoting or causing a penetration of the active agents within one or more layers, tissues, or layers and tissues, of skin of a mammal that is damaged, injured, diseased or has an inflammatory reaction or condition.

12. A base composition of claim 11, wherein the base composition includes one or more flavorings.

13. A base composition of claim 5, wherein the plant oil or plant seed oil is castor oil, the fatty alcohol is stearyl alcohol or the fat is cocoa butter, or any combination thereof.

14. A base composition of claim 6, wherein the plant oil or plant seed oil is castor oil, the fatty alcohol is stearyl alcohol or the fat is cocoa butter, or any combination thereof.

15. A base composition of claim 7, wherein the plant oil or plant seed oil is castor oil, the fatty alcohol is stearyl alcohol or the fat is cocoa butter, or any combination thereof.

16. A base composition of claim 8, wherein the plant oil or plant seed oil is castor oil, the fatty alcohol is stearyl alcohol or the fat is cocoa butter, or any combination thereof.

17. A base composition of claim 9, wherein the plant oil or plant seed oil is castor oil, the fatty alcohol is stearyl alcohol or the fat is cocoa butter, or any combination thereof.

18. A base composition of claim 10, wherein the plant oil or plant seed oil is castor oil, the fatty alcohol is stearyl alcohol or the fat is cocoa butter, or any combination thereof.

19. A base composition of claim 11, wherein the plant oil or plant seed oil is castor oil, the fatty alcohol is stearyl alcohol or the fat is cocoa butter, or any combination thereof.

20. A base composition of claim 12, wherein the plant oil or plant seed oil is castor oil, the fatty alcohol is stearyl alcohol or the fat is cocoa butter, or any combination thereof.

21. A composition in a solid or semi-solid form for topical application to the skin of a mammal for repairing, improving or fully healing a skin disorder, disease, adverse condition, or other condition that requires, or could benefit from, improvement, or for causing the mammal's skin to experience a reduction in pain, soreness or itchiness, or a combination thereof, comprising (i) 1.0 weight percent Hydrocortisone, (ii) 11.00 weight percent *Limnanthes Alba* (Meadowfoam) Seed Oil, *Butyrospermum Parkii* (Shea Butter) Extract, (iii) 10.00 weight percent *Ricinus Communis* (Castor) Seed Oil (and) *Glycine Soja* (Soybean) Germ Extract (and) *Zea Mays* (Corn) Starch (and) Silica, (iv) 15.00 weight percent $C_{12-15}$ Alkyl Benzoate, (v) 11.00 weight percent Bees Wax; (vi) 24.50 weight percent Castor Oil, (vii) 20.00 weight percent Stearyl Alcohol, (viii) 7.00 weight percent Cocoa Butter, and (ix) 0.50 weight percent Flavoring (Vanilla), wherein the composition is effective in repairing, improving or fully healing skin of the mammal that is damaged, injured, diseased, has an inflammatory reaction or condition, or requires, or could benefit from, improvement, or in causing the mammal's skin to experience a reduction in pain, soreness or itchiness, or a combination thereof, and wherein the composition has an ability to act within one or more layers, tissues, or layers and tissues, of the skin of the mammal that is damaged, injured, diseased, has an inflammatory reaction or condition, or requires, or could benefit from, improvement.

22. A composition in a solid or semi-solid form for topical application to the skin of a mammal for repairing, improving or fully healing a skin disorder, disease, adverse condition, or other condition that requires, or could benefit from, improvement, or for causing the mammal's skin to experience a reduction in pain, soreness or itchiness, or a combination thereof, consisting of:

(a) one or a plurality of active agents, wherein the active agents are present in the composition in a combined amount ranging from about 0.1 to about 5 weight percent;

(b) *Limnanthes Alba* (Meadowfoam) Seed Oil, *Butyrospermum Parkii* (Shea Butter) Extract, wherein the *Limnanthes Alba* (Meadowfoam) Seed Oil, *Butyrospermum Parkii* (Shea Butter) Extract is present in the composition in an amount ranging from about 6 to about 25 weight percent;

(c) *Ricinus Communis* (Castor) Seed Oil (and) *Glycine Soja* (Soybean) Germ Extract (and) *Zea Mays* (Corn) Starch (and) Silica, wherein the *Ricinus Communis* (Castor) Seed Oil (and) *Glycine Soja* (Soybean) Germ Extract (and) *Zea Mays* (Corn) Starch (and) Silica is present in the composition in an amount ranging from about 5 to about 39 weight percent;

(d) $C_{12-15}$ Alkyl Benzoate, wherein the $C_{12-15}$ Alkyl Benzoate is present in the composition in an amount ranging from about 9 to about 25 weight percent;

(e) bees wax, wherein the bees wax is present in the composition in an amount ranging from about 6 to about 43 weight percent;

(f) optionally, one or a plurality of plant oils or plant seed oils, wherein the plant oils or plant seed oils are present in the composition in a combined amount ranging from about 0 to about 37.5 weight percent;

(g) optionally, one or a plurality of fatty alcohols, wherein the fatty alcohols are present in the composition in a combined amount ranging from about 0 to about 25 weight percent;

(h) optionally, one or a plurality of fats, wherein the fats are present in the composition in a combined amount ranging from about 0 to about 12 weight percent; and (i) optionally, one or a plurality of flavorings, wherein the flavorings are present in the composition in a combined amount ranging from about 0 to about 3.5 weight percent, wherein the composition is effective in repairing, improving or fully healing skin of the mammal that is damaged, injured, diseased, has an inflammatory reaction or condition, or requires, or could benefit from, improvement, or in causing the mammal's skin to experience a reduction in pain, soreness or itchiness, or a combination thereof, and wherein the composition has an ability to act within one or more layers, tissues, or layers and tissues, of the skin of the mammal that is damaged, injured, diseased, has an inflammatory reaction or condition, or requires, or could benefit from, improvement.

23. A composition of claim 22, wherein the composition includes one or more flavorings.

24. A composition of claim 22, wherein the active agent is hydrocortisone.

25. A composition of claim 23, wherein the active agent is hydrocortisone.

26. A composition in a solid or semi-solid form for topical application to the skin of a mammal for repairing, improving or fully healing a skin disorder, disease, adverse condition, or other condition that requires, or could benefit from, improvement, or for causing the mammal's skin to experience a reduction in pain, soreness or itchiness, or a combination thereof, consisting of:

(a) one or a plurality of active agents, wherein the active agents are present in the composition in a combined amount ranging from about 0.1 to about 5 weight percent;

(b) *Limnanthes Alba* (Meadowfoam) Seed Oil, *Butyrospermum Parkii* (Shea Butter) Extract, wherein the *Limnanthes Alba* (Meadowfoam) Seed Oil, *Butyrospermum Parkii* (Shea Butter) Extract is present in the composition in an amount ranging from about 6 to about 25 weight percent;

(c) *Ricinus Communis* (Castor) Seed Oil (and) *Glycine Soja* (Soybean) Germ Extract (and) *Zea Mays* (Corn) Starch (and) Silica, wherein the *Ricinus Communis*

(Castor) Seed Oil (and) *Glycine Soja* (Soybean) Germ Extract (and) *Zea Mays* (Corn) Starch (and) Silica is present in the composition in an amount ranging from about 5 to about 39 weight percent;

(d) $C_{12-15}$ Alkyl Benzoate, wherein the $C_{12-15}$ Alkyl Benzoate is present in the composition in an amount ranging from about 9 to about 25 weight percent;

(e) bees wax, wherein the bees wax is present in the composition in an amount ranging from about 6 to about 43 weight percent;

(f) one or a plurality of plant oils or plant seed oils, wherein the plant oils or plant seed oils are present in the composition in a combined amount ranging from about 0.1 to about 37.5 weight percent;

(g) one or a plurality of fatty alcohols, wherein the fatty alcohols are present in the composition in a combined amount ranging from about 0.1 to about 25 weight percent;

(h) one or a plurality of fats, wherein the fats are present in the composition in a combined amount ranging from about 0.1 to about 12 weight percent; and (i) optionally, one or a plurality of flavorings, wherein the flavorings are present in the composition in a combined amount ranging from about 0 to about 3.5 weight percent, wherein the composition is effective in repairing, improving or fully healing skin of the mammal that is damaged, injured, diseased, has an inflammatory reaction or condition, or requires, or could benefit from, improvement, or in causing the mammal's skin to experience a reduction in pain, soreness or itchiness, or a combination thereof, and wherein the composition has an ability to act within one or more layers, tissues, or layers and tissues, of the skin of the mammal that is damaged, injured, diseased, has an inflammatory reaction or condition, or requires, or could benefit from, improvement.

27. A composition of claim 26, wherein the composition includes one or more flavorings.

28. A composition of claim 26, wherein the active agent is hydrocortisone.

29. A composition of claim 27, wherein the active agent is hydrocortisone.

30. A composition in a solid or semi-solid form for topical application to the skin of a mammal for repairing, improving or fully healing a skin disorder, disease, adverse condition, or other condition that requires, or could benefit from, improvement, or for causing the mammal's skin to experience a reduction in pain, soreness or itchiness, or a combination thereof, consisting of:

(a) one or a plurality of active agents, wherein the active agents are present in the composition in a combined amount ranging from about 0.5 to about 3 weight percent;

(b) *Limnanthes Alba* (Meadowfoam) Seed Oil, *Butyrospermum Parkii* (Shea Butter) Extract, wherein the *Limnanthes Alba* (Meadowfoam) Seed Oil, *Butyrospermum Parkii* (Shea Butter) Extract is present in the composition in an amount ranging from about 6 to about 16 weight percent;

(c) *Ricinus Communis* (Castor) Seed Oil (and) *Glycine Soja* (Soybean) Germ Extract (and) *Zea Mays* (Corn) Starch (and) Silica, wherein the *Ricinus Communis* (Castor) Seed Oil (and) *Glycine Soja* (Soybean) Germ Extract (and) *Zea Mays* (Corn) Starch (and) Silica is present in the composition in an amount ranging from about 5 to about 15 weight percent;

(d) $C_{12-15}$ Alkyl Benzoate, wherein the $C_{12-15}$ Alkyl Benzoate is present in the composition in an amount ranging from about 10 to about 20 weight percent;

(e) bees wax, wherein the bees wax is present in the composition in an amount ranging from about 6 to about 16 weight percent;

(f) one or a plurality of plant oils or plant seed oils, wherein the plant oils or plant seed oils are present in the composition in a combined amount ranging from about 12 to about 37.5 weight percent;

(g) one or a plurality of fatty alcohols, wherein the fatty alcohols are present in the composition in a combined amount ranging from about 15 to about 25 weight percent;

(h) one or a plurality of fats, wherein the fats are present in the composition in a combined amount ranging from about 2 to about 12 weight percent; and (i) optionally, one or a plurality of flavorings, wherein the flavorings are present in the composition in a combined amount ranging from about 0 to about 2.5 weight percent, wherein the composition is effective in repairing, improving or fully healing skin of the mammal that is damaged, injured, diseased, has an inflammatory reaction or condition, or requires, or could benefit from, improvement, or in causing the mammal's skin to experience a reduction in pain, soreness or itchiness, or a combination thereof, and wherein the composition has an ability to act within one or more layers, tissues, or layers and tissues, of the skin of the mammal that is damaged, injured, diseased, has an inflammatory reaction or condition, or requires, or could benefit from, improvement.

31. A composition of claim 30, wherein the composition includes one or more flavorings.

32. A composition of claim 30, wherein the active agent is hydrocortisone.

33. A composition of claim 31, wherein the active agent is hydrocortisone.

34. A composition in a solid or semi-solid form for topical application to the skin of a mammal for repairing, improving or fully healing a skin disorder, disease, adverse condition, or other condition that requires, or could benefit from, improvement, or for causing the mammal's skin to experience a reduction in pain, soreness or itchiness, or a combination thereof, consisting of:

(a) one or a plurality of active agents, wherein the active agents are present in the composition in a combined amount ranging from about 0.8 to about 2 weight percent;

(b) *Limnanthes Alba* (Meadowfoam) Seed Oil, *Butyrospermum Parkii* (Shea Butter) Extract, wherein the *Limnanthes Alba* (Meadowfoam) Seed Oil, *Butyrospermum Parkii* (Shea Butter) Extract is present in the composition in an amount ranging from about 10 to about 12 weight percent;

(c) *Ricinus Communis* (Castor) Seed Oil (and) *Glycine Soja* (Soybean) Germ Extract (and) *Zea Mays* (Corn) Starch (and) Silica, wherein the *Ricinus Communis* (Castor) Seed Oil (and) *Glycine Soja* (Soybean) Germ Extract (and) *Zea Mays* (Corn) Starch (and) Silica is present in the composition in an amount ranging from about 9 to about 11 weight percent;

(d) $C_{12-15}$ Alkyl Benzoate, wherein the $C_{12-15}$ Alkyl Benzoate is present in the composition in an amount ranging from about 14 to about 16 weight percent;

(e) bees wax, wherein the bees wax is present in the composition in an amount ranging from about 10 to about 12 weight percent;

(f) one or a plurality of plant oils or plant seed oils, wherein the plant oils or plant seed oils are present in the composition in a combined amount ranging from about 23.5 to about 26 weight percent;

(g) one or a plurality of fatty alcohols, wherein the fatty alcohols are present in the composition in a combined amount ranging from about 19 to about 21 weight percent;

(h) one or a plurality of fats, wherein the fats are present in the composition in a combined amount ranging from about 6 to about 8 weight percent; and (i) optionally, one or a plurality of flavorings, wherein the flavorings are present in the composition in a combined amount ranging from about 0.3 to about 1.5 weight percent, wherein the composition is effective in repairing, improving or fully healing skin of the mammal that is damaged, injured, diseased, has an inflammatory reaction or condition, or requires, or could benefit from, improvement, or in causing the mammal's skin to experience a reduction in pain, soreness or itchiness, or a combination thereof, and wherein the composition has an ability to act within one or more layers, tissues, or layers and tissues, of the skin of the mammal that is damaged, injured, diseased, has an inflammatory reaction or condition, or requires, or could benefit from, improvement.

35. A composition of claim 34, wherein the composition includes one or more flavorings.

36. A composition of claim 34, wherein the active agent is hydrocortisone.

37. A composition of claim 36, wherein the active agent is hydrocortisone.

38. A composition of claim 26, wherein the plant oil or plant seed oil is castor oil, the fatty alcohol is stearyl alcohol or the fat is cocoa butter, or any combination thereof.

39. A composition of claim 27, wherein the plant oil or plant seed oil is castor oil, the fatty alcohol is stearyl alcohol or the fat is cocoa butter, or any combination thereof.

40. A composition of claim 28, wherein the plant oil or plant seed oil is castor oil, the fatty alcohol is stearyl alcohol or the fat is cocoa butter, or any combination thereof.

41. A composition of claim 29, wherein the plant oil or plant seed oil is castor oil, the fatty alcohol is stearyl alcohol or the fat is cocoa butter, or any combination thereof.

42. A composition of claim 30, wherein the plant oil or plant seed oil is castor oil, the fatty alcohol is stearyl alcohol or the fat is cocoa butter, or any combination thereof.

43. A composition of claim 31, wherein the plant oil or plant seed oil is castor oil, the fatty alcohol is stearyl alcohol or the fat is cocoa butter, or any combination thereof.

44. A composition of claim 32, wherein the plant oil or plant seed oil is castor oil, the fatty alcohol is stearyl alcohol or the fat is cocoa butter, or any combination thereof.

45. A composition of claim 33, wherein the plant oil or plant seed oil is castor oil, the fatty alcohol is stearyl alcohol or the fat is cocoa butter, or any combination thereof.

46. A composition of claim 34, wherein the plant oil or plant seed oil is castor oil, the fatty alcohol is stearyl alcohol or the fat is cocoa butter, or any combination thereof.

47. A composition of claim 35, wherein the plant oil or plant seed oil is castor oil, the fatty alcohol is stearyl alcohol or the fat is cocoa butter, or any combination thereof.

48. A composition of claim 36, wherein the plant oil or plant seed oil is castor oil, the fatty alcohol is stearyl alcohol or the fat is cocoa butter, or any combination thereof.

49. A composition of claim 37, wherein the plant oil or plant seed oil is castor oil, the fatty alcohol is stearyl alcohol or the fat is cocoa butter, or any combination thereof.

50. A topical base composition in a solid or semi-solid form for use as a carrier vehicle for one or a plurality of active agents, comprising (i) 11.00 weight percent *Limnanthes Alba* (Meadowfoam) Seed Oil, *Butyrospermum Parkii* (Shea Butter) Extract, (ii) 10.00 weight percent *Ricinus Communis* (Castor) Seed Oil (and) *Glycine Soja* (Soybean) Germ Extract (and) *Zea Mays* (Corn) Starch (and) Silica, (iii) 15.00 weight percent $C_{12-15}$ Alkyl Benzoate, (iv) 11.00 weight percent Bees Wax, (v) 25.50 weight percent Castor Oil, (vi) 20.00 weight percent Stearyl Alcohol, (vii) 7.00 weight percent Cocoa Butter, and (viii) 0.50 weight percent Flavoring (Vanilla), wherein the base composition has an ability to function effectively as a topically-applied carrier vehicle for the active agents, and wherein the base composition is effective in promoting or causing a penetration of the active agents within one or more layers, tissues, or layers and tissues, of skin of a mammal that is damaged, injured, diseased or has an inflammatory reaction or condition.

51. A composition in a solid or semi-solid form for topical application to the skin of a mammal for repairing, improving or fully healing a skin disorder, disease, adverse condition, or other condition that requires, or could benefit from, improvement, or for causing the mammal's skin to experience a reduction in pain, soreness or itchiness, or a combination thereof, comprising (i) 1.0 weight percent Hydrocortisone, (ii) 11.00 weight percent *Limnanthes Alba* (Meadowfoam) Seed Oil, *Butyrospermum Parkii* (Shea Butter) Extract, (iii) 10.00 weight percent *Ricinus Communis* (Castor) Seed Oil (and) *Glycine Soja* (Soybean) Germ Extract (and) *Zea Mays* (Corn) Starch (and) Silica, (iv) 15.00 weight percent $C_{12-15}$ Alkyl Benzoate, (v) 11.00 weight percent Bees Wax, (vi) 25.00 weight percent Castor Oil, (vii) 20.00 weight percent Stearyl Alcohol, (viii) 7.00 weight percent Cocoa Butter, and (ix) 0.00 weight percent Flavoring (Vanilla), wherein the composition is effective in repairing, improving or fully healing skin of the mammal that is damaged, injured, diseased, has an inflammatory reaction or condition, or requires, or could benefit from, improvement, or in causing the mammal's skin to experience a reduction in pain, soreness or itchiness, or a combination thereof, and wherein the composition has an ability to act within one or more layers, tissues, or layers and tissues, of the skin of the mammal that is damaged, injured, diseased, has an inflammatory reaction or condition, or requires, or could benefit from, improvement.

52. A composition of claim 21, claim 22, claim 23, claim 26, claim 27, claim 30, claim 31, claim 34, claim 35, claim 38, claim 39, claim 42, claim 43, claim 46, claim 47 or claim 51, wherein one of the active agents is selected from the group consisting of: clobetasol propionate 0.05%; betamethasone dipropionate 0.25%; halobetasol proprionate 0.05%; diflorasone diacetate 0.05%; fluocinonide 0.05%; halcinonide 0.05%; amcinonide 0.05%; desoximetasone 0.25%; triamcinolone acetonide; 0.5%; mometasone furoate 0.1%; fluticasone propionate 0.005%; betamethasone dipropionate 0.05%; fluocinolone acetonide 0.01-0.2%; hydrocortisone valerate 0.2%; hydrocortisone butyrate 0.1%; flurandrenolide 0.05%; triamcinolone acetonide 0.1%; triamcinolone acetonide 0.1%; fluticasone propionate 0.05%; desonide 0.05%; fluocinolone acetonide 0.025%; hydrocortisone valerate 0.2%; prednicarbate 0.05%; triamcinolone acetonide 0.025%; fluocinolone acetonide 0.01%; desonide 0.05%; hydrocortisone 2.5%; hydrocortisone 1%; topical erythromycin; topical mupirocin; topical retapamulin; topical bacitracin/polymyxin B; topical bacitracin/neomycin/polymyxin B; topical sulfacetamide sodium/urea; natamycin; rimocidin; filipin; nystatin; amphotericin B; candicin; hamycin; miconazole; miconazole nitrate; ketoconazole; clotrimazole; econazole; bifonazole; butoconazole; fenticonazole; isoconazole; oxiconazole; sertaconazole; sulconazole; tioconazole; fluconazole; itraconazole; isavuconazole; ravuconazole; posaconazole; voriconazole; terconazole; abafungin; terbinafine; naftifine; butenafine; anidulafungin; caspofungin; micafungin; polygodial; ciclopirox; ciclopirox olamine; tolnaftate; undecylenic acid; flucytosine; 5-fluorocytosine; griseofulvin; haloprogin; sodium bicarbonate; pimecrolimus 1% Cream; tacrolimus 0.1% ointment; clemastine; diphenhydramine; doxylamine; loratadine; desloratadine; fexofenadine; pheniramine; cetirizine; ebastine; promethazine; chlorpheniramine; levocetirizine; olopatadine; quetiapine; meclizine; dimenhydrinate; embramine; dimethindene; dexchlorpheniramine; vitamin C; cimetidine; famotidine; ranitidine; nizatidine; roxatidine; lafutidine; ciproxifan; clobenpropit; thioperamide; cromoglicate; nedocromil; a 132 adrenergic agonist; acetaminophen; diclofenac; diflunisal; etodolac; fenoprofen; flurbiprofen; ibuprofen; indomethacin; ketoprofen; ketorolac; meclofenamate; mefenamic acid; meloxicam; nabumetone; naproxen; oxaprozin; phenylbutazone; piroxicam; sulindac; tolmetin; celecoxib; buprenorphine; butorphanol; codeine; hydrocodone; hydromorphone; levorphanol; meperidine; methadone; morphine; nalbuphine; oxycodone; oxymorphone; pentazocine; propoxyphene; tramadol; tramadol and acetaminophen; butalbital, acetaminophen, and caffeine; butalbital, aspirin, and caffeine; butalbital, acetaminophen, caffeine, and codeine; hydrocodone and ibuprofen; pentazocine/naloxone; acetaminophen and codeine; dihydrocodeine, acetaminophen, and caffeine; hydrocodone and acetaminophen; oxycodone and acetaminophen; pentazocine and acetaminophen; propoxyphene and acetaminophen; aspirin, caffeine and dihydrocodeine; aspirin and codeine; hydrocodone and aspirin; oxycodone and aspirin; pentazocine and aspirin; propoxyphene, aspirin, and caffeine; capsaicin; benzocaine; benzocaine/menthol; dibucaine; lidocaine; lidocaine/prilocaine; onabotulinumtoxinA; abobotulinumtoxinA; incobotulinumtoxinA; botulinum toxin type A; DEET (N,N-diethyl-m-toluamide); essential oil; icaridin; nepetalactone; citronella oil; permethrin; neem oil; bog myrtle; 3-[N-Butyl-N-acetyl]-aminopropionic acid, ethyl ester; p-aminobenzoic acid; padimate O; phenylbenzimidazole sulfonic acid; cinoxate; dioxybenzone; oxybenzone; homosalate; menthyl anthranilate; octocrylene; octyl methoxycinnamate; octyl salicylate; sulisobenzone; trolamine salicylate; avobenzone; ecamsule; titanium dioxide; zinc oxide; 4-methylbenzylidene camphor; bisoctrizole; bis-ethylhexyloxyphenol methoxyphenyl triazine; disodium phenyl dibenzimidazole tetrasulfonate; drometrizole trisiloxane; benzophenone-9; ethylhexyl triazone; diethylamino hydroxybenzoyl hexyl benzoate; iscotrizinol; polysilicone-15; and isopentenyl-4-methoxycinnamate.

* * * * *